US010767196B2

(12) United States Patent
Lo et al.

(10) Patent No.: US 10,767,196 B2
(45) Date of Patent: Sep. 8, 2020

(54) ENGINEERING AN INCREASE IN ETHANOL PRODUCTION BY ALTERING COFACTOR SPECIFICITY

(71) Applicants: Enchi Corporation, Wellesley Hills, MA (US); Dartmouth College, Hanover, NH (US); UT-BATTELLE, LLC, Oak Ridge, TN (US)

(72) Inventors: Jonathan Lo, Hanover, NH (US); Adam M. Guss, Knoxville, TN (US); Johannes P. Van Dijken, Scheidam (NL); Arthur J. Shaw, IV, Grantham, NH (US); Daniel G. Olson, Norwich, VT (US); Christopher D. Herring, Lebanon, NH (US); D. Aaron Argyros, White River Junction, VT (US); Nicky Caiazza, Rancho Santa Fe, CA (US)

(73) Assignees: Enchi Corporation, Wellesley Hills, MA (US); Dartmouth College, Hanover, NH (US); UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 14/361,948

(22) PCT Filed: Nov. 30, 2012

(86) PCT No.: PCT/US2012/067216
§ 371 (c)(1),
(2) Date: May 30, 2014

(87) PCT Pub. No.: WO2013/141905
PCT Pub. Date: Sep. 26, 2013

(65) Prior Publication Data

US 2014/0322783 A1 Oct. 30, 2014

Related U.S. Application Data

(60) Provisional application No. 61/565,261, filed on Nov. 30, 2011.

(51) Int. Cl.

| | |
|---|---|
| ***C12N 1/21*** | (2006.01) |
| ***C12N 9/02*** | (2006.01) |
| ***C12N 9/04*** | (2006.01) |
| ***C12N 15/53*** | (2006.01) |
| ***C12P 7/06*** | (2006.01) |
| ***C12N 15/74*** | (2006.01) |

(52) U.S. Cl.
CPC .............. *C12P 7/06* (2013.01); *C12N 9/0006* (2013.01); *C12N 9/0008* (2013.01); *C12N 15/74* (2013.01); *C12Y 101/01001* (2013.01); *C12Y 101/01002* (2013.01); *Y02E 50/17* (2013.01)

(58) Field of Classification Search
None
See application file for complete search history.

(56) References Cited

U.S. PATENT DOCUMENTS

2010/0297721 A1* 11/2010 Hogsett ................ C12N 9/0006 435/165
2011/0171709 A1 7/2011 Bardsley
2011/0287499 A1* 11/2011 Brown ................ C12N 9/0006 435/155
2013/0273555 A1* 10/2013 Sillers ..................... C12N 1/18 435/6.18

FOREIGN PATENT DOCUMENTS

EP 2 277 989 A1 1/2011
WO WO 2009111513 A1 * 9/2009 ............... C12N 1/20
WO WO 2010/010116 A2 1/2010
WO WO 2010/051527 A2 5/2010
WO WO-2010056805 A2 * 5/2010 ........... C12N 9/0006
WO WO 2013/141905 A2 9/2013

OTHER PUBLICATIONS

Machielsen et al., Production and characterization of a thermostable alcohol dehydrogenase that belongs to the aldo-keto reductase superfamily, App. Environ. Microbiol., 2006, 72, 233-238.*
Uniprot, Accession No. P0A9Q7, 2010, www.uniprot.org.*
Higashide et al., Metabolic engineering of Clostridium cellulolyticum for production of isobutanol from cellulose, Appl. Environ. Microbiol. Apr. 2011, 77, 2727-33.*
Shao et al., Mutant selection and phenotypic and genetic characterization of ethanol-tolerant strains of Clostridium thermocellum, Appl. Microbiol. Biotechnol., Aug. 2011, 92, 641-52.*
Chung et al., Direct conversion of plant biomass to ethanol by engineered Caldicellulosiruptor bescii, Proc. Natl. Acad. Sci. USA, 2014, 111, 8931-36.*
Brown et al., Mutant alcohol dehydrogenase leads to improved ethanol tolerance in Clostridium thermocellum, Proc. Natl. Acad. Sci., Aug. 2011, 108, 13752-57 and Supplemental Information.*
Blouzard et al., Modulation of cellulosome composition in Clostridium cellulolyticum, Proteomics, 2010, 20, 541-54.*
Shaw et al., End-product pathways in the xylose fermenting bacterium, Thermoanaerobacterium saccharolyticum, Enzyme Microbial Tech., 2008, 42, 453-58.*
GenBank, Accession No. EU313774.1, 2008, www.ncbi.nlm.nih.gov.*

(Continued)

*Primary Examiner* — Robert B Mondesi
*Assistant Examiner* — Todd M Epstein
(74) *Attorney, Agent, or Firm* — Sterne, Kessler, Goldstein & Fox P.L.L.C.

(57) ABSTRACT

The present invention provides for the manipulation of cofactor usage in a recombinant host cell to increase the formation of desirable products. In some embodiments, the invention provides for a recombinant microorganism comprising a mutation in one or more native enzymes such that their cofactor specificity is altered in such a way that overall cofactor usage in the cell is balanced for a specified pathway and there is an increase in a specific product formation within the cell. In some embodiments, endogenous enzymes are replaced by enzymes with an alternate cofactor specificity from a different species.

9 Claims, 5 Drawing Sheets

Specification includes a Sequence Listing.

(56) References Cited

OTHER PUBLICATIONS

Lynd et al., Fermentation of Cellulosic Substrates in Batch and Continuous Culture by Clostridium thermocellum, Appl. Environ. Microbiol., 1989, 55, 3131-39.*
Yao et al., Identification and overexpression of a bifunctional aldehyde/alcohol dehydrogenase responsibility for ethanol production in Thermoanaerobacer mathranii, J. Mol. Microbiol. Biotechnol., Oct. 2010, 19, 123-33.*
Taylor et al., Thermophilic ethanologenesis, Trends in Biotechnol., 2009, 27, 398-405.*
GenBank, Accession No. CAZ39599.1, 2010, www.ncbi.nlm.gov.*
Dai et al., Elucidating the contributions of multiple aldehyde/alcohol dehydrogenases to butanol and ethanol production in Clostridium acetobutylicum, Scientific Reports, 2016, 6, 28189.*
Uniprot, Accession No. A3DCI2, 2010, www.uniprot.org.*
Genbank, Accession No. CP000578.1, 2011, www.ncbi.nlm.nih.gov.*
Guedon et al., Improvement of Cellulolytic Properties of Clostridium cellulolyticum by Metabolic Engineering, Appl. Environ. Microbiol., 2002, 68, 53-58.*
Genbank, Accession No. ACA51670, 2008, www.ncbi.nlm.nih.gov.*
Argyros, D.A., et al., "High Ethanol Titers from Cellulose by Using Metabolically Engineered Thermophilic, Anaerobic Microbes." *Appl. Env. Microbiol.*77(23):8288-8294, American Society for Microbiology, United States (Dec. 2011).
Bastian, S., et al., "Engineered ketol-acid reductoisomerase and alcohol dehydrogenase enable anaerobic 2-methylpropan-1-ol production at theoretical yield in *Escherichia coli," Metabolic Engineering* 13:345-352, Elsevier Inc., United States (May 2011).
Bozzi, A., et al., "Structural and biochemical studies of alcohol dehydrogenase isozymes from *Kluyveromyces lactis," Biochimica et Biophysica Acta* 1339:133-142, Elsevier Science B.V., Netherlands (1997).
Brown, S.D., et al., "Mutant alcohol dehydrogenase leads to improved ethanol tolerance in *Clostridiutn thermocellum," Proc. Natl. Acad. Sci. U.S.A.* 108(33):13752-13757, National Academy of Sciences, United States (Aug. 2011).
Burdette, D.S., et al., "Cloning and expression of the gene encoding the *Thermoanaerobacter ethanolicus* 39E secondary-alcohol dehydrogenase and biochemical characterization of the enzyme," *Biochem. J.* 316:115-122, Portland Press on behalf of the Biochemical Society, England (1996).
Burdette, D. and Zeikus, J.G., "Purification of acetaldehyde dehydrogenase and alcohol dehydrogenases from *Thermoanaerobacter ethanolicus* 39E and characterization of the secondary-alcohol dehydrogenase (2° Adh) as a bifunctional alcohol dehydrogenase-acetyl-CoA reductive thioesterase," *Biochem. J.* 302:163-170, Portland Press on behalf of the Biochemical Society, England (1994).
Campbell, E., et al., "Broadening the Cofactor Specificity of a Thermostable Alcohol Dehydrogenase Using Rational Protein Design Introduces Novel Kinetic Transient Behavior," *Biotechnol. Bioeng.* 107(5):763-774, Wiley Periodicals, Inc., United States (Dec. 2010).
Conway, T., et al., "Cloning and Sequencing of the Alcohol Dehydrogenase II Gene from *Zymomonas mobilis," Journal of Bacteriology* 169(6):2591-2597, American Society for Microbiology. United States (1987).
Gibson, D.G., "Enzymatic Assembly of Overlapping DNA Fragments," *Methods in Enzymology* 498:349-361, Elsevier Inc., United States (2011).
Khoury, G.A., et al., "Computational design of *Candida boidinii* xylose reductase for altered cofactor specificity," *Protein Science* 18:2125-2138, Wiley-Blackwell and The Protein Society, United States (2009).
Kobayashi, K., et al., "Structure and Properties of Malic Enzyme from *Bacillus stearothermophilus," The Journal of Biological Chemistry* 264(6):3200-3205, The American Society for Biochemistry and Molecular Biology, Inc., United States (1989).
Madern, D., "The putative L-lactate dehydrogenase from *Methanococcus jannaschii* is an NADPH-dependent L-malate dehydrogenase," *Molecular Microbiology* 37(6):1515-1520, Blackwell Science Ltd., England (2000).
Matsushika, A., et al., "Bioethanol Production from Xylose by Recombinant *Saccaromyces cerevisiae* Expressing Xylose Reductase, $NADP^+$-dependent Xylitol Dehydrogenase, and Xylulokinase," *Journal of Bioscience and Bioengineering* 105(3):296-299, The Society for Biotechnology, Japan (2008).
Olson, D.G., et al., "Deletion of the Cel48S cellulase from *Clostridium thertnocellzan," Proc. Natl. Acacl Sci. U.S.A.* 107(41):17727-17732, National Academy of Sciences, United States (Oct. 2010).
Roberts, S.B., et al., "Genome-scale metabolic analysis of *Clostridium thermocellum* for bioethanol production," *BMC Systems Biology* 4(31):17 pages, BioMed Central Ltd., England (Mar. 2010).
Rydzak, T., et al., "Growth phase-dependant enzyme profile of pyruvate catabolism and end-product formation in *Clostridium thermocellum* ATCC 27405," *Journal of Biotechnology* 140:169-175, Elsevier Science B.V., Netherlands (2009).
Sakoda, H. and Imanaka, T., "Cloning and Sequencing of the Gene Coding for Alcohol Dehydrogenase of *Bacillus stearothermophilus* and Rational Shift of the Optimum pH," *Journal of Bacteriology* 174(4):1397-1402, American Society for Microbiology, United States (1992).
Sharp, P.M. and Li, W.H., "The codon adaptation index—a measure of directional synonymous codon usage bias, and its potential applications," *Nucleic Acids Research* 15(3):1281-1295, IRL Press Limited, England (1987).
Shaw, A.J. et al., "Metabolic engineering of a thermophilic bacterium to produce ethanol at high yield," *Proc. Natl. Acad. Sci. U.S.A.* 105(37):13769-13774, National Academy of Sciences, United States (2008).
Suwannarangsee, S., et al., "Characterization of alcohol dehydrogenase 1 of the thermotolerant methylotrophic yeast *Hansenula polymorpha," Appl Microbiol Biotechnol* 88:497-507, Springer-Verlag, Germany (Jul. 2010).
Wang, S., et al., "$NADP^+$ Reduction with Reduced Ferredoxin and $NADP^+$ Reduction with NADH are Coupled via an Electron-Bifurcating Enzyme Complex in *Clostridium kluyveri," Journal of Bacteriology* 192(19):5115-5123, American Society for Microbiology, United States (Oct. 2010).
Welch, M., et al., "Designing Genes for Successful Protein Expression," *Methods in Enzymolohgy* 498:43-66. Elsevier Inc., United States (2011).
Yao, S. and Mikkelsen, M.J., "Identification and Overexpression of a Bifunctional Aldehyde/Alcohol Dehydrogenase Responsible for Ethanol Production in *Thermoanaerobacter mathranii," J. Mol Microbiol Biotechnol* 19:123-133, S. Karger AG, United States (Oct. 2010).
Ying, X., et al., "Molecular characterization of the recombinant iron-containing alcohol dehydrogenase from the hypertherrnophilic Archaeon, *Thermococcus* strain ES1," *Extermophiles* 13:299-311, Springer, Japan (2009).
Accession No. U49975, NCBI Database, accessed at http://www.ncbi.nlm.nih.gov/nuccore/U49975, accessed on Sep. 24, 2014.
Accession No. M19485, NCBI Database, accessed at http://www.ncbi.nlm.nih.gov/nuccore/M19485, accessed on Sep. 24, 2014.
International Search Report for International Patent Application No. PCT/US2012/067216, European Patent Office, Rijswijk, Netherlands, dated Dec. 17, 2013.
International Preliminary Report on Patentability for International Patent Application No. PCT/US2012/067216, The International Bureau of WIPO, Geneva, Switzerland, dated Jun. 3, 2014.
Biwas R., et al., "Increase in Ethanol Yield via Elimination of Lactate Production in an Ethanol-Tolerant Mutant of *Clostridium thermocellum," PLOS ONE* 9(2):e86389, Public Library of Science, United States (2014).
Hon, S., et al., "Development of a plasmid-based expression system in *Clostridium thermocellum* and its use to screen heterologous expression of bifunctional alcohol dehydrogenases (adhEs)," *Metabolic Engineering Communications* 3:120-129, Elsevier, Netherlands (2016).

* cited by examiner

A

B

SEQUENCE LISTING

<160> NUMBER OF SEQ ID NOS: 61

<210> SEQ ID NO 1
<211> LENGTH: 1200
<212> TYPE: DNA
<213> ORGANISM: Moorella thermoacetica

<400> SEQUENCE: 1

```
atgtgggaaa caaaaataaa catcaacgaa gtccgggaaa tccgggctaa aacaaccgtc     60

tactttggag ttggagctat taaaaagatt gacgacatag ccagggaatt taaggaaaag    120

ggatacgata ggatcatcgt aataaccggc aagggggctt ataaagccac cggcgcgtgg    180

gaatatatag ttccggcctt aaataaaaac cagataacct atatccatta cgaccaggtg    240

acgcccaacc cgacggtaga ccaggttgac gaggcaacca aacaagcccg ggaattcggt    300

gcccgagccg tcctggccat cggcgggggt agccccattg atgccgctaa aagcgtagcc    360

gtcttgctct cctaccccga caaaaatgcc cgacagctct accagttaga atttacacct    420

gttaaggccg cacctatcat cgctattaat cttacccatg gtacggggac ggaagccgat    480

cgctttgccg ttgtcagcat ccctgaaaag gcatataaac ccgctattgc ctatgattgc    540

atttacccct tatattcaat tgacgacccg gccctcatgg taaaactgcc gtccgaccag    600

acagcttatg tctctgttga tgccctcaac catgtcgtcg aagcagccac cagcaaagta    660

gccagcccct atactattat cctggccaag gaaacggtac ggctcatcgc ccgatacctg    720

ccccaggccc tgtcccatcc ggcggatttg acggccaggt attatctcct ctatgcttcc    780

ctgattgccg gaatagcctt tgacaacggt ttgctccact tcacccacgc cctggaacac    840

cccctgagcg ccgtcaaacc ggagctcgcc cacggtctgg ggctgggtat gctgctgccg    900

gccgtagtca agcagattta cccggcaacc ccggaggtac tggcggagat actggagccc    960

attgttcccg atctcaaagg cgttcccggt gaagcagaaa aggctgccag cggggtggca   1020

aaatggcttg ccggagccgg tattaccatg aagctaaaag atgcgggctt tcaagcggaa   1080

gatatcgcca ggttaactga cctggccttt accaccccga gtctcgagct tctcctgagt   1140

atggccccgg taacggccga cagggaaagg gttaaggcaa tttaccagga cgccttttaa   1200
```

<210> SEQ ID NO 2
<211> LENGTH: 399
<212> TYPE: PRT
<213> ORGANISM: Moorella thermoacetica

<400> SEQUENCE: 2

```
Met Trp Glu Thr Lys Ile Asn Ile Asn Glu Val Arg Glu Ile Arg Ala
1               5                   10                  15

Lys Thr Thr Val Tyr Phe Gly Val Gly Ala Ile Lys Lys Ile Asp Asp
            20                  25                  30

Ile Ala Arg Glu Phe Lys Glu Lys Gly Tyr Asp Arg Ile Ile Val Ile
        35                  40                  45

Thr Gly Lys Gly Ala Tyr Lys Ala Thr Gly Ala Trp Glu Tyr Ile Val
    50                  55                  60

Pro Ala Leu Asn Lys Asn Gln Ile Thr Tyr Ile His Tyr Asp Gln Val
65                  70                  75                  80

Thr Pro Asn Pro Thr Val Asp Gln Val Asp Glu Ala Thr Lys Gln Ala
                85                  90                  95

Arg Glu Phe Gly Ala Arg Ala Val Leu Ala Ile Gly Gly Gly Ser Pro
            100                 105                 110
```

```
Ile Asp Ala Ala Lys Ser Val Ala Val Leu Leu Ser Tyr Pro Asp Lys
        115                 120                 125

Asn Ala Arg Gln Leu Tyr Gln Leu Glu Phe Thr Pro Val Lys Ala Ala
    130                 135                 140

Pro Ile Ile Ala Ile Asn Leu Thr His Gly Thr Gly Thr Glu Ala Asp
145                 150                 155                 160

Arg Phe Ala Val Val Ser Ile Pro Glu Lys Ala Tyr Lys Pro Ala Ile
                165                 170                 175

Ala Tyr Asp Cys Ile Tyr Pro Leu Tyr Ser Ile Asp Asp Pro Ala Leu
            180                 185                 190

Met Val Lys Leu Pro Ser Asp Gln Thr Ala Tyr Val Ser Val Asp Ala
        195                 200                 205

Leu Asn His Val Val Glu Ala Ala Thr Ser Lys Val Ala Ser Pro Tyr
    210                 215                 220

Thr Ile Ile Leu Ala Lys Glu Thr Val Arg Leu Ile Ala Arg Tyr Leu
225                 230                 235                 240

Pro Gln Ala Leu Ser His Pro Ala Asp Leu Thr Ala Arg Tyr Tyr Leu
                245                 250                 255

Leu Tyr Ala Ser Leu Ile Ala Gly Ile Ala Phe Asp Asn Gly Leu Leu
            260                 265                 270

His Phe Thr His Ala Leu Glu His Pro Leu Ser Ala Val Lys Pro Glu
        275                 280                 285

Leu Ala His Gly Leu Gly Leu Gly Met Leu Leu Pro Ala Val Val Lys
    290                 295                 300

Gln Ile Tyr Pro Ala Thr Pro Glu Val Leu Ala Glu Ile Leu Glu Pro
305                 310                 315                 320

Ile Val Pro Asp Leu Lys Gly Val Pro Gly Glu Ala Glu Lys Ala Ala
                325                 330                 335

Ser Gly Val Ala Lys Trp Leu Ala Gly Ala Gly Ile Thr Met Lys Leu
            340                 345                 350

Lys Asp Ala Gly Phe Gln Ala Glu Asp Ile Ala Arg Leu Thr Asp Leu
        355                 360                 365

Ala Phe Thr Thr Pro Ser Leu Glu Leu Leu Leu Ser Met Ala Pro Val
    370                 375                 380

Thr Ala Asp Arg Glu Arg Val Lys Ala Ile Tyr Gln Asp Ala Phe
385                 390                 395


<210> SEQ ID NO 3
<211> LENGTH: 1630
<212> TYPE: DNA
<213> ORGANISM: Thermoanaerobacter ethanolicus

<400> SEQUENCE: 3

tgaacaatag acaacccctt tctgtgatct tgttttttgc aaatgctatt ttatcacaag      60

agatttctct agttcttttt tacttaaaaa aaccctacga aattttaaac tatgtcgaat     120

aaattattga taatttttaa ctatgtgcta ttatattatt gcaaaaaatt taacaatcat     180

cgcgtaagct agttttcaca ttaatgactt acccagtatt ttaggaggtg tttaatgatg     240

aaaggttttg caatgctcag tatcggtaaa gttggctgga ttgagaagga aaagcctgct     300

cctggcccat ttgatgctat tgtaagacct ctagctgtgg cccccttgcac ttcggacatt     360

cataccgttt ttgaaggagc cattggcgaa agacataaca tgatactcgg tcacgaagct     420

gtaggtgaag tagttgaagt aggtagtgag gtaaaagatt ttaaacctgg tgatcgcgtt     480

gttgtgccag ctattacccc tgattggtgg acctctgaag tacaaagagg atatcaccag     540
```

```
cactccggtg gaatgctggc aggctggaaa ttttcgaatg taaaagatgg tgtttttggt    600
gaatttttc atgtgaatga tgctgatatg aatttagcac atctgcctaa agaaattcca    660
ttggaagctg cagttatgat tcccgatatg atgaccactg gttttcacgg agctgaactg    720
gcagatatag aattaggtgc gacggtagca gttttgggta ttggcccagt aggtcttatg    780
gcagtcgctg gtgccaaatt gcgtggagcc ggaagaatta ttgccgtagg cagtagacca    840
gtttgtgtag atgctgcaaa atactatgga gctactgata ttgtaaacta taaagatggt    900
cctatcgaaa gtcagattat gaatctaact gaaggcaaag gtgtcgatgc tgccatcatc    960
gctggaggaa atgctgacat tatggctaca gcagttaaga ttgttaaacc tggtggcacc   1020
atcgctaatg taaattattt tggcgaagga gaggttttgc ctgttcctcg tcttgaatgg   1080
ggttgcggca tggctcataa aactataaaa ggcgggctat gccccggtgg acgtctaaga   1140
atggaaagac tgattgacct tgttttttat aagcctgtcg atccttctaa gctcgtcact   1200
cacgttttcc agggatttga caatattgaa aaagccttta tgttgatgaa agacaaacca   1260
aaagacctaa tcaaacctgt tgtaatatta gcataaaaat ggggacttag tccattttta   1320
tgctaataag gctaaataca ctggtttttt tatatgacac atcggccagt aaactcttgg   1380
taaaaaaata acaaaaaata gttattttct taacattttt acgccattaa cacttgataa   1440
catcatcgaa gaagtaaata aacaactatt aaataaaaga agaaggagga ttatcatgtt   1500
caaaatttta gaaaaaagag aattggcacc ttccatcaag ttgtttgtaa tagaggcacc   1560
actagtagcc aaaaaagcaa ggccaggcca attcgttatg ctaaggataa aagaaggagg   1620
agaaagaatt                                                          1630
```

<210> SEQ ID NO 4
<211> LENGTH: 1404
<212> TYPE: DNA
<213> ORGANISM: T.saccharolyticum

<400> SEQUENCE: 4

```
atgaaagtta aagaggaaga tattgaagcg atcgtcaaaa aagtcttatc ggaatttaat     60
tttgaaaaaa atactaaaag tttcagagat tttggcgtat ttcaagatat gaatgatgct    120
attcgtgctg caaaagatgc ccagaaaaaa ttgagaaata tgtccatgga gtcgagagaa    180
aagattatac agaatataag aaaaaagatt atggagaata aaaaaatact tgcagagatg    240
ggcgtcagtg aaactggcat ggggaaagta gagcacaaaa taataaaaca tgagcttgta    300
gcacttaaga cacctggtac cgaagatata gtgacaacag catggtctgg cgataaggga    360
ctgacattgg ttgaaatggg gccatttggt gtaataggta cgattactcc ttcgacaaat    420
ccaagtgaaa ccgtcctttg caatagcata ggtatgatag ccgcaggtaa ttcagtcgta    480
tttaatccac atccaggtgc ggtaaatgta tctaattacg ctgtcaagtt agtaaatgaa    540
gcggtgatgg aagctggcgg ccctgagaat ttagtcgcat ctgttgaaaa acctacactt    600
gaaactggaa atattatgtt caagagtcct gatgtttcgc tattagtagc gacaggcgga    660
cctggtgtag taacatcggt tctctcatct ggcaaaaggg caataggagc aggagcagga    720
aatccaccag ttgtagttga tgaaacggca gatataaaaa aagctgcgaa agatatagtc    780
gatggtgcta catttgacaa caatttgcct tgtattgctg aaaaggaagt agtttctgta    840
gataaaataa cagatgaact gatttactac atgcaacaga atggctgcta caagattgag    900
gggcgagaaa ttgaaaagct cattgaactt gtattggatc acaaaggtgg caagataaca    960
```

```
ttaaacagga aatgggttgg caaagatgct catttaatac taaaagctat aggcatagat   1020

gctgatgaaa gcgtaaggtg cataattttt gaggcggaaa aagacaatcc gttagtggta   1080

gaagagctga tgatgcctat tttaggaata gtaagagcca aaaatgtaga tgaagcgata   1140

atgattgcga cagagttaga acatggcaat aggcattcag cacatatgca ttctaaaaac   1200

gttgataatt taacaaagtt tggaaaaata attgacactg ctatatttgt aaaaaatgct   1260

ccatcgtatg ccgcgttagg atatggtggt gaaggttatt gcacatttac gattgcaagc   1320

agaacaggtg aaggattgac atctgcaagg acttttacta aaagtcgtag atgtgtcttg   1380

gcagatggat tatcaataag atag                                           1404


<210> SEQ ID NO 5
<211> LENGTH: 467
<212> TYPE: PRT
<213> ORGANISM: T.saccharolyticum

<400> SEQUENCE: 5

Met Lys Val Lys Glu Glu Asp Ile Glu Ala Ile Val Lys Lys Val Leu
1               5                   10                  15

Ser Glu Phe Asn Phe Glu Lys Asn Thr Lys Ser Phe Arg Asp Phe Gly
            20                  25                  30

Val Phe Gln Asp Met Asn Asp Ala Ile Arg Ala Ala Lys Asp Ala Gln
        35                  40                  45

Lys Lys Leu Arg Asn Met Ser Met Glu Ser Arg Glu Lys Ile Ile Gln
    50                  55                  60

Asn Ile Arg Lys Lys Ile Met Glu Asn Lys Lys Ile Leu Ala Glu Met
65                  70                  75                  80

Gly Val Ser Glu Thr Gly Met Gly Lys Val Glu His Lys Ile Ile Lys
                85                  90                  95

His Glu Leu Val Ala Leu Lys Thr Pro Gly Thr Glu Asp Ile Val Thr
            100                 105                 110

Thr Ala Trp Ser Gly Asp Lys Gly Leu Thr Leu Val Glu Met Gly Pro
        115                 120                 125

Phe Gly Val Ile Gly Thr Ile Thr Pro Ser Thr Asn Pro Ser Glu Thr
    130                 135                 140

Val Leu Cys Asn Ser Ile Gly Met Ile Ala Ala Gly Asn Ser Val Val
145                 150                 155                 160

Phe Asn Pro His Pro Gly Ala Val Asn Val Ser Asn Tyr Ala Val Lys
                165                 170                 175

Leu Val Asn Glu Ala Val Met Glu Ala Gly Gly Pro Glu Asn Leu Val
            180                 185                 190

Ala Ser Val Glu Lys Pro Thr Leu Glu Thr Gly Asn Ile Met Phe Lys
        195                 200                 205

Ser Pro Asp Val Ser Leu Leu Val Ala Thr Gly Gly Pro Gly Val Val
    210                 215                 220

Thr Ser Val Leu Ser Ser Gly Lys Arg Ala Ile Gly Ala Gly Ala Gly
225                 230                 235                 240

Asn Pro Pro Val Val Val Asp Glu Thr Ala Asp Ile Lys Lys Ala Ala
                245                 250                 255

Lys Asp Ile Val Asp Gly Ala Thr Phe Asp Asn Asn Leu Pro Cys Ile
            260                 265                 270

Ala Glu Lys Glu Val Val Ser Val Asp Lys Ile Thr Asp Glu Leu Ile
        275                 280                 285

Tyr Tyr Met Gln Gln Asn Gly Cys Tyr Lys Ile Glu Gly Arg Glu Ile
```

```
    290                 295                 300

Glu Lys Leu Ile Glu Leu Val Leu Asp His Lys Gly Gly Lys Ile Thr
305                 310                 315                 320

Leu Asn Arg Lys Trp Val Gly Lys Asp Ala His Leu Ile Leu Lys Ala
                325                 330                 335

Ile Gly Ile Asp Ala Asp Glu Ser Val Arg Cys Ile Ile Phe Glu Ala
            340                 345                 350

Glu Lys Asp Asn Pro Leu Val Val Glu Glu Leu Met Met Pro Ile Leu
        355                 360                 365

Gly Ile Val Arg Ala Lys Asn Val Asp Glu Ala Ile Met Ile Ala Thr
    370                 375                 380

Glu Leu Glu His Gly Asn Arg His Ser Ala His Met His Ser Lys Asn
385                 390                 395                 400

Val Asp Asn Leu Thr Lys Phe Gly Lys Ile Ile Asp Thr Ala Ile Phe
                405                 410                 415

Val Lys Asn Ala Pro Ser Tyr Ala Ala Leu Gly Tyr Gly Gly Glu Gly
            420                 425                 430

Tyr Cys Thr Phe Thr Ile Ala Ser Arg Thr Gly Glu Gly Leu Thr Ser
        435                 440                 445

Ala Arg Thr Phe Thr Lys Ser Arg Arg Cys Val Leu Ala Asp Gly Leu
    450                 455                 460

Ser Ile Arg
465


<210> SEQ ID NO 6
<211> LENGTH: 2580
<212> TYPE: DNA
<213> ORGANISM: T.saccharolyticum

<400> SEQUENCE: 6

atggcaacga caaaaacgga attagacgtt cagaagcaga tagatctact tgtgtcaaga      60

gcacaagagg ctcagaaaaa attcatgtct tacacgcaag agcaaatcga cgcaatagtt     120

aaggcaatgg ctttagcagg cgttgacaaa cacgtagagc tggcaaagat ggcgtacgaa     180

gagacaaaaa tgggtgtata cgaagataag ataacaaaaa atctcttcgc aacagagtac     240

gtgtaccacg acataaaaaa tgaaaagact gtaggaatca taaacgagaa catagaagaa     300

aactacatgg aagtggcaga accgataggc gtaattgccg gtgtcacacc tgtcacaaac     360

ccaacatcta ccacgatgtt taaatgctta atatccataa agacgcgaaa tcctataata     420

ttcagcttcc atccaaaggc aataaagtgc agcatcgcag cagccaaagt gatgtatgaa     480

gctgcactaa aggcaggcgc acctgaagga tgcataggat ggatagaaac gccatcaatt     540

gaggccacac agcttctcat gacacatcca ggcgtatcgc tgatccttgc aacgggcggt     600

gcaggaatgg taaaagcggc atacagctca ggaaaaccgg cattaggcgt aggtcctggc     660

aatgtgccat gctacatcga aaaatcagca aacataaaga gggctgtatc ggatctcata     720

ctaagcaaga catttgacaa tggagtaata tgcgcatcag agcaggccgt aataatagac     780

gaggaaatag cagatgaagt caaaaagctt atgaaagaat acggctgcta cttcttaaac     840

aaagatgaaa taaagaagct tgagaaattt gcaattgatg agcaaagctg cgccatgagc     900

cctgcagtgg taggtcagcc agcggcgaag attgctgaaa tggcaggctt caaagtcccc     960

gaaggcacaa agatattagt ggcagagtac gaaggagtag gtccaaaata tcctctatca    1020

agggagaaac taagcccgat tcttgcttgc tacaccgtca aagactacaa tgaaggaatc    1080
```

```
aaaaagtgcg aggaaatgac tgaattcgga ggtttaggcc actctgctgt aatacactct   1140

gaaaatcaaa acgtcataaa tgaatttgca aggcgagtcc gcacaggaag acttatcgta   1200

aattcaccat catcacaggg agcaatagga gatatataca atacaaacac gccatcactt   1260

acattaggct gtggttctat gggaagaaac tcaacgacag acaatgtaag cgtcaagaac   1320

cttttgaata ttaagcgtgt cgtgataagg aaggatagaa tgaaatggtt caagattcca   1380

ccgaagattt actttgaaag cgggtcactc cagtacctgt gcaaagtcaa aagaaaaaaa   1440

gcgtttatcg tcacagatcc attcatggtt aagcttggct tcgtagacaa agtgacatat   1500

caattagaca aagcaaacat cgaatacgaa atattctcag aagtagagcc agatccatct   1560

gttgacacag tcatgaacgg cgtaaaaata atgaattcgt acaatcctga cttaataatc   1620

gctgtaggcg gtggctctgc aatagacgca gcaaagggaa tgtggctttt ctacgaatat   1680

cctgatacag agtttgaaac attgaggctt aaatttgcag acatcagaaa aagggcattt   1740

aagttcccag aacttggcaa aaaagcgcta ttcatcgcaa taccgacaac aagcggcaca   1800

ggctcagaag tgacagcatt tgccgtaata accgacaaaa agagaaacat caagtatcca   1860

ctggcagact acgaacttac acctgacata gccataatag atcctgacct tacaaagact   1920

gtaccgccat ctgtaacagc agacacaggc atggatgtgc tgacacacgc catagaagca   1980

tacgtatcag taatggcatc agactacaca gatgcactgg cggaaaaggc tataaagatc   2040

gtatttgaat acctgccaag ggcttataaa aacggcaatg atgaagaagc ccgcgaaaag   2100

atgcacaatg cttcctgcat ggctggtatg gcattcacaa atgcattctt aggaataaac   2160

cacagcatgg cacacatact gggcggaaag ttccacatac cacacggaag agcaaatgca   2220

atacttctgc cgtatgtaat aaggtacaat gcagaaaaac ctacaaagtt tgtggcattc   2280

ccacaatacg aatatccaaa agcagcagaa agatatgcgg aaatcgccaa attcttagga   2340

ctgcctgctt caactgttga agaaggcgta gaaagcttaa tagaagctat aaagaacctc   2400

atgaaagagc ttaacattcc gcttacactt aaagacgccg gcatcaacaa agaacagttt   2460

gaaaaagaaa tagaggaaat gtcagacatc gccttcaacg atcagtgcac agggacaaac   2520

ccgagaatgc ctctcacaaa agaaattgca gagatctaca gaaaagcata cggtgcatag   2580
```

<210> SEQ ID NO 7
<211> LENGTH: 859
<212> TYPE: PRT
<213> ORGANISM: T.saccharolyticum

<400> SEQUENCE: 7

```
Met Ala Thr Thr Lys Thr Glu Leu Asp Val Gln Lys Gln Ile Asp Leu
1               5                   10                  15

Leu Val Ser Arg Ala Gln Glu Ala Gln Lys Lys Phe Met Ser Tyr Thr
            20                  25                  30

Gln Glu Gln Ile Asp Ala Ile Val Lys Ala Met Ala Leu Ala Gly Val
        35                  40                  45

Asp Lys His Val Glu Leu Ala Lys Met Ala Tyr Glu Glu Thr Lys Met
    50                  55                  60

Gly Val Tyr Glu Asp Lys Ile Thr Lys Asn Leu Phe Ala Thr Glu Tyr
65                  70                  75                  80

Val Tyr His Asp Ile Lys Asn Glu Lys Thr Val Gly Ile Ile Asn Glu
                85                  90                  95

Asn Ile Glu Glu Asn Tyr Met Glu Val Ala Glu Pro Ile Gly Val Ile
            100                 105                 110
```

```
Ala Gly Val Thr Pro Val Thr Asn Pro Thr Ser Thr Thr Met Phe Lys
        115                 120                 125

Cys Leu Ile Ser Ile Lys Thr Arg Asn Pro Ile Ile Phe Ser Phe His
    130                 135                 140

Pro Lys Ala Ile Lys Cys Ser Ile Ala Ala Ala Lys Val Met Tyr Glu
145                 150                 155                 160

Ala Ala Leu Lys Ala Gly Ala Pro Glu Gly Cys Ile Gly Trp Ile Glu
                165                 170                 175

Thr Pro Ser Ile Glu Ala Thr Gln Leu Leu Met Thr His Pro Gly Val
            180                 185                 190

Ser Leu Ile Leu Ala Thr Gly Gly Ala Gly Met Val Lys Ala Ala Tyr
        195                 200                 205

Ser Ser Gly Lys Pro Ala Leu Gly Val Gly Pro Gly Asn Val Pro Cys
    210                 215                 220

Tyr Ile Glu Lys Ser Ala Asn Ile Lys Arg Ala Val Ser Asp Leu Ile
225                 230                 235                 240

Leu Ser Lys Thr Phe Asp Asn Gly Val Ile Cys Ala Ser Glu Gln Ala
                245                 250                 255

Val Ile Ile Asp Glu Glu Ile Ala Asp Glu Val Lys Lys Leu Met Lys
            260                 265                 270

Glu Tyr Gly Cys Tyr Phe Leu Asn Lys Asp Glu Ile Lys Lys Leu Glu
        275                 280                 285

Lys Phe Ala Ile Asp Glu Gln Ser Cys Ala Met Ser Pro Ala Val Val
    290                 295                 300

Gly Gln Pro Ala Ala Lys Ile Ala Glu Met Ala Gly Phe Lys Val Pro
305                 310                 315                 320

Glu Gly Thr Lys Ile Leu Val Ala Glu Tyr Glu Gly Val Gly Pro Lys
                325                 330                 335

Tyr Pro Leu Ser Arg Glu Lys Leu Ser Pro Ile Leu Ala Cys Tyr Thr
            340                 345                 350

Val Lys Asp Tyr Asn Glu Gly Ile Lys Lys Cys Glu Glu Met Thr Glu
        355                 360                 365

Phe Gly Gly Leu Gly His Ser Ala Val Ile His Ser Glu Asn Gln Asn
    370                 375                 380

Val Ile Asn Glu Phe Ala Arg Arg Val Arg Thr Gly Arg Leu Ile Val
385                 390                 395                 400

Asn Ser Pro Ser Ser Gln Gly Ala Ile Gly Asp Ile Tyr Asn Thr Asn
                405                 410                 415

Thr Pro Ser Leu Thr Leu Gly Cys Gly Ser Met Gly Arg Asn Ser Thr
            420                 425                 430

Thr Asp Asn Val Ser Val Lys Asn Leu Leu Asn Ile Lys Arg Val Val
        435                 440                 445

Ile Arg Lys Asp Arg Met Lys Trp Phe Lys Ile Pro Pro Lys Ile Tyr
    450                 455                 460

Phe Glu Ser Gly Ser Leu Gln Tyr Leu Cys Lys Val Lys Arg Lys Lys
465                 470                 475                 480

Ala Phe Ile Val Thr Asp Pro Phe Met Val Lys Leu Gly Phe Val Asp
                485                 490                 495

Lys Val Thr Tyr Gln Leu Asp Lys Ala Asn Ile Glu Tyr Glu Ile Phe
            500                 505                 510

Ser Glu Val Glu Pro Asp Pro Ser Val Asp Thr Val Met Asn Gly Val
        515                 520                 525

Lys Ile Met Asn Ser Tyr Asn Pro Asp Leu Ile Ile Ala Val Gly Gly
```

```
    530                 535                 540

Gly Ser Ala Ile Asp Ala Ala Lys Gly Met Trp Leu Phe Tyr Glu Tyr
545                 550                 555                 560

Pro Asp Thr Glu Phe Glu Thr Leu Arg Leu Lys Phe Ala Asp Ile Arg
                565                 570                 575

Lys Arg Ala Phe Lys Phe Pro Glu Leu Gly Lys Lys Ala Leu Phe Ile
            580                 585                 590

Ala Ile Pro Thr Thr Ser Gly Thr Gly Ser Glu Val Thr Ala Phe Ala
        595                 600                 605

Val Ile Thr Asp Lys Lys Arg Asn Ile Lys Tyr Pro Leu Ala Asp Tyr
    610                 615                 620

Glu Leu Thr Pro Asp Ile Ala Ile Ile Asp Pro Asp Leu Thr Lys Thr
625                 630                 635                 640

Val Pro Pro Ser Val Thr Ala Asp Thr Gly Met Asp Val Leu Thr His
                645                 650                 655

Ala Ile Glu Ala Tyr Val Ser Val Met Ala Ser Asp Tyr Thr Asp Ala
            660                 665                 670

Leu Ala Glu Lys Ala Ile Lys Ile Val Phe Glu Tyr Leu Pro Arg Ala
        675                 680                 685

Tyr Lys Asn Gly Asn Asp Glu Glu Ala Arg Glu Lys Met His Asn Ala
    690                 695                 700

Ser Cys Met Ala Gly Met Ala Phe Thr Asn Ala Phe Leu Gly Ile Asn
705                 710                 715                 720

His Ser Met Ala His Ile Leu Gly Gly Lys Phe His Ile Pro His Gly
                725                 730                 735

Arg Ala Asn Ala Ile Leu Leu Pro Tyr Val Ile Arg Tyr Asn Ala Glu
            740                 745                 750

Lys Pro Thr Lys Phe Val Ala Phe Pro Gln Tyr Glu Tyr Pro Lys Ala
        755                 760                 765

Ala Glu Arg Tyr Ala Glu Ile Ala Lys Phe Leu Gly Leu Pro Ala Ser
    770                 775                 780

Thr Val Glu Glu Gly Val Glu Ser Leu Ile Glu Ala Ile Lys Asn Leu
785                 790                 795                 800

Met Lys Glu Leu Asn Ile Pro Leu Thr Leu Lys Asp Ala Gly Ile Asn
                805                 810                 815

Lys Glu Gln Phe Glu Lys Glu Ile Glu Glu Met Ser Asp Ile Ala Phe
            820                 825                 830

Asn Asp Gln Cys Thr Gly Thr Asn Pro Arg Met Pro Leu Thr Lys Glu
        835                 840                 845

Ile Ala Glu Ile Tyr Arg Lys Ala Tyr Gly Ala
    850                 855


<210> SEQ ID NO 8
<211> LENGTH: 2580
<212> TYPE: DNA
<213> ORGANISM: T.saccharolyticum

<400> SEQUENCE: 8

atggcaacga caaaaacgga attagacgtt cagaagcaga tagatctact tgtgtcaaga      60

gcacaagagg ctcagaaaaa attcatgtct tacacgcaag agcaaatcga cgcaatagtt     120

aaggcaatgg ctttagcagg cgttgacaaa cacgtagagc tggcaaagat ggcgtacgaa     180

gagacaaaaa tgggtgtata cgaagataag ataacaaaaa atctcttcgc aacagagtac     240

gtgtaccacg acataaaaaa tgaaaagact gtaggaatca taaacgagaa catagaagaa     300
```

```
aactacatgg aagtggcaga accgataggc gtaattgccg gtgtcacacc tgtcacaaac    360
ccaacatcta ccacgatgtt taaatgctta atatccataa agacgcgaaa tcctataata    420
ttcagcttcc atccaaaggc aataaagtgc agcatcgcag cagccaaagt gatgtatgaa    480
gctgcactaa aggcaggcgc acctgaagga tgcataggat ggatagaaac gccatcaatt    540
gaggccacac agcttctcat gacacatcca ggcgtatcgc tgatccttgc aacgggcggt    600
gcaggaatgg taaaagcggc atacagctca ggaaaaccgg cattaggcgt aggtcctggc    660
aatgtgccat gctacatcga aaaatcagca aacataaaga gggctgtatc ggatctcata    720
ctaagcaaga catttgacaa tggagtaata tgcgcatcag agcaggccgt aataatagac    780
gaggaaatag cagatgaagt caaaaagctt atgaaagaat acggctgcta cttcttaaac    840
aaagatgaaa taaagaagct tgagaaattt gcaattgatg agcaaagctg cgccatgagc    900
cctgcagtgg taggtcagcc agcggcgaag attgctgaaa tggcaggctt caaagtcccc    960
gaaggcacaa agatattagt ggcagagtac gaaggagtag gtccaaaata tcctctatca   1020
agggagaaac taagcccgat tcttgcttgc tacaccgtca aagactacaa tgaaggaatc   1080
aaaaagtgcg aggaaatgac tgaattcgga ggtttaggcc actctgctgt aatacactct   1140
gaaaatcaaa acgtcataaa tgaatttgca aggcgagtcc gcacaggaag acttatcgta   1200
aattcaccat catcacaggg agcaatagga gatatataca atacaaacac gccatcactt   1260
acattaggct gtggttctat gggaagaaac tcaacgacag acaatgtaag cgtcaagaac   1320
cttttgaata ttaagcgtgt cgtgataagg aatgatagaa tgaaatggtt caagattcca   1380
ccgaagattt actttgaaag cggtcactc cagtacctgt gcaaagtcaa aagaaaaaaa   1440
gcgtttatcg tcacagatcc attcatggtt aagcttggct tcgtagacaa agtgacatat   1500
caattagaca aagcaaacat cgaatacgaa atattctcag aagtagagcc agatccatct   1560
gttgacacag tcatgaacgg cgtaaaaata atgaattcgt acaatcctga cttaataatc   1620
gctgtaggcg gtggctctgc aatagacgca gcaaagggaa tgtggctttt ctacgaatat   1680
cctgatacag agtttgaaac attgaggctt aaatttgcag acatcagaaa aagggcattt   1740
aagttcccag aacttggcaa aaaagcgcta ttcatcgcaa taccgacaac aagcggcaca   1800
ggctcagaag tgacagcatt tgccgtaata accgacaaaa agagaaacat caagtatcca   1860
ctggcagact acgaacttac acctgacata gccataatag atcctgacct tacaaagact   1920
gtaccgccat ctgtaacagc agacacaggc atggatgtgc tgacacacgc catagaagca   1980
tacgtatcag taatggcatc agactacaca gatgcactgg cggaaaaggc tataaagatc   2040
gtatttgaat acctgccaag ggcttataaa aacggcaatg atgaagaagc ccgcgaaaag   2100
atgcacaatg cttcctgcat ggctggtatg gcattcacaa atgcattctt aggaataaac   2160
cacagcatgg cacacatact gggcggaaag ttccacatac cacacggaag agcaaatgca   2220
atacttctgc cgtatgtaat aaggtacaat gcagaaaaac ctacaaagtt tgtggcattc   2280
ccacaatacg aatatccaaa agcagcagaa agatatgcgg aaatcgccaa attcttagga   2340
ctgcctgctt caactgttga agaaggcgta gaaagcttaa tagaagctat aaagaacctc   2400
atgaaagagc ttaacattcc gcttacactt aaagacgccg gcatcaacaa agaacagttt   2460
gaaaaagaaa tagaggaaat gtcagacatc gccttcaacg atcagtgcac agggacaaac   2520
ccgagaatgc ctctcacaaa agaaattgca gagatctaca gaaaagcata cggtgcatag   2580
```

<210> SEQ ID NO 9

```
<211> LENGTH: 859
<212> TYPE: PRT
<213> ORGANISM: T.saccharolyticum

<400> SEQUENCE: 9

Met Ala Thr Thr Lys Thr Glu Leu Asp Val Gln Lys Gln Ile Asp Leu
1               5                   10                  15

Leu Val Ser Arg Ala Gln Glu Ala Gln Lys Lys Phe Met Ser Tyr Thr
            20                  25                  30

Gln Glu Gln Ile Asp Ala Ile Val Lys Ala Met Ala Leu Ala Gly Val
        35                  40                  45

Asp Lys His Val Glu Leu Ala Lys Met Ala Tyr Glu Glu Thr Lys Met
    50                  55                  60

Gly Val Tyr Glu Asp Lys Ile Thr Lys Asn Leu Phe Ala Thr Glu Tyr
65                  70                  75                  80

Val Tyr His Asp Ile Lys Asn Glu Lys Thr Val Gly Ile Ile Asn Glu
                85                  90                  95

Asn Ile Glu Glu Asn Tyr Met Glu Val Ala Glu Pro Ile Gly Val Ile
            100                 105                 110

Ala Gly Val Thr Pro Val Thr Asn Pro Thr Ser Thr Thr Met Phe Lys
        115                 120                 125

Cys Leu Ile Ser Ile Lys Thr Arg Asn Pro Ile Ile Phe Ser Phe His
    130                 135                 140

Pro Lys Ala Ile Lys Cys Ser Ile Ala Ala Ala Lys Val Met Tyr Glu
145                 150                 155                 160

Ala Ala Leu Lys Ala Gly Ala Pro Glu Gly Cys Ile Gly Trp Ile Glu
                165                 170                 175

Thr Pro Ser Ile Glu Ala Thr Gln Leu Leu Met Thr His Pro Gly Val
            180                 185                 190

Ser Leu Ile Leu Ala Thr Gly Gly Ala Gly Met Val Lys Ala Ala Tyr
        195                 200                 205

Ser Ser Gly Lys Pro Ala Leu Gly Val Gly Pro Gly Asn Val Pro Cys
    210                 215                 220

Tyr Ile Glu Lys Ser Ala Asn Ile Lys Arg Ala Val Ser Asp Leu Ile
225                 230                 235                 240

Leu Ser Lys Thr Phe Asp Asn Gly Val Ile Cys Ala Ser Glu Gln Ala
                245                 250                 255

Val Ile Ile Asp Glu Glu Ile Ala Asp Glu Val Lys Lys Leu Met Lys
            260                 265                 270

Glu Tyr Gly Cys Tyr Phe Leu Asn Lys Asp Glu Ile Lys Lys Leu Glu
        275                 280                 285

Lys Phe Ala Ile Asp Glu Gln Ser Cys Ala Met Ser Pro Ala Val Val
    290                 295                 300

Gly Gln Pro Ala Ala Lys Ile Ala Glu Met Ala Gly Phe Lys Val Pro
305                 310                 315                 320

Glu Gly Thr Lys Ile Leu Val Ala Glu Tyr Glu Gly Val Gly Pro Lys
                325                 330                 335

Tyr Pro Leu Ser Arg Glu Lys Leu Ser Pro Ile Leu Ala Cys Tyr Thr
            340                 345                 350

Val Lys Asp Tyr Asn Glu Gly Ile Lys Lys Cys Glu Glu Met Thr Glu
        355                 360                 365

Phe Gly Gly Leu Gly His Ser Ala Val Ile His Ser Glu Asn Gln Asn
    370                 375                 380

Val Ile Asn Glu Phe Ala Arg Arg Val Arg Thr Gly Arg Leu Ile Val
```

```
385                 390                 395                 400

Asn Ser Pro Ser Ser Gln Gly Ala Ile Gly Asp Ile Tyr Asn Thr Asn
                405                 410                 415

Thr Pro Ser Leu Thr Leu Gly Cys Gly Ser Met Gly Arg Asn Ser Thr
            420                 425                 430

Thr Asp Asn Val Ser Val Lys Asn Leu Leu Asn Ile Lys Arg Val Val
        435                 440                 445

Ile Arg Asn Asp Arg Met Lys Trp Phe Lys Ile Pro Pro Lys Ile Tyr
    450                 455                 460

Phe Glu Ser Gly Ser Leu Gln Tyr Leu Cys Lys Val Lys Arg Lys Lys
465                 470                 475                 480

Ala Phe Ile Val Thr Asp Pro Phe Met Val Lys Leu Gly Phe Val Asp
                485                 490                 495

Lys Val Thr Tyr Gln Leu Asp Lys Ala Asn Ile Glu Tyr Glu Ile Phe
            500                 505                 510

Ser Glu Val Glu Pro Asp Pro Ser Val Asp Thr Val Met Asn Gly Val
        515                 520                 525

Lys Ile Met Asn Ser Tyr Asn Pro Asp Leu Ile Ile Ala Val Gly Gly
    530                 535                 540

Gly Ser Ala Ile Asp Ala Ala Lys Gly Met Trp Leu Phe Tyr Glu Tyr
545                 550                 555                 560

Pro Asp Thr Glu Phe Glu Thr Leu Arg Leu Lys Phe Ala Asp Ile Arg
                565                 570                 575

Lys Arg Ala Phe Lys Phe Pro Glu Leu Gly Lys Lys Ala Leu Phe Ile
            580                 585                 590

Ala Ile Pro Thr Thr Ser Gly Thr Gly Ser Glu Val Thr Ala Phe Ala
        595                 600                 605

Val Ile Thr Asp Lys Lys Arg Asn Ile Lys Tyr Pro Leu Ala Asp Tyr
    610                 615                 620

Glu Leu Thr Pro Asp Ile Ala Ile Ile Asp Pro Asp Leu Thr Lys Thr
625                 630                 635                 640

Val Pro Pro Ser Val Thr Ala Asp Thr Gly Met Asp Val Leu Thr His
                645                 650                 655

Ala Ile Glu Ala Tyr Val Ser Val Met Ala Ser Asp Tyr Thr Asp Ala
            660                 665                 670

Leu Ala Glu Lys Ala Ile Lys Ile Val Phe Glu Tyr Leu Pro Arg Ala
        675                 680                 685

Tyr Lys Asn Gly Asn Asp Glu Glu Ala Arg Glu Lys Met His Asn Ala
    690                 695                 700

Ser Cys Met Ala Gly Met Ala Phe Thr Asn Ala Phe Leu Gly Ile Asn
705                 710                 715                 720

His Ser Met Ala His Ile Leu Gly Gly Lys Phe His Ile Pro His Gly
                725                 730                 735

Arg Ala Asn Ala Ile Leu Leu Pro Tyr Val Ile Arg Tyr Asn Ala Glu
            740                 745                 750

Lys Pro Thr Lys Phe Val Ala Phe Pro Gln Tyr Glu Tyr Pro Lys Ala
        755                 760                 765

Ala Glu Arg Tyr Ala Glu Ile Ala Lys Phe Leu Gly Leu Pro Ala Ser
    770                 775                 780

Thr Val Glu Glu Gly Val Glu Ser Leu Ile Glu Ala Ile Lys Asn Leu
785                 790                 795                 800

Met Lys Glu Leu Asn Ile Pro Leu Thr Leu Lys Asp Ala Gly Ile Asn
                805                 810                 815
```

```
Lys Glu Gln Phe Glu Lys Glu Ile Glu Glu Met Ser Asp Ile Ala Phe
            820                 825                 830

Asn Asp Gln Cys Thr Gly Thr Asn Pro Arg Met Pro Leu Thr Lys Glu
        835                 840                 845

Ile Ala Glu Ile Tyr Arg Lys Ala Tyr Gly Ala
    850                 855
```

<210> SEQ ID NO 10
<211> LENGTH: 2580
<212> TYPE: DNA
<213> ORGANISM: T.saccharolyticum

<400> SEQUENCE: 10

```
atggcaacga caaaaacgga attagacgtt cagaagcaga tagatctact tgtgtcaaga     60
gcacaagagg ctcagaaaaa attcatgtct tacacgcaag agcaaatcga cgcaatagtt    120
aaggcaatgg ctttagcagg cgttgacaaa cacgtagagc tggcaaagat ggcgtacgaa    180
gagacaaaaa tgggtgtata cgaagataag ataacaaaaa atctcttcgc aacagagtac    240
gtgtaccacg acataaaaaa tgaaaagact gtaggaatca taaacgagaa catagaagaa    300
aactacatgg aagtggcaga accgataggc gtaattgccg gtgtcacacc tgtcacaaac    360
ccaacatcta ccacgatgtt taaatgctta atatccataa agacgcgaaa tcctataata    420
ttcagcttcc atccaaaggc aataaagtgc agcatcgcag cagccaaagt gatgtatgaa    480
gctgcactaa aggcaggcgc acctgaagga tgcataggat ggatagaaac gccatcaatt    540
gaggccacac agcttctcat gacacatcca ggcgtatcgc tgatccttgc aacgggcggt    600
gcaggaatgg taaaagcggc atacagctca ggaaaaccgg cattaggcgt aggtcctggc    660
aatgtgccat gctacatcga aaaatcagca aacataaaga gggctgtatc ggatctcata    720
ctaagcaaga catttgacaa tggagtaata tgcgcatcag agcaggccgt aataatagac    780
gaggaaatag cagatgaagt caaaaagctt atgaaagaat acggctgcta cttcttaaac    840
aaagatgaaa taaagaagct tgagaaattt gcaattgatg agcaaagctg cgccatgagc    900
cctgcagtgg taggtcagcc agcggcgaag attgctgaaa tggcaggctt caaagtcccc    960
gaaggcacaa agatattagt ggcagagtac gaaggagtag gtccaaaata tcctctatca   1020
agggagaaac taagcccgat tcttgcttgc tacaccgtca aagactacaa tgaaggaatc   1080
aaaaagtgcg aggaaatgac tgaattcgga ggtttaggcc actctgctgt aatacactct   1140
gaaaatcaaa acgtcataaa tgaatttgca aggcgagtcc gcacaggaag acttatcgta   1200
aattcaccat catcacaggg agcaatagga gatatataca atacaaacac gccatcactt   1260
acattaggct gtggttctat gggaagaaac tcaacgacag acaatgtaag cgtcaagaac   1320
cttttgaata ttaagcgtgt cgtgataagg aaggatagaa tgaaatggtt caagattcca   1380
ccgaagattt actttgaaag cgggtcactc cagtacctgt gcaaagtcaa aagaaaaaaa   1440
gcgtttatcg tcacagatcc attcatggtt aagcttggct tcgtagacaa agtgacatat   1500
caattagaca aagcaaacat cgaatacgaa atattctcag aagtagagcc agatccatct   1560
gttgacacag tcatgaacgg cgtaaaaata atgaattcgt acaatcctga cttaataatc   1620
gctgtaggcg gtggctctgc aatagacgca gcaaagggaa tgtggctttt ctacgaatat   1680
cctgatacag agtttgaaac attgaggctt aaatttgcag acatcagaaa aagggcattt   1740
aagttcccag aacttggcaa aaaagcgcta ttcatcgcaa taccgacaac aagcggcaca   1800
ggcttagaag tgacagcatt tgccgtaata accgacaaaa agagaaacat caagtatcca   1860
```

```
ctggcagact acgaacttac acctgacata gccataatag atcctgacct tacaaagact   1920

gtaccgccat ctgtaacagc agacacaggc atggatgtgc tgacacacgc catagaagca   1980

tacgtatcag taatggcatc agactacaca gatgcactgg cggaaaaggc tataaagatc   2040

gtatttgaat acctgccaag ggcttataaa aacggcaatg atgaagaagc ccgcgaaaag   2100

atgcacaatg cttcctgcat ggctggtatg gcattcacaa atgcattctt aggaataaac   2160

cacagcatgg cacacatact gggcggaaag ttccacatac cacacggaag agcaaatgca   2220

atacttctgc cgtatgtaat aaggtacaat gcagaaaaac ctacaaagtt tgtggcattc   2280

ccacaatacg aatatccaaa agcagcagaa agatatgcgg aaatcgccaa attcttagga   2340

ctgcctgctt caactgttga agaaggcgta gaaagcttaa tagaagctat aaagaacctc   2400

atgaaagagc ttaacattcc gcttacactt aaagacgccg gcatcaacaa agaacagttt   2460

gaaaaagaaa tagaggaaat gtcagacatc gccttcaacg atcagtgcac agggacaaac   2520

ccgagaatgc ctctcacaaa agaaattgca gagatctaca gaaaagcata cggtgcatag   2580


<210> SEQ ID NO 11
<211> LENGTH: 859
<212> TYPE: PRT
<213> ORGANISM: T.saccharolyticum

<400> SEQUENCE: 11

Met Ala Thr Thr Lys Thr Glu Leu Asp Val Gln Lys Gln Ile Asp Leu
1               5                   10                  15

Leu Val Ser Arg Ala Gln Glu Ala Gln Lys Lys Phe Met Ser Tyr Thr
            20                  25                  30

Gln Glu Gln Ile Asp Ala Ile Val Lys Ala Met Ala Leu Ala Gly Val
        35                  40                  45

Asp Lys His Val Glu Leu Ala Lys Met Ala Tyr Glu Glu Thr Lys Met
    50                  55                  60

Gly Val Tyr Glu Asp Lys Ile Thr Lys Asn Leu Phe Ala Thr Glu Tyr
65                  70                  75                  80

Val Tyr His Asp Ile Lys Asn Glu Lys Thr Val Gly Ile Ile Asn Glu
                85                  90                  95

Asn Ile Glu Glu Asn Tyr Met Glu Val Ala Glu Pro Ile Gly Val Ile
            100                 105                 110

Ala Gly Val Thr Pro Val Thr Asn Pro Thr Ser Thr Thr Met Phe Lys
        115                 120                 125

Cys Leu Ile Ser Ile Lys Thr Arg Asn Pro Ile Ile Phe Ser Phe His
    130                 135                 140

Pro Lys Ala Ile Lys Cys Ser Ile Ala Ala Ala Lys Val Met Tyr Glu
145                 150                 155                 160

Ala Ala Leu Lys Ala Gly Ala Pro Glu Gly Cys Ile Gly Trp Ile Glu
                165                 170                 175

Thr Pro Ser Ile Glu Ala Thr Gln Leu Leu Met Thr His Pro Gly Val
            180                 185                 190

Ser Leu Ile Leu Ala Thr Gly Gly Ala Gly Met Val Lys Ala Ala Tyr
        195                 200                 205

Ser Ser Gly Lys Pro Ala Leu Gly Val Gly Pro Gly Asn Val Pro Cys
    210                 215                 220

Tyr Ile Glu Lys Ser Ala Asn Ile Lys Arg Ala Val Ser Asp Leu Ile
225                 230                 235                 240

Leu Ser Lys Thr Phe Asp Asn Gly Val Ile Cys Ala Ser Glu Gln Ala
```

```
                245                 250                 255

Val Ile Ile Asp Glu Glu Ile Ala Asp Glu Val Lys Lys Leu Met Lys
            260                 265                 270

Glu Tyr Gly Cys Tyr Phe Leu Asn Lys Asp Glu Ile Lys Lys Leu Glu
        275                 280                 285

Lys Phe Ala Ile Asp Glu Gln Ser Cys Ala Met Ser Pro Ala Val Val
    290                 295                 300

Gly Gln Pro Ala Ala Lys Ile Ala Glu Met Ala Gly Phe Lys Val Pro
305                 310                 315                 320

Glu Gly Thr Lys Ile Leu Val Ala Glu Tyr Glu Gly Val Gly Pro Lys
                325                 330                 335

Tyr Pro Leu Ser Arg Glu Lys Leu Ser Pro Ile Leu Ala Cys Tyr Thr
            340                 345                 350

Val Lys Asp Tyr Asn Glu Gly Ile Lys Lys Cys Glu Glu Met Thr Glu
        355                 360                 365

Phe Gly Gly Leu Gly His Ser Ala Val Ile His Ser Glu Asn Gln Asn
    370                 375                 380

Val Ile Asn Glu Phe Ala Arg Arg Val Arg Thr Gly Arg Leu Ile Val
385                 390                 395                 400

Asn Ser Pro Ser Ser Gln Gly Ala Ile Gly Asp Ile Tyr Asn Thr Asn
                405                 410                 415

Thr Pro Ser Leu Thr Leu Gly Cys Gly Ser Met Gly Arg Asn Ser Thr
            420                 425                 430

Thr Asp Asn Val Ser Val Lys Asn Leu Leu Asn Ile Lys Arg Val Val
        435                 440                 445

Ile Arg Lys Asp Arg Met Lys Trp Phe Lys Ile Pro Pro Lys Ile Tyr
    450                 455                 460

Phe Glu Ser Gly Ser Leu Gln Tyr Leu Cys Lys Val Lys Arg Lys Lys
465                 470                 475                 480

Ala Phe Ile Val Thr Asp Pro Phe Met Val Lys Leu Gly Phe Val Asp
                485                 490                 495

Lys Val Thr Tyr Gln Leu Asp Lys Ala Asn Ile Glu Tyr Glu Ile Phe
            500                 505                 510

Ser Glu Val Glu Pro Asp Pro Ser Val Asp Thr Val Met Asn Gly Val
        515                 520                 525

Lys Ile Met Asn Ser Tyr Asn Pro Asp Leu Ile Ile Ala Val Gly Gly
    530                 535                 540

Gly Ser Ala Ile Asp Ala Ala Lys Gly Met Trp Leu Phe Tyr Glu Tyr
545                 550                 555                 560

Pro Asp Thr Glu Phe Glu Thr Leu Arg Leu Lys Phe Ala Asp Ile Arg
                565                 570                 575

Lys Arg Ala Phe Lys Phe Pro Glu Leu Gly Lys Lys Ala Leu Phe Ile
            580                 585                 590

Ala Ile Pro Thr Thr Ser Gly Thr Gly Leu Glu Val Thr Ala Phe Ala
        595                 600                 605

Val Ile Thr Asp Lys Lys Arg Asn Ile Lys Tyr Pro Leu Ala Asp Tyr
    610                 615                 620

Glu Leu Thr Pro Asp Ile Ala Ile Ile Asp Pro Asp Leu Thr Lys Thr
625                 630                 635                 640

Val Pro Pro Ser Val Thr Ala Asp Thr Gly Met Asp Val Leu Thr His
                645                 650                 655

Ala Ile Glu Ala Tyr Val Ser Val Met Ala Ser Asp Tyr Thr Asp Ala
            660                 665                 670
```

```
Leu Ala Glu Lys Ala Ile Lys Ile Val Phe Glu Tyr Leu Pro Arg Ala
        675                 680                 685

Tyr Lys Asn Gly Asn Asp Glu Glu Ala Arg Glu Lys Met His Asn Ala
    690                 695                 700

Ser Cys Met Ala Gly Met Ala Phe Thr Asn Ala Phe Leu Gly Ile Asn
705                 710                 715                 720

His Ser Met Ala His Ile Leu Gly Gly Lys Phe His Ile Pro His Gly
                725                 730                 735

Arg Ala Asn Ala Ile Leu Leu Pro Tyr Val Ile Arg Tyr Asn Ala Glu
            740                 745                 750

Lys Pro Thr Lys Phe Val Ala Phe Pro Gln Tyr Glu Tyr Pro Lys Ala
        755                 760                 765

Ala Glu Arg Tyr Ala Glu Ile Ala Lys Phe Leu Gly Leu Pro Ala Ser
    770                 775                 780

Thr Val Glu Glu Gly Val Glu Ser Leu Ile Glu Ala Ile Lys Asn Leu
785                 790                 795                 800

Met Lys Glu Leu Asn Ile Pro Leu Thr Leu Lys Asp Ala Gly Ile Asn
                805                 810                 815

Lys Glu Gln Phe Glu Lys Glu Ile Glu Glu Met Ser Asp Ile Ala Phe
            820                 825                 830

Asn Asp Gln Cys Thr Gly Thr Asn Pro Arg Met Pro Leu Thr Lys Glu
        835                 840                 845

Ile Ala Glu Ile Tyr Arg Lys Ala Tyr Gly Ala
    850                 855


<210> SEQ ID NO 12
<211> LENGTH: 2580
<212> TYPE: DNA
<213> ORGANISM: T.saccharolyticum

<400> SEQUENCE: 12

atggcaacga caaaaacgga attagacgtt cagaagcaga tagatctact tgtgtcaaga      60

gcacaagagg ctcagaaaaa attcatgtct tacacgcaag agcaaatcga cgcaatagtt     120

aaggcaatgg ctttagcagg cgttgacaaa cacgtagagc tggcaaagat ggcgtacgaa     180

gagacaaaaa tgggtgtata cgaagataag ataacaaaaa atctcttcgc aacagagtac     240

gtgtaccacg acataaaaaa tgaaaagact gtaggaatca taaacgagaa catagaagaa     300

aactacatgg aagtggcaga accgataggc gtaattgccg gtgtcacacc tgtcacaaac     360

ccaacatcta ccacgatgtt taaatgctta atatccataa agacgcgaaa tcctataata     420

ttcagcttcc atccaaaggc aataaagtgc agcatcgcag cagccaaagt gatgtatgaa     480

gctgcactaa aggcaggcgc acctgaagga tgcataggat ggatagaaac gccatcaatt     540

gaggccacac agcttctcat gacacatcca ggcgtatcgc tgatccttgc aacgggcggt     600

gcaggaatgg taaaagcggc atacagctca ggaaaaccgg cattaggcgt aggtcctggc     660

aatgtgccat gctacatcga aaaatcagca aacataaaga gggctgtatc ggatctcata     720

ctaagcaaga catttgacaa tggagtaata tgcgcatcag agcaggccgt aataatagac     780

gaggaaatag cagatgaagt caaaaagctt atgaaagaat acggctgcta cttcttaaac     840

aaagatgaaa taaagaagct tgagaaattt gcaattgatg agcaaagctg cgccatgagc     900

cctgcagtgg taggtcagcc agcggcgaag attgctgaaa tggcaggctt caaagtcccc     960

gaaggcacaa agatattagt ggcagagtac gaaggagtag gtccaaaata tcctctatca    1020
```

```
agggagaaac taagcccgat tcttgcttgc tacaccgtca aagactacaa tgaaggaatc   1080

aaaaagtgcg aggaaatgac tgaattcgga ggtttaggcc actctgctgt aatacactct   1140

gaaaatcaaa acgtcataaa tgaatttgca aggcgagtcc gcacaggaag acttatcgta   1200

aattcaccat catcacaggg agcaatagga gatatataca atacaaacac gccatcactt   1260

acattaggct gtggttctat gggaagaaac tcaacgacag acaatgtaag cgtcaagaac   1320

cttttgaata ttaagcgtgt cgtgataagg aaggatagaa tgaaatggtt caagattcca   1380

ccgaagattt actttgaaag cgggtcactc cagtacctgt gcaaagtcaa aagaaaaaaa   1440

gcgtttatcg tcacagatcc attcatggtt aagcttggct tcgtagacaa agtgacatat   1500

caattagaca aagcaaacat cgaatacgaa atattctcag aagtagagcc agatccatct   1560

gttgacacag tcatgaacgg cgtaaaaata atgaattcgt acaatcctga cttaataatc   1620

gctgtaggcg gtggctctgc aatagacgca gcaaagggaa tgtggctttt ctacgaatat   1680

cctgatacag agtttgaaac attgaggctt aaatttgcag acatcagaaa aagggcattt   1740

aagttcccag aacttggcaa aaaagcgcta ttcatcgcaa taccgacaac aagcggcaca   1800

ggctcaggag tgacagcatt tgccgtaata accgacaaaa agagaaacat caagtatcca   1860

ctggcagact acgaacttac acctgacata gccataatag atcctgacct tacaaagact   1920

gtaccgccat ctgtaacagc agacacaggc atggatgtgc tgacacacgc catagaagca   1980

tacgtatcag taatggcatc agactacaca gatgcactgg cggaaaaggc tataaagatc   2040

gtatttgaat acctgccaag ggcttataaa aacggcaatg atgaagaagc ccgcgaaaag   2100

atgcacaatg cttcctgcat ggctggtatg gcattcacaa atgcattctt aggaataaac   2160

cacagcatgg cacacatact gggcggaaag ttccacatac cacacggaag agcaaatgca   2220

atacttctgc cgtatgtaat aaggtacaat gcagaaaaac ctacaaagtt tgtggcattc   2280

ccacaatacg aatatccaaa agcagcagaa agatatgcgg aaatcgccaa attcttagga   2340

ctgcctgctt caactgttga agaaggcgta gaaagcttaa tagaagctat aaagaacctc   2400

atgaaagagc ttaacattcc gcttacactt aaagacgccg gcatcaacaa agaacagttt   2460

gaaaaagaaa tagaggaaat gtcagacatc gccttcaacg atcagtgcac agggacaaac   2520

ccgagaatgc ctctcacaaa agaaattgca gagatctaca gaaaagcata cggtgcatag   2580


<210> SEQ ID NO 13
<211> LENGTH: 859
<212> TYPE: PRT
<213> ORGANISM: T.saccharolyticum

<400> SEQUENCE: 13

Met Ala Thr Thr Lys Thr Glu Leu Asp Val Gln Lys Gln Ile Asp Leu
1               5                   10                  15

Leu Val Ser Arg Ala Gln Glu Ala Gln Lys Lys Phe Met Ser Tyr Thr
            20                  25                  30

Gln Glu Gln Ile Asp Ala Ile Val Lys Ala Met Ala Leu Ala Gly Val
        35                  40                  45

Asp Lys His Val Glu Leu Ala Lys Met Ala Tyr Glu Glu Thr Lys Met
    50                  55                  60

Gly Val Tyr Glu Asp Lys Ile Thr Lys Asn Leu Phe Ala Thr Glu Tyr
65                  70                  75                  80

Val Tyr His Asp Ile Lys Asn Glu Lys Thr Val Gly Ile Ile Asn Glu
                85                  90                  95

Asn Ile Glu Glu Asn Tyr Met Glu Val Ala Glu Pro Ile Gly Val Ile
```

```
            100                 105                 110

Ala Gly Val Thr Pro Val Thr Asn Pro Thr Ser Thr Thr Met Phe Lys
        115                 120                 125

Cys Leu Ile Ser Ile Lys Thr Arg Asn Pro Ile Ile Phe Ser Phe His
    130                 135                 140

Pro Lys Ala Ile Lys Cys Ser Ile Ala Ala Ala Lys Val Met Tyr Glu
145                 150                 155                 160

Ala Ala Leu Lys Ala Gly Ala Pro Glu Gly Cys Ile Gly Trp Ile Glu
                165                 170                 175

Thr Pro Ser Ile Glu Ala Thr Gln Leu Leu Met Thr His Pro Gly Val
            180                 185                 190

Ser Leu Ile Leu Ala Thr Gly Gly Ala Gly Met Val Lys Ala Ala Tyr
        195                 200                 205

Ser Ser Gly Lys Pro Ala Leu Gly Val Gly Pro Gly Asn Val Pro Cys
    210                 215                 220

Tyr Ile Glu Lys Ser Ala Asn Ile Lys Arg Ala Val Ser Asp Leu Ile
225                 230                 235                 240

Leu Ser Lys Thr Phe Asp Asn Gly Val Ile Cys Ala Ser Glu Gln Ala
                245                 250                 255

Val Ile Ile Asp Glu Glu Ile Ala Asp Glu Val Lys Lys Leu Met Lys
            260                 265                 270

Glu Tyr Gly Cys Tyr Phe Leu Asn Lys Asp Glu Ile Lys Lys Leu Glu
        275                 280                 285

Lys Phe Ala Ile Asp Glu Gln Ser Cys Ala Met Ser Pro Ala Val Val
    290                 295                 300

Gly Gln Pro Ala Ala Lys Ile Ala Glu Met Ala Gly Phe Lys Val Pro
305                 310                 315                 320

Glu Gly Thr Lys Ile Leu Val Ala Glu Tyr Glu Gly Val Gly Pro Lys
                325                 330                 335

Tyr Pro Leu Ser Arg Glu Lys Leu Ser Pro Ile Leu Ala Cys Tyr Thr
            340                 345                 350

Val Lys Asp Tyr Asn Glu Gly Ile Lys Lys Cys Glu Glu Met Thr Glu
        355                 360                 365

Phe Gly Gly Leu Gly His Ser Ala Val Ile His Ser Glu Asn Gln Asn
    370                 375                 380

Val Ile Asn Glu Phe Ala Arg Arg Val Arg Thr Gly Arg Leu Ile Val
385                 390                 395                 400

Asn Ser Pro Ser Ser Gln Gly Ala Ile Gly Asp Ile Tyr Asn Thr Asn
                405                 410                 415

Thr Pro Ser Leu Thr Leu Gly Cys Gly Ser Met Gly Arg Asn Ser Thr
            420                 425                 430

Thr Asp Asn Val Ser Val Lys Asn Leu Leu Asn Ile Lys Arg Val Val
        435                 440                 445

Ile Arg Lys Asp Arg Met Lys Trp Phe Lys Ile Pro Pro Lys Ile Tyr
    450                 455                 460

Phe Glu Ser Gly Ser Leu Gln Tyr Leu Cys Lys Val Lys Arg Lys Lys
465                 470                 475                 480

Ala Phe Ile Val Thr Asp Pro Phe Met Val Lys Leu Gly Phe Val Asp
                485                 490                 495

Lys Val Thr Tyr Gln Leu Asp Lys Ala Asn Ile Glu Tyr Glu Ile Phe
            500                 505                 510

Ser Glu Val Glu Pro Asp Pro Ser Val Asp Thr Val Met Asn Gly Val
        515                 520                 525
```

```
Lys Ile Met Asn Ser Tyr Asn Pro Asp Leu Ile Ile Ala Val Gly Gly
    530                 535                 540

Gly Ser Ala Ile Asp Ala Ala Lys Gly Met Trp Leu Phe Tyr Glu Tyr
545                 550                 555                 560

Pro Asp Thr Glu Phe Glu Thr Leu Arg Leu Lys Phe Ala Asp Ile Arg
                565                 570                 575

Lys Arg Ala Phe Lys Phe Pro Glu Leu Gly Lys Lys Ala Leu Phe Ile
            580                 585                 590

Ala Ile Pro Thr Thr Ser Gly Thr Gly Ser Gly Val Thr Ala Phe Ala
        595                 600                 605

Val Ile Thr Asp Lys Lys Arg Asn Ile Lys Tyr Pro Leu Ala Asp Tyr
    610                 615                 620

Glu Leu Thr Pro Asp Ile Ala Ile Ile Asp Pro Asp Leu Thr Lys Thr
625                 630                 635                 640

Val Pro Pro Ser Val Thr Ala Asp Thr Gly Met Asp Val Leu Thr His
                645                 650                 655

Ala Ile Glu Ala Tyr Val Ser Val Met Ala Ser Asp Tyr Thr Asp Ala
            660                 665                 670

Leu Ala Glu Lys Ala Ile Lys Ile Val Phe Glu Tyr Leu Pro Arg Ala
        675                 680                 685

Tyr Lys Asn Gly Asn Asp Glu Glu Ala Arg Glu Lys Met His Asn Ala
    690                 695                 700

Ser Cys Met Ala Gly Met Ala Phe Thr Asn Ala Phe Leu Gly Ile Asn
705                 710                 715                 720

His Ser Met Ala His Ile Leu Gly Gly Lys Phe His Ile Pro His Gly
                725                 730                 735

Arg Ala Asn Ala Ile Leu Leu Pro Tyr Val Ile Arg Tyr Asn Ala Glu
            740                 745                 750

Lys Pro Thr Lys Phe Val Ala Phe Pro Gln Tyr Glu Tyr Pro Lys Ala
        755                 760                 765

Ala Glu Arg Tyr Ala Glu Ile Ala Lys Phe Leu Gly Leu Pro Ala Ser
    770                 775                 780

Thr Val Glu Glu Gly Val Glu Ser Leu Ile Glu Ala Ile Lys Asn Leu
785                 790                 795                 800

Met Lys Glu Leu Asn Ile Pro Leu Thr Leu Lys Asp Ala Gly Ile Asn
                805                 810                 815

Lys Glu Gln Phe Glu Lys Glu Ile Glu Glu Met Ser Asp Ile Ala Phe
            820                 825                 830

Asn Asp Gln Cys Thr Gly Thr Asn Pro Arg Met Pro Leu Thr Lys Glu
        835                 840                 845

Ile Ala Glu Ile Tyr Arg Lys Ala Tyr Gly Ala
    850                 855
```

<210> SEQ ID NO 14
<211> LENGTH: 2580
<212> TYPE: DNA
<213> ORGANISM: T.saccharolyticum

<400> SEQUENCE: 14

```
atggcaacga caaaaacgga attagacgtt cagaagcaga tagatctact tgtgtcaaga      60

gcacaagagg ctcagaaaaa attcatgtct tacacgcaag agcaaatcga cgcaatagtt     120

aaggcaatgg ctttagcagg cgttgacaaa cacgtagagc tggcaaagat ggcgtacgaa     180

gagacaaaaa tgggtgtata cgaagataag ataacaaaaa atctcttcgc aacagagtac     240
```

```
gtgtaccacg acataaaaaa tgaaaagact gtaggaatca taaacgagaa catagaagaa    300
aactacatgg aagtggcaga accgataggc gtaattgccg gtgtcacacc tgtcacaaac    360
ccaacatcta ccacgatgtt taaatgctta atatccataa agacgcgaaa tcctataata    420
ttcagcttcc atccaaaggc aataaagtgc agcatcgcag cagccaaagt gatgtatgaa    480
gctgcactaa aggcaggcgc acctgaagga tgcataggat ggatagaaac gccatcaatt    540
gaggccacac agcttctcat gacacatcca ggcgtatcgc tgatccttgc aacgggcggt    600
gcaggaatgg taaaagcggc atacagctca ggaaaaccgg cattaggcgt aggtcctggc    660
aatgtgccat gctacatcga aaaatcagca aacataaaga gggctgtatc ggatctcata    720
ctaagcaaga catttgacaa tggagtaata tgcgcatcag agcaggccgt aataatagac    780
gaggaaatag cagatgaagt caaaaagctt atgaaagaat acggctgcta cttcttaaac    840
aaagatgaaa taaagaagct tgagaaattt gcaattgatg agcaaagctg cgccatgagc    900
cctgcagtgg taggtcagcc agcggcgaag attgctgaaa tggcaggctt caaagtcccc    960
gaaggcacaa agatattagt ggcagagtac gaaggagtag gtccaaaata tcctctatca   1020
agggagaaac taagcccgat tcttgcttgc tacaccgtca aagactacaa tgaaggaatc   1080
aaaaagtgcg aggaaatgac tgaattcgga ggtttaggcc actctgctgt aatacactct   1140
gaaaatcaaa acgtcataaa tgaatttgca aggcgagtcc gcacaggaag acttatcgta   1200
aattcaccat catcacaggg agcaatagga gatatataca atacaaacac gccatcactt   1260
acattaggct gtggttctat gggaagaaac tcaacgacag acaatgtaag cgtcaagaac   1320
cttttgaata ttaagcgtgt cgtgataagg aaggatagaa tgaaatggtt caagattcca   1380
ccgaagattt actttgaaag cgggtcactc cagtacctgt gcaaagtcaa aagaaaaaaa   1440
gcgtttatcg tcacagatcc attcatggtt aagcttggct tcgtagacaa agtgacatat   1500
caattagaca aagcaaacat cgaatacgaa atattctcag aagtagagcc agatccatct   1560
gttgacacag tcatgaacgg cgtaaaaata atgaattcgt acaatcctga cttaataatc   1620
gctgtaggcg atggctctgc aatagacgca gcaaagggaa tgtggctttt ctacgaatat   1680
cctgatacag agtttgaaac attgaggctt aaatttgcag acatcagaaa aagggcattt   1740
aagttcccag aacttggcaa aaaagcgcta ttcatcgcaa taccgacaac aagcggcaca   1800
ggctcagaag tgacagcatt tgccgtaata accgacaaaa agagaaacat caagtatcca   1860
ctggcagact acgaacttac acctgacata gccataatag atcctgacct tacaaagact   1920
gtaccgccat ctgtaacagc agacacaggc atggatgtgc tgacacacgc catagaagca   1980
tacgtatcag taatggcatc agactacaca gatgcactgg cggaaaaggc tataaagatc   2040
gtatttgaat acctgccaag ggcttataaa aacggcaatg atgaagaagc ccgcgaaaag   2100
atgcacaatg cttcctgcat ggctggtatg gcattcacaa atgcattctt aggaataaac   2160
cacagcatgg cacacatact gggcggaaag ttccacatac cacacggaag agcaaatgca   2220
atacttctgc cgtatgtaat aaggtacaat gcagaaaaac ctacaaagtt tgtggcattc   2280
ccacaatacg aatatccaaa agcagcagaa agatatgcgg aaatcgccaa attcttagga   2340
ctgcctgctt caactgttga agaaggcgta gaaagcttaa tagaagctat aaagaacctc   2400
atgaaagagc ttaacattcc gcttacactt aaagacgccg gcatcaacaa agaacagttt   2460
gaaaaagaaa tagaggaaat gtcagacatc gccttcaacg atcagtgcac agggacaaac   2520
ccgagaatgc ctctcacaaa agaaattgca gagatctaca gaaaagcata cggtgcatag   2580
```

<210> SEQ ID NO 15
<211> LENGTH: 859
<212> TYPE: PRT
<213> ORGANISM: T.saccharolyticum

<400> SEQUENCE: 15

```
Met Ala Thr Thr Lys Thr Glu Leu Asp Val Gln Lys Gln Ile Asp Leu
1               5                   10                  15

Leu Val Ser Arg Ala Gln Glu Ala Gln Lys Lys Phe Met Ser Tyr Thr
            20                  25                  30

Gln Glu Gln Ile Asp Ala Ile Val Lys Ala Met Ala Leu Ala Gly Val
        35                  40                  45

Asp Lys His Val Glu Leu Ala Lys Met Ala Tyr Glu Glu Thr Lys Met
    50                  55                  60

Gly Val Tyr Glu Asp Lys Ile Thr Lys Asn Leu Phe Ala Thr Glu Tyr
65                  70                  75                  80

Val Tyr His Asp Ile Lys Asn Glu Lys Thr Val Gly Ile Ile Asn Glu
                85                  90                  95

Asn Ile Glu Glu Asn Tyr Met Glu Val Ala Glu Pro Ile Gly Val Ile
            100                 105                 110

Ala Gly Val Thr Pro Val Thr Asn Pro Thr Ser Thr Thr Met Phe Lys
        115                 120                 125

Cys Leu Ile Ser Ile Lys Thr Arg Asn Pro Ile Ile Phe Ser Phe His
    130                 135                 140

Pro Lys Ala Ile Lys Cys Ser Ile Ala Ala Ala Lys Val Met Tyr Glu
145                 150                 155                 160

Ala Ala Leu Lys Ala Gly Ala Pro Glu Gly Cys Ile Gly Trp Ile Glu
                165                 170                 175

Thr Pro Ser Ile Glu Ala Thr Gln Leu Leu Met Thr His Pro Gly Val
            180                 185                 190

Ser Leu Ile Leu Ala Thr Gly Gly Ala Gly Met Val Lys Ala Ala Tyr
        195                 200                 205

Ser Ser Gly Lys Pro Ala Leu Gly Val Gly Pro Gly Asn Val Pro Cys
    210                 215                 220

Tyr Ile Glu Lys Ser Ala Asn Ile Lys Arg Ala Val Ser Asp Leu Ile
225                 230                 235                 240

Leu Ser Lys Thr Phe Asp Asn Gly Val Ile Cys Ala Ser Glu Gln Ala
                245                 250                 255

Val Ile Ile Asp Glu Glu Ile Ala Asp Glu Val Lys Lys Leu Met Lys
            260                 265                 270

Glu Tyr Gly Cys Tyr Phe Leu Asn Lys Asp Glu Ile Lys Lys Leu Glu
        275                 280                 285

Lys Phe Ala Ile Asp Glu Gln Ser Cys Ala Met Ser Pro Ala Val Val
    290                 295                 300

Gly Gln Pro Ala Ala Lys Ile Ala Glu Met Ala Gly Phe Lys Val Pro
305                 310                 315                 320

Glu Gly Thr Lys Ile Leu Val Ala Glu Tyr Glu Gly Val Gly Pro Lys
                325                 330                 335

Tyr Pro Leu Ser Arg Glu Lys Leu Ser Pro Ile Leu Ala Cys Tyr Thr
            340                 345                 350

Val Lys Asp Tyr Asn Glu Gly Ile Lys Lys Cys Glu Glu Met Thr Glu
        355                 360                 365

Phe Gly Gly Leu Gly His Ser Ala Val Ile His Ser Glu Asn Gln Asn
    370                 375                 380
```

```
Val Ile Asn Glu Phe Ala Arg Arg Val Arg Thr Gly Arg Leu Ile Val
385                 390                 395                 400

Asn Ser Pro Ser Ser Gln Gly Ala Ile Gly Asp Ile Tyr Asn Thr Asn
                405                 410                 415

Thr Pro Ser Leu Thr Leu Gly Cys Gly Ser Met Gly Arg Asn Ser Thr
            420                 425                 430

Thr Asp Asn Val Ser Val Lys Asn Leu Leu Asn Ile Lys Arg Val Val
        435                 440                 445

Ile Arg Lys Asp Arg Met Lys Trp Phe Lys Ile Pro Pro Lys Ile Tyr
    450                 455                 460

Phe Glu Ser Gly Ser Leu Gln Tyr Leu Cys Lys Val Lys Arg Lys Lys
465                 470                 475                 480

Ala Phe Ile Val Thr Asp Pro Phe Met Val Lys Leu Gly Phe Val Asp
                485                 490                 495

Lys Val Thr Tyr Gln Leu Asp Lys Ala Asn Ile Glu Tyr Glu Ile Phe
            500                 505                 510

Ser Glu Val Glu Pro Asp Pro Ser Val Asp Thr Val Met Asn Gly Val
        515                 520                 525

Lys Ile Met Asn Ser Tyr Asn Pro Asp Leu Ile Ile Ala Val Gly Asp
    530                 535                 540

Gly Ser Ala Ile Asp Ala Ala Lys Gly Met Trp Leu Phe Tyr Glu Tyr
545                 550                 555                 560

Pro Asp Thr Glu Phe Glu Thr Leu Arg Leu Lys Phe Ala Asp Ile Arg
                565                 570                 575

Lys Arg Ala Phe Lys Phe Pro Glu Leu Gly Lys Lys Ala Leu Phe Ile
            580                 585                 590

Ala Ile Pro Thr Thr Ser Gly Thr Gly Ser Glu Val Thr Ala Phe Ala
        595                 600                 605

Val Ile Thr Asp Lys Lys Arg Asn Ile Lys Tyr Pro Leu Ala Asp Tyr
    610                 615                 620

Glu Leu Thr Pro Asp Ile Ala Ile Ile Asp Pro Asp Leu Thr Lys Thr
625                 630                 635                 640

Val Pro Pro Ser Val Thr Ala Asp Thr Gly Met Asp Val Leu Thr His
                645                 650                 655

Ala Ile Glu Ala Tyr Val Ser Val Met Ala Ser Asp Tyr Thr Asp Ala
            660                 665                 670

Leu Ala Glu Lys Ala Ile Lys Ile Val Phe Glu Tyr Leu Pro Arg Ala
        675                 680                 685

Tyr Lys Asn Gly Asn Asp Glu Glu Ala Arg Glu Lys Met His Asn Ala
    690                 695                 700

Ser Cys Met Ala Gly Met Ala Phe Thr Asn Ala Phe Leu Gly Ile Asn
705                 710                 715                 720

His Ser Met Ala His Ile Leu Gly Gly Lys Phe His Ile Pro His Gly
                725                 730                 735

Arg Ala Asn Ala Ile Leu Leu Pro Tyr Val Ile Arg Tyr Asn Ala Glu
            740                 745                 750

Lys Pro Thr Lys Phe Val Ala Phe Pro Gln Tyr Glu Tyr Pro Lys Ala
        755                 760                 765

Ala Glu Arg Tyr Ala Glu Ile Ala Lys Phe Leu Gly Leu Pro Ala Ser
    770                 775                 780

Thr Val Glu Glu Gly Val Glu Ser Leu Ile Glu Ala Ile Lys Asn Leu
785                 790                 795                 800
```

```
Met Lys Glu Leu Asn Ile Pro Leu Thr Leu Lys Asp Ala Gly Ile Asn
                805                 810                 815

Lys Glu Gln Phe Glu Lys Glu Ile Glu Glu Met Ser Asp Ile Ala Phe
            820                 825                 830

Asn Asp Gln Cys Thr Gly Thr Asn Pro Arg Met Pro Leu Thr Lys Glu
        835                 840                 845

Ile Ala Glu Ile Tyr Arg Lys Ala Tyr Gly Ala
    850                 855


<210> SEQ ID NO 16
<211> LENGTH: 2622
<212> TYPE: DNA
<213> ORGANISM: C.thermocellum

<400> SEQUENCE: 16

atgacgaaaa tagcgaataa atacgaagtt attgataatg ttgaaaagct tgaaaaggct      60

ttgaaacgtt taagagaagc tcaaagtgtt tatgcaacct atacacagga gcaggttgac     120

aaaatttctt ttgaggcggc aatggcggcc aataaaatga gaattcctct tgccaaaatg     180

gctgtggagg aaacaggcat gggagtggtt gaagacaagg ttatcaaaaa ccactatgct     240

tctgagtata tctataatgc gtacaaaaac actaaaacct gcggtgttat tgaagaggac     300

cctgctttcg gtattaaaaa aatagcagag cctttggggg ttattgcggc ggttatacct     360

actacgaatc cgacatcgac agcaatcttt aagactctta ttgcattaaa gacgagaaat     420

gcaattatta taagcccaca ccccagggca aaaaactcaa cgatagaagc ggcgaaaatt     480

gttttggagg cggccgttaa agccggtgct ccggaaggca tcattggctg gattgatgtg     540

ccgagccttg aacttaccaa cctggtaatg agagaagcag atgtgattct cgcaacaggc     600

ggtcccggac tggttaaagc agcttactct tcgggcaaac cggctattgg tgtcggagcg     660

ggcaatactc ctgcaattat tgatgattcg gccgacattg tcttggcagt gaactcaata     720

atacattcaa aaactttcga caacggtatg atttgtgctt cagagcaatc ggtcattgtt     780

ctggacgggg tatataaaga ggtaaaaaaa gaatttgaaa aaagaggatg ctatttctta     840

aatgaagatg aaactgaaaa ggtaagaaaa acaattataa taaacggtgc gttaaatgcc     900

aagatagtag gtcagaaagc tcacacaatt gcaaaccttg caggttttga ggtacccgag     960

actacaaaaa ttctgatagg cgaagttacc agcgtggata tttccgaaga atttgcccac    1020

gaaaagttgt gcccggtact ggcaatgtac agggcaaagg attttgacga tgcccttgat    1080

aaagcagaaa ggttggtagc tgacggtgga tttggccata cttcgtcact ttatatagat    1140

acggtaacac agaaagagaa acttcagaaa ttctctgaaa ggatgaaaac ctgccgtata    1200

ttggttaata cgccgtcatc ccagggaggt atcggtgacc tttacaactt caagcttgct    1260

ccgtctctca ccctcggctg cggttcctgg ggaggaaatt cagtttccga caatgtggga    1320

gtcaagcatt tgttaaacat taaaacagtt gccgagagga gagagaacat gctctggttc    1380

agaacacctg aaaagattta tataaaaaga ggttgtctgc ctgttgcatt ggatgagctt    1440

aaaaatgtaa tgggtaaaaa gaaagcattt attgtaacgg ataacttcct gtacaataac    1500

ggctacacca agccgattac ggataagctg gatgaaatgg gaattgtgca caagaccttc    1560

tttgatgtgt ctccagaccc atcccttgca tctgccaaag ccggtgcggc agaaatgctg    1620

gctttccagc ctgacaccat aattgcggtc ggcggcggat ctgccatgga cgcggccaaa    1680

atcatgtggg tgatgtatga acatccggaa gttgacttta tggacatggc aatgagattt    1740

atggatataa gaaagagagt ttacaccttc ccgaagatgg gacagaaggc atactttatc    1800
```

```
gcaattccga cttccgcggg tacaggttca gaagtgacac cttttgcggt tattactgat   1860

gaaaaaacag gaattaaata ccctctggcc gactatgaat tgttgccgga catggctatt   1920

gtagatgccg atatgatgat gaatgctcca aagggactta ccgcagcttc cggtatagac   1980

gcattgaccc acgctctgga agcctatgtt tcaatgcttg cgaccgacta tacggatagc   2040

cttgcccttc gtgcaataaa gatgatattt gaatatctcc cgagagccta tgaaaacggt   2100

gcaagtgacc tggttgcaag agagaaaatg gccaatgccg caacaatagc cggaatggct   2160

tttgccaatg cctttttggg tgtatgccat tcaatggcgc gcaaactggg tgctttttat   2220

cacctgcccc acggtgttgc caatgcactt atgataaacg aagtaatcag attcaactca   2280

tccgaggctc cgaccaagat gggtactttc ccgcagtatg accatccgcg cacgctggaa   2340

aggtatgcag aaattgccga ttatatcgga cttaagggca agaataacga agaaaaagtt   2400

gaaaacttga ttaaagctat tgatgagctt aaagaaaagg tgggcatcag gaagaccatc   2460

aaagattatg acatagatga aaaggaattt ttggacagac tggacgaaat ggtggaacag   2520

gcttttgacg accagtgcac aggtacaaat ccaagatacc cgcttatgaa tgaaatcagg   2580

caaatgtatc tgaacgctta ttacggaggt gcgaagaaat ga                      2622
```

<210> SEQ ID NO 17
<211> LENGTH: 873
<212> TYPE: PRT
<213> ORGANISM: C.thermocellum

<400> SEQUENCE: 17

```
Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
            20                  25                  30

Thr Tyr Thr Gln Glu Gln Val Asp Lys Ile Phe Phe Glu Ala Ala Met
        35                  40                  45

Ala Ala Asn Lys Met Arg Ile Pro Leu Ala Lys Met Ala Val Glu Glu
    50                  55                  60

Thr Gly Met Gly Val Val Glu Asp Lys Val Ile Lys Asn His Tyr Ala
65                  70                  75                  80

Ser Glu Tyr Ile Tyr Asn Ala Tyr Lys Asn Thr Lys Thr Cys Gly Val
                85                  90                  95

Ile Glu Glu Asp Pro Ala Phe Gly Ile Lys Lys Ile Ala Glu Pro Leu
            100                 105                 110

Gly Val Ile Ala Ala Val Ile Pro Thr Thr Asn Pro Thr Ser Thr Ala
        115                 120                 125

Ile Phe Lys Thr Leu Ile Ala Leu Lys Thr Arg Asn Ala Ile Ile Ile
    130                 135                 140

Ser Pro His Pro Arg Ala Lys Asn Ser Thr Ile Glu Ala Ala Lys Ile
145                 150                 155                 160

Val Leu Glu Ala Ala Val Lys Ala Gly Ala Pro Glu Gly Ile Ile Gly
                165                 170                 175

Trp Ile Asp Val Pro Ser Leu Glu Leu Thr Asn Leu Val Met Arg Glu
            180                 185                 190

Ala Asp Val Ile Leu Ala Thr Gly Gly Pro Gly Leu Val Lys Ala Ala
        195                 200                 205

Tyr Ser Ser Gly Lys Pro Ala Ile Gly Val Gly Ala Gly Asn Thr Pro
    210                 215                 220
```

```
Ala Ile Ile Asp Asp Ser Ala Asp Ile Val Leu Ala Val Asn Ser Ile
225                 230                 235                 240

Ile His Ser Lys Thr Phe Asp Asn Gly Met Ile Cys Ala Ser Glu Gln
                245                 250                 255

Ser Val Ile Val Leu Asp Gly Val Tyr Lys Glu Val Lys Lys Glu Phe
            260                 265                 270

Glu Lys Arg Gly Cys Tyr Phe Leu Asn Glu Asp Glu Thr Glu Lys Val
        275                 280                 285

Arg Lys Thr Ile Ile Ile Asn Gly Ala Leu Asn Ala Lys Ile Val Gly
    290                 295                 300

Gln Lys Ala His Thr Ile Ala Asn Leu Ala Gly Phe Glu Val Pro Glu
305                 310                 315                 320

Thr Thr Lys Ile Leu Ile Gly Glu Val Thr Ser Val Asp Ile Ser Glu
                325                 330                 335

Glu Phe Ala His Glu Lys Leu Cys Pro Val Leu Ala Met Tyr Arg Ala
            340                 345                 350

Lys Asp Phe Asp Asp Ala Leu Asp Lys Ala Glu Arg Leu Val Ala Asp
        355                 360                 365

Gly Gly Phe Gly His Thr Ser Ser Leu Tyr Ile Asp Thr Val Thr Gln
    370                 375                 380

Lys Glu Lys Leu Gln Lys Phe Ser Glu Arg Met Lys Thr Cys Arg Ile
385                 390                 395                 400

Leu Val Asn Thr Pro Ser Ser Gln Gly Gly Ile Gly Asp Leu Tyr Asn
                405                 410                 415

Phe Lys Leu Ala Pro Ser Leu Thr Leu Gly Cys Gly Ser Trp Gly Gly
            420                 425                 430

Asn Ser Val Ser Asp Asn Val Gly Val Lys His Leu Leu Asn Ile Lys
        435                 440                 445

Thr Val Ala Glu Arg Arg Glu Asn Met Leu Trp Phe Arg Thr Pro Glu
    450                 455                 460

Lys Ile Tyr Ile Lys Arg Gly Cys Leu Pro Val Ala Leu Asp Glu Leu
465                 470                 475                 480

Lys Asn Val Met Gly Lys Lys Lys Ala Phe Ile Val Thr Asp Asn Phe
                485                 490                 495

Leu Tyr Asn Asn Gly Tyr Thr Lys Pro Ile Thr Asp Lys Leu Asp Glu
            500                 505                 510

Met Gly Ile Val His Lys Thr Phe Phe Asp Val Ser Pro Asp Pro Ser
        515                 520                 525

Leu Ala Ser Ala Lys Ala Gly Ala Ala Glu Met Leu Ala Phe Gln Pro
    530                 535                 540

Asp Thr Ile Ile Ala Val Gly Gly Gly Ser Ala Met Asp Ala Ala Lys
545                 550                 555                 560

Ile Met Trp Val Met Tyr Glu His Pro Glu Val Asp Phe Met Asp Met
                565                 570                 575

Ala Met Arg Phe Met Asp Ile Arg Lys Arg Val Tyr Thr Phe Pro Lys
            580                 585                 590

Met Gly Gln Lys Ala Tyr Phe Ile Ala Ile Pro Thr Ser Ala Gly Thr
        595                 600                 605

Gly Ser Glu Val Thr Pro Phe Ala Val Ile Thr Asp Glu Lys Thr Gly
    610                 615                 620

Ile Lys Tyr Pro Leu Ala Asp Tyr Glu Leu Leu Pro Asp Met Ala Ile
625                 630                 635                 640

Val Asp Ala Asp Met Met Met Asn Ala Pro Lys Gly Leu Thr Ala Ala
```

```
                645                 650                 655

Ser Gly Ile Asp Ala Leu Thr His Ala Leu Glu Ala Tyr Val Ser Met
            660                 665                 670

Leu Ala Thr Asp Tyr Thr Asp Ser Leu Ala Leu Arg Ala Ile Lys Met
        675                 680                 685

Ile Phe Glu Tyr Leu Pro Arg Ala Tyr Glu Asn Gly Ala Ser Asp Leu
    690                 695                 700

Val Ala Arg Glu Lys Met Ala Asn Ala Ala Thr Ile Ala Gly Met Ala
705                 710                 715                 720

Phe Ala Asn Ala Phe Leu Gly Val Cys His Ser Met Ala Arg Lys Leu
                725                 730                 735

Gly Ala Phe Tyr His Leu Pro His Gly Val Ala Asn Ala Leu Met Ile
            740                 745                 750

Asn Glu Val Ile Arg Phe Asn Ser Ser Glu Ala Pro Thr Lys Met Gly
        755                 760                 765

Thr Phe Pro Gln Tyr Asp His Pro Arg Thr Leu Glu Arg Tyr Ala Glu
    770                 775                 780

Ile Ala Asp Tyr Ile Gly Leu Lys Gly Lys Asn Asn Glu Glu Lys Val
785                 790                 795                 800

Glu Asn Leu Ile Lys Ala Ile Asp Glu Leu Lys Glu Lys Val Gly Ile
                805                 810                 815

Arg Lys Thr Ile Lys Asp Tyr Asp Ile Asp Glu Lys Glu Phe Leu Asp
            820                 825                 830

Arg Leu Asp Glu Met Val Glu Gln Ala Phe Asp Asp Gln Cys Thr Gly
        835                 840                 845

Thr Asn Pro Arg Tyr Pro Leu Met Asn Glu Ile Arg Gln Met Tyr Leu
    850                 855                 860

Asn Ala Tyr Tyr Gly Gly Ala Lys Lys
865                 870


<210> SEQ ID NO 18
<211> LENGTH: 2622
<212> TYPE: DNA
<213> ORGANISM: C.thermocellum

<400> SEQUENCE: 18

atgacgaaaa tagcgaataa atacgaagtt attgataatg ttgaaaagct tgaaaaggct      60

ttgaaacgtt taagagaagc tcaaagtgtt tatgcaacct atacacagga gcaggttgac     120

aaaattttct ttgaggcggc aatggcggcc aataaaatga gaattcctct tgccaaaatg     180

gctgtggagg aaacaggcat gggagtggtt gaagacaagg ttatcaaaaa ccactatgct     240

tctgagtata tctataatgc gtacaaaaac actaaaacct gcggtgttat tgaagaggac     300

cctgctttcg gtattaaaaa aatagcagag cctttggggg ttattgcggc ggttatacct     360

actacgaatc cgacatcgac agcaatcttt aagactctta ttgcattaaa gacgagaaat     420

gcaattatta taagcccaca ccccagggca aaaaactcaa cgatagaagc ggcgaaaatt     480

gttttggagg cggccgttaa agccggtgct ccggaaggca tcattggctg gattgatgtg     540

ccgagccttg aacttaccaa cctggtaatg agagaagcag atgtgattct cgcaacaggc     600

ggtcccggac tggttaaagc agcttactct tcgggcaaac cggctattgg tgtcggagcg     660

ggcaatactc ctgcaattat tgatgattcg gccgacattg tcttggcagt gaactcaata     720

atacattcaa aaactttcga caacggtatg atttgtgctt cagagcaatc ggtcattgtt     780

ctggacgggg tatataaaga ggtaaaaaaa gaatttgaaa aaagaggatg ctatttctta     840
```

```
aatgaagatg aaactgaaaa ggtaagaaaa acaattataa taaacggtgc gttaaatgcc    900
aagatagtag gtcagaaagc tcacacaatt gcaaaccttg caggttttga ggtacccgag    960
actacaaaaa ttctgatagg cgaagttacc agcgtggata tttccgaaga atttgcccac   1020
gaaaagttgt gcccggtact ggcaatgtac agggcaaagg attttgacga tgcccttgat   1080
aaagcagaaa ggttggtagc tgacggtgga tttggccata cttcgtcact ttatatagat   1140
acggtaacac agaaagagaa acttcagaaa ttctctgaaa ggatgaaaac ctgccgtata   1200
ttggttaata cgccgtcatc ccagggaggt atcggtgacc tttacaactt caagcttgct   1260
ccgtctctca ccctcggctg cggttcctgg ggaggaaatt cagtttccga caatgtggga   1320
gtcaagcatt tgttaaacat taaaacagtt gccgagagga gagagaacat gctctggttc   1380
agaacacctg aaaagattta tataaaaaga ggttgtctgc ctgttgcatt ggatgagctt   1440
aaaaatgtaa tgggtaaaaa gaaagcattt attgtaacgg ataacttcct gtacaataac   1500
ggctacacca agccgattac ggataagctg gatgaaatgg gaattgtgca caagaccttc   1560
tttgatgtgt ctccagaccc atcccttgca tctgccaaag ccggtgcggc agaaatgctg   1620
gctttccagc ctgacaccat aattgcggtc ggcggcagat ctgccatgga cgcggccaaa   1680
atcatgtggg tgatgtatga acatccggaa gttgacttta tggacatggc aatgagattt   1740
atggatataa gaaagagagt ttacaccttc ccgaagatgg gacagaaggc atactttatc   1800
gcaattccga cttccgcggg tacaggttca gaagtgacac cttttgcggt tattactgat   1860
gaaaaaacag gaattaaata ccctctggcc gactatgaat tgttgccgga catggctatt   1920
gtagatgccg atatgatgat gaatgctcca aagggactta ccgcagcttc cggtatagac   1980
gcattgaccc acgctctgga agcctatgtt tcaatgcttg cgaccgacta tacggatagc   2040
cttgcccttc gtgcaataaa gatgatattt gaatatctcc cgagagccta tgaaaacggt   2100
gcaagtgacc cggttgcaag agagaaaatg gccaatgccg caacaatagc cggaatggct   2160
tttgccaatg cctttttggg tgtatgccat tcaatggcgc acaaactggg tgctttttat   2220
cacctgcccc acggtgttgc caatgcactt atgataaacg aagtaatcag attcaactca   2280
tccgaggctc cgaccaagat gggtactttc ccgcagtatg accatccgcg cacgctggaa   2340
aggtatgcag aaattgccga ttatatcgga cttaagggca agaataacga agaaaaagtt   2400
gaaaacttga ttaaagctat tgatgagctt aaagaaaagg tgggcatcag gaagaccatc   2460
aaagattatg acatagatga aaaggaattt ttggacagac tggacgaaat ggtggaacag   2520
gcttttgacg accagtgcac aggtacaaat ccaagatacc cgcttatgaa tgaaatcagg   2580
caaatgtatc tgaacgctta ttacggaggt gcgaagaaat ga                      2622
```

```
<210> SEQ ID NO 19
<211> LENGTH: 873
<212> TYPE: PRT
<213> ORGANISM: C.thermocellum

<400> SEQUENCE: 19

Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
            20                  25                  30

Thr Tyr Thr Gln Glu Gln Val Asp Lys Ile Phe Phe Glu Ala Ala Met
        35                  40                  45

Ala Ala Asn Lys Met Arg Ile Pro Leu Ala Lys Met Ala Val Glu Glu
```

```
    50                  55                  60

Thr Gly Met Gly Val Val Glu Asp Lys Val Ile Lys Asn His Tyr Ala
65                  70                  75                  80

Ser Glu Tyr Ile Tyr Asn Ala Tyr Lys Asn Thr Lys Thr Cys Gly Val
                85                  90                  95

Ile Glu Glu Asp Pro Ala Phe Gly Ile Lys Lys Ile Ala Glu Pro Leu
            100                 105                 110

Gly Val Ile Ala Ala Val Ile Pro Thr Thr Asn Pro Thr Ser Thr Ala
        115                 120                 125

Ile Phe Lys Thr Leu Ile Ala Leu Lys Thr Arg Asn Ala Ile Ile Ile
    130                 135                 140

Ser Pro His Pro Arg Ala Lys Asn Ser Thr Ile Glu Ala Ala Lys Ile
145                 150                 155                 160

Val Leu Glu Ala Ala Val Lys Ala Gly Ala Pro Glu Gly Ile Ile Gly
                165                 170                 175

Trp Ile Asp Val Pro Ser Leu Glu Leu Thr Asn Leu Val Met Arg Glu
            180                 185                 190

Ala Asp Val Ile Leu Ala Thr Gly Gly Pro Gly Leu Val Lys Ala Ala
        195                 200                 205

Tyr Ser Ser Gly Lys Pro Ala Ile Gly Val Gly Ala Gly Asn Thr Pro
    210                 215                 220

Ala Ile Ile Asp Asp Ser Ala Asp Ile Val Leu Ala Val Asn Ser Ile
225                 230                 235                 240

Ile His Ser Lys Thr Phe Asp Asn Gly Met Ile Cys Ala Ser Glu Gln
                245                 250                 255

Ser Val Ile Val Leu Asp Gly Val Tyr Lys Glu Val Lys Lys Glu Phe
            260                 265                 270

Glu Lys Arg Gly Cys Tyr Phe Leu Asn Glu Asp Glu Thr Glu Lys Val
        275                 280                 285

Arg Lys Thr Ile Ile Ile Asn Gly Ala Leu Asn Ala Lys Ile Val Gly
    290                 295                 300

Gln Lys Ala His Thr Ile Ala Asn Leu Ala Gly Phe Glu Val Pro Glu
305                 310                 315                 320

Thr Thr Lys Ile Leu Ile Gly Glu Val Thr Ser Val Asp Ile Ser Glu
                325                 330                 335

Glu Phe Ala His Glu Lys Leu Cys Pro Val Leu Ala Met Tyr Arg Ala
            340                 345                 350

Lys Asp Phe Asp Asp Ala Leu Asp Lys Ala Glu Arg Leu Val Ala Asp
        355                 360                 365

Gly Gly Phe Gly His Thr Ser Ser Leu Tyr Ile Asp Thr Val Thr Gln
    370                 375                 380

Lys Glu Lys Leu Gln Lys Phe Ser Glu Arg Met Lys Thr Cys Arg Ile
385                 390                 395                 400

Leu Val Asn Thr Pro Ser Ser Gln Gly Gly Ile Gly Asp Leu Tyr Asn
                405                 410                 415

Phe Lys Leu Ala Pro Ser Leu Thr Leu Gly Cys Gly Ser Trp Gly Gly
            420                 425                 430

Asn Ser Val Ser Asp Asn Val Gly Val Lys His Leu Leu Asn Ile Lys
        435                 440                 445

Thr Val Ala Glu Arg Arg Glu Asn Met Leu Trp Phe Arg Thr Pro Glu
    450                 455                 460

Lys Ile Tyr Ile Lys Arg Gly Cys Leu Pro Val Ala Leu Asp Glu Leu
465                 470                 475                 480
```

```
Lys Asn Val Met Gly Lys Lys Lys Ala Phe Ile Val Thr Asp Asn Phe
                485                 490                 495

Leu Tyr Asn Asn Gly Tyr Thr Lys Pro Ile Thr Asp Lys Leu Asp Glu
            500                 505                 510

Met Gly Ile Val His Lys Thr Phe Phe Asp Val Ser Pro Asp Pro Ser
        515                 520                 525

Leu Ala Ser Ala Lys Ala Gly Ala Ala Glu Met Leu Ala Phe Gln Pro
    530                 535                 540

Asp Thr Ile Ile Ala Val Gly Gly Arg Ser Ala Met Asp Ala Ala Lys
545                 550                 555                 560

Ile Met Trp Val Met Tyr Glu His Pro Glu Val Asp Phe Met Asp Met
                565                 570                 575

Ala Met Arg Phe Met Asp Ile Arg Lys Arg Val Tyr Thr Phe Pro Lys
            580                 585                 590

Met Gly Gln Lys Ala Tyr Phe Ile Ala Ile Pro Thr Ser Ala Gly Thr
        595                 600                 605

Gly Ser Glu Val Thr Pro Phe Ala Val Ile Thr Asp Glu Lys Thr Gly
    610                 615                 620

Ile Lys Tyr Pro Leu Ala Asp Tyr Glu Leu Leu Pro Asp Met Ala Ile
625                 630                 635                 640

Val Asp Ala Asp Met Met Met Asn Ala Pro Lys Gly Leu Thr Ala Ala
                645                 650                 655

Ser Gly Ile Asp Ala Leu Thr His Ala Leu Glu Ala Tyr Val Ser Met
            660                 665                 670

Leu Ala Thr Asp Tyr Thr Asp Ser Leu Ala Leu Arg Ala Ile Lys Met
        675                 680                 685

Ile Phe Glu Tyr Leu Pro Arg Ala Tyr Glu Asn Gly Ala Ser Asp Pro
    690                 695                 700

Val Ala Arg Glu Lys Met Ala Asn Ala Ala Thr Ile Ala Gly Met Ala
705                 710                 715                 720

Phe Ala Asn Ala Phe Leu Gly Val Cys His Ser Met Ala His Lys Leu
                725                 730                 735

Gly Ala Phe Tyr His Leu Pro His Gly Val Ala Asn Ala Leu Met Ile
            740                 745                 750

Asn Glu Val Ile Arg Phe Asn Ser Ser Glu Ala Pro Thr Lys Met Gly
        755                 760                 765

Thr Phe Pro Gln Tyr Asp His Pro Arg Thr Leu Glu Arg Tyr Ala Glu
    770                 775                 780

Ile Ala Asp Tyr Ile Gly Leu Lys Gly Lys Asn Asn Glu Glu Lys Val
785                 790                 795                 800

Glu Asn Leu Ile Lys Ala Ile Asp Glu Leu Lys Glu Lys Val Gly Ile
                805                 810                 815

Arg Lys Thr Ile Lys Asp Tyr Asp Ile Asp Glu Lys Glu Phe Leu Asp
            820                 825                 830

Arg Leu Asp Glu Met Val Glu Gln Ala Phe Asp Asp Gln Cys Thr Gly
        835                 840                 845

Thr Asn Pro Arg Tyr Pro Leu Met Asn Glu Ile Arg Gln Met Tyr Leu
    850                 855                 860

Asn Ala Tyr Tyr Gly Gly Ala Lys Lys
865                 870
```

<210> SEQ ID NO 20
<211> LENGTH: 2622

```
<212> TYPE: DNA
<213> ORGANISM: C.thermocellum

<400> SEQUENCE: 20

atgacgaaaa tagcgaataa atacgaagtt attgataatg ttgaaaagct tgaaaaggct     60

ttgaaacgtt taagagaagc tcaaagtgtt tatgcaacct atacacagga gcaggttgac    120

aaaattttct ttgaggcggc aatggcggcc aataaaatga gaattcctct tgccaaaatg    180

gctgtggagg aaacaggcat gggagtggtt gaagacaagg ttatcaaaaa ccactatgct    240

tctgagtata tctataatgc gtacaaaaac actaaaacct gcggtgttat tgaagaggac    300

cctgctttcg gtattaaaaa aatagcagag cctttggggg ttattgcggc ggttatacct    360

actacgaatc cgacatcgac agcaatcttt aagactctta ttgcattaaa gacgagaaat    420

gcaattatta taagcccaca ccccagggca aaaaactcaa cgatagaagc ggcgaaaatt    480

gttttggagg cggccgttaa agccggtgct ccggaaggca tcattggctg gattgatgtg    540

ccgagccttg aacttaccaa cctggtaatg agagaagcag atgtgattct cgcaacaggc    600

ggtcccggac tggttaaagc agcttactct tcgggcaaac cggctattgg tgtcggagcg    660

ggcaatactc ctgcaattat tgatgattcg gccgacattg tcttggcagt gaactcaata    720

atacattcaa aaactttcga caacggtatg atttgtgctt cagagcaatc ggtcattgtt    780

ctggacgggg tatataaaga ggtaaaaaaa gaatttgaaa aaagaggatg ctatttctta    840

aatgaagatg aaactgaaaa ggtaagaaaa acaattataa taaacggtgc gttaaatgcc    900

aagatagtag gtcagaaagc tcacacaatt gcaaaccttg caggttttga ggtacccgag    960

actacaaaaa ttctgatagg cgaagttacc agcgtggata tttccgaaga atttgcccac   1020

gaaaagttgt gcccggtact ggcaatgtac agggcaaagg attttgacga tgcccttgat   1080

aaagcagaaa ggttggtagc tgacggtgga tttggccata cttcgtcact ttatatagat   1140

acggtaacac agaaagagaa acttcagaaa ttctctgaaa ggatgaaaac ctgccgtata   1200

ttggttaata cgccgtcatc ccagggaggt atcggtgacc tttacaactt caagcttgct   1260

ccgtctctca ccctcggctg cggttcctgg ggaggaaatt cagtttccga caatgtggga   1320

gtcaagcatt tgttaaacat taaaacagtt gccgagagga gagagaacat gctctggttc   1380

agaacacctg aaaagattta tataaaaaga ggttgtctgc ctgttgcatt ggatgagctt   1440

aaaaatgtaa tgggtaaaaa gaaagcattt attgtaacgg gtaacttcct gtacaataac   1500

ggctacacca agccgattac ggataagctg gatgaaatgg gaattgtgca caagaccttc   1560

tttgatgtgt ctccagaccc atcccttgca tctgccaaag ccggtgcggc agaaatgctg   1620

gctttccagc ctgacaccat aattgcggtc ggcggcggat ctgccatgga cgcggccaaa   1680

atcatgtggg tgatgtatga acatccggaa gttgacttta tggacatggc aatgagattt   1740

atggatataa gaaagagagt ttacaccttc ccgaagatgg gacagaaggc atactttatc   1800

gcaattccga cttccgcggg tacaggttca gaagtgacac cttttgcggt tattactgat   1860

gaaaaaacag gaattaaata ccctctggcc gactatgaat tgttgccgga catggctatt   1920

gtagatgccg atatgatgat gaatgctcca aagggactta ccgcagcttc cggtatagac   1980

gcattgaccc acgctctgga agcctatgtt tcaatgcttg cgaccgacta tacggatagc   2040

cttgcccttc gtgcaataaa gatgatattt gaatatctcc cgagagccta tgaaaacggt   2100

gcaagtgacc cggttgcaag agagaaaatg gccaatgccg caacaatagc cggaatggct   2160

tttgccaatg cctttttggg tgtatgccat tcaatggcgc acaaactggg tgctttttat   2220
```

```
cacctgcccc acggtgttgc caatgcactt atgataaacg aagtaatcag attcaactca   2280

tccgaggctc cgaccaagat gggtactttc ccgcagtatg accatccgcg cacgctggaa   2340

aggtatgcag aaattgccga ttatatcgga cttaagggca agaataacga agaaaaagtt   2400

gaaaacttga ttaaagctat tgatgagctt aaagaaaagg tgggcatcag gaagaccatc   2460

aaagattatg acatagatga aaaggaattt ttggacagac tggacgaaat ggtggaacag   2520

gcttttgacg accagtgcac aggtacaaat ccaagatacc cgcttatgaa tgaaatcagg   2580

caaatgtatc tgaacgctta ttacggaggt gcgaagaaat ga                      2622


<210> SEQ ID NO 21
<211> LENGTH: 873
<212> TYPE: PRT
<213> ORGANISM: C.thermocellum

<400> SEQUENCE: 21

Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
            20                  25                  30

Thr Tyr Thr Gln Glu Gln Val Asp Lys Ile Phe Phe Glu Ala Ala Met
        35                  40                  45

Ala Ala Asn Lys Met Arg Ile Pro Leu Ala Lys Met Ala Val Glu Glu
    50                  55                  60

Thr Gly Met Gly Val Val Glu Asp Lys Val Ile Lys Asn His Tyr Ala
65                  70                  75                  80

Ser Glu Tyr Ile Tyr Asn Ala Tyr Lys Asn Thr Lys Thr Cys Gly Val
                85                  90                  95

Ile Glu Glu Asp Pro Ala Phe Gly Ile Lys Lys Ile Ala Glu Pro Leu
            100                 105                 110

Gly Val Ile Ala Ala Val Ile Pro Thr Thr Asn Pro Thr Ser Thr Ala
        115                 120                 125

Ile Phe Lys Thr Leu Ile Ala Leu Lys Thr Arg Asn Ala Ile Ile Ile
    130                 135                 140

Ser Pro His Pro Arg Ala Lys Asn Ser Thr Ile Glu Ala Ala Lys Ile
145                 150                 155                 160

Val Leu Glu Ala Ala Val Lys Ala Gly Ala Pro Glu Gly Ile Ile Gly
                165                 170                 175

Trp Ile Asp Val Pro Ser Leu Glu Leu Thr Asn Leu Val Met Arg Glu
            180                 185                 190

Ala Asp Val Ile Leu Ala Thr Gly Gly Pro Gly Leu Val Lys Ala Ala
        195                 200                 205

Tyr Ser Ser Gly Lys Pro Ala Ile Gly Val Gly Ala Gly Asn Thr Pro
    210                 215                 220

Ala Ile Ile Asp Asp Ser Ala Asp Ile Val Leu Ala Val Asn Ser Ile
225                 230                 235                 240

Ile His Ser Lys Thr Phe Asp Asn Gly Met Ile Cys Ala Ser Glu Gln
                245                 250                 255

Ser Val Ile Val Leu Asp Gly Val Tyr Lys Glu Val Lys Lys Glu Phe
            260                 265                 270

Glu Lys Arg Gly Cys Tyr Phe Leu Asn Glu Asp Glu Thr Glu Lys Val
        275                 280                 285

Arg Lys Thr Ile Ile Ile Asn Gly Ala Leu Asn Ala Lys Ile Val Gly
    290                 295                 300
```

```
Gln Lys Ala His Thr Ile Ala Asn Leu Ala Gly Phe Glu Val Pro Glu
305                 310                 315                 320

Thr Thr Lys Ile Leu Ile Gly Glu Val Thr Ser Val Asp Ile Ser Glu
                325                 330                 335

Glu Phe Ala His Glu Lys Leu Cys Pro Val Leu Ala Met Tyr Arg Ala
            340                 345                 350

Lys Asp Phe Asp Asp Ala Leu Asp Lys Ala Glu Arg Leu Val Ala Asp
        355                 360                 365

Gly Gly Phe Gly His Thr Ser Ser Leu Tyr Ile Asp Thr Val Thr Gln
    370                 375                 380

Lys Glu Lys Leu Gln Lys Phe Ser Glu Arg Met Lys Thr Cys Arg Ile
385                 390                 395                 400

Leu Val Asn Thr Pro Ser Ser Gln Gly Gly Ile Gly Asp Leu Tyr Asn
                405                 410                 415

Phe Lys Leu Ala Pro Ser Leu Thr Leu Gly Cys Gly Ser Trp Gly Gly
            420                 425                 430

Asn Ser Val Ser Asp Asn Val Gly Val Lys His Leu Leu Asn Ile Lys
        435                 440                 445

Thr Val Ala Glu Arg Arg Glu Asn Met Leu Trp Phe Arg Thr Pro Glu
    450                 455                 460

Lys Ile Tyr Ile Lys Arg Gly Cys Leu Pro Val Ala Leu Asp Glu Leu
465                 470                 475                 480

Lys Asn Val Met Gly Lys Lys Lys Ala Phe Ile Val Thr Gly Asn Phe
                485                 490                 495

Leu Tyr Asn Asn Gly Tyr Thr Lys Pro Ile Thr Asp Lys Leu Asp Glu
            500                 505                 510

Met Gly Ile Val His Lys Thr Phe Phe Asp Val Ser Pro Asp Pro Ser
        515                 520                 525

Leu Ala Ser Ala Lys Ala Gly Ala Ala Glu Met Leu Ala Phe Gln Pro
    530                 535                 540

Asp Thr Ile Ile Ala Val Gly Gly Gly Ser Ala Met Asp Ala Ala Lys
545                 550                 555                 560

Ile Met Trp Val Met Tyr Glu His Pro Glu Val Asp Phe Met Asp Met
                565                 570                 575

Ala Met Arg Phe Met Asp Ile Arg Lys Arg Val Tyr Thr Phe Pro Lys
            580                 585                 590

Met Gly Gln Lys Ala Tyr Phe Ile Ala Ile Pro Thr Ser Ala Gly Thr
        595                 600                 605

Gly Ser Glu Val Thr Pro Phe Ala Val Ile Thr Asp Glu Lys Thr Gly
    610                 615                 620

Ile Lys Tyr Pro Leu Ala Asp Tyr Glu Leu Leu Pro Asp Met Ala Ile
625                 630                 635                 640

Val Asp Ala Asp Met Met Met Asn Ala Pro Lys Gly Leu Thr Ala Ala
                645                 650                 655

Ser Gly Ile Asp Ala Leu Thr His Ala Leu Glu Ala Tyr Val Ser Met
            660                 665                 670

Leu Ala Thr Asp Tyr Thr Asp Ser Leu Ala Leu Arg Ala Ile Lys Met
        675                 680                 685

Ile Phe Glu Tyr Leu Pro Arg Ala Tyr Glu Asn Gly Ala Ser Asp Pro
    690                 695                 700

Val Ala Arg Glu Lys Met Ala Asn Ala Ala Thr Ile Ala Gly Met Ala
705                 710                 715                 720

Phe Ala Asn Ala Phe Leu Gly Val Cys His Ser Met Ala His Lys Leu
```

```
                725                 730                 735

Gly Ala Phe Tyr His Leu Pro His Gly Val Ala Asn Ala Leu Met Ile
            740                 745                 750

Asn Glu Val Ile Arg Phe Asn Ser Ser Glu Ala Pro Thr Lys Met Gly
        755                 760                 765

Thr Phe Pro Gln Tyr Asp His Pro Arg Thr Leu Glu Arg Tyr Ala Glu
    770                 775                 780

Ile Ala Asp Tyr Ile Gly Leu Lys Gly Lys Asn Asn Glu Glu Lys Val
785                 790                 795                 800

Glu Asn Leu Ile Lys Ala Ile Asp Glu Leu Lys Glu Lys Val Gly Ile
            805                 810                 815

Arg Lys Thr Ile Lys Asp Tyr Asp Ile Asp Glu Lys Glu Phe Leu Asp
            820                 825                 830

Arg Leu Asp Glu Met Val Glu Gln Ala Phe Asp Asp Gln Cys Thr Gly
        835                 840                 845

Thr Asn Pro Arg Tyr Pro Leu Met Asn Glu Ile Arg Gln Met Tyr Leu
    850                 855                 860

Asn Ala Tyr Tyr Gly Gly Ala Lys Lys
865                 870
```

<210> SEQ ID NO 22
<211> LENGTH: 957
<212> TYPE: DNA
<213> ORGANISM: C.thermocellum

<400> SEQUENCE: 22

```
atggaaatgg taaaaagtag gtcaaaagtt gcaatcattg gtgctggttt tgtaggtgcg      60

tctgcagcct tcacaatggc tttgcggcaa accgcaaatg aacttgttct catcgatgtt     120

ttcaaggaaa aagccatagg cgaggctatg gatattaacc acggtcttcc atttatggga     180

cagatgtcat tgtatgccgg tgattattcc gacgttaaag actgtgatgt tatcgtagtc     240

acggccggag ccaacagaaa acctggtgaa acacgtcttg accttgcaaa gaaaaacgtt     300

atgattgcaa aagaagtaac tcaaaacatc atgaagtatt acaaccatgg tgtaatactt     360

gtagtatcca atcctgttga cattataact tatatgatcc aaaaatggtc aggcctccct     420

gtgggaaaag ttataggttc aggtaccgta cttgacagta tcagattcag atacttgtta     480

agcgaaaaat tgggcgttga cgtaaagaat gtacacggct acataatagg cgaacacggt     540

gattcacagc ttccgttgtg gagctgcaca catatcgccg gtaaaaatat caacgaatat     600

atcgatgatc cgaaatgcaa tttcacagaa gaagacaaga aaaaaatcgc tgaagatgtt     660

aaaactgcgg gtgcaaccat tatcaagaac aaaggtgcaa catactatgg tattgcagtt     720

tcaatcaaca caatagttga aacactcctt aagaatcaga atacaataag aaccgtagga     780

accgttataa acggcatgta tggaatagaa gatgttgcaa taagccttcc atccatcgta     840

aattccgaag gtgttcagga agttctccaa tttaatctga ctcctgaaga agaagaagct     900

ttaagattct cagcggagca ggttaaaaaa gtattgaacg aagttaagaa tttataa       957
```

<210> SEQ ID NO 23
<211> LENGTH: 318
<212> TYPE: PRT
<213> ORGANISM: C.thermocellum

<400> SEQUENCE: 23

```
Met Glu Met Val Lys Ser Arg Ser Lys Val Ala Ile Ile Gly Ala Gly
1               5                   10                  15
```

```
Phe Val Gly Ala Ser Ala Ala Phe Thr Met Ala Leu Arg Gln Thr Ala
            20                  25                  30

Asn Glu Leu Val Leu Ile Asp Val Phe Lys Glu Lys Ala Ile Gly Glu
        35                  40                  45

Ala Met Asp Ile Asn His Gly Leu Pro Phe Met Gly Gln Met Ser Leu
    50                  55                  60

Tyr Ala Gly Asp Tyr Ser Asp Val Lys Asp Cys Asp Val Ile Val Val
65                  70                  75                  80

Thr Ala Gly Ala Asn Arg Lys Pro Gly Glu Thr Arg Leu Asp Leu Ala
                85                  90                  95

Lys Lys Asn Val Met Ile Ala Lys Glu Val Thr Gln Asn Ile Met Lys
            100                 105                 110

Tyr Tyr Asn His Gly Val Ile Leu Val Val Ser Asn Pro Val Asp Ile
        115                 120                 125

Ile Thr Tyr Met Ile Gln Lys Trp Ser Gly Leu Pro Val Gly Lys Val
    130                 135                 140

Ile Gly Ser Gly Thr Val Leu Asp Ser Ile Arg Phe Arg Tyr Leu Leu
145                 150                 155                 160

Ser Glu Lys Leu Gly Val Asp Val Lys Asn Val His Gly Tyr Ile Ile
                165                 170                 175

Gly Glu His Gly Asp Ser Gln Leu Pro Leu Trp Ser Cys Thr His Ile
            180                 185                 190

Ala Gly Lys Asn Ile Asn Glu Tyr Ile Asp Asp Pro Lys Cys Asn Phe
        195                 200                 205

Thr Glu Glu Asp Lys Lys Lys Ile Ala Glu Asp Val Lys Thr Ala Gly
    210                 215                 220

Ala Thr Ile Ile Lys Asn Lys Gly Ala Thr Tyr Tyr Gly Ile Ala Val
225                 230                 235                 240

Ser Ile Asn Thr Ile Val Glu Thr Leu Leu Lys Asn Gln Asn Thr Ile
                245                 250                 255

Arg Thr Val Gly Thr Val Ile Asn Gly Met Tyr Gly Ile Glu Asp Val
            260                 265                 270

Ala Ile Ser Leu Pro Ser Ile Val Asn Ser Glu Gly Val Gln Glu Val
        275                 280                 285

Leu Gln Phe Asn Leu Thr Pro Glu Glu Glu Glu Ala Leu Arg Phe Ser
    290                 295                 300

Ala Glu Gln Val Lys Lys Val Leu Asn Glu Val Lys Asn Leu
305                 310                 315
```

<210> SEQ ID NO 24
<211> LENGTH: 942
<212> TYPE: DNA
<213> ORGANISM: Methanocaldococcus jannaschii

<400> SEQUENCE: 24

```
atgaaagtta caattatagg agcttctggt agagttggga gtgcaacagc cttattatta      60

gctaaagaac cttttatgaa ggatttggtg ttaattggaa gagaacattc aataaataaa     120

ttggaaggat tgagagaaga catctacgat gccttagctg ggacaagaag tgatgcaaat     180

atatacgttg agagtgatga aaatctaagg ataattgatg aaagtgatgt tgttataata     240

acaagcggtg ttccaagaaa agagggaatg agtaggatgg atttggcaaa aacaaatgca     300

aaaattgttg ggaagtatgc taaaaaaata gctgaaatct gcgatacaaa aatatttgtt     360

ataacaaacc ctgtggatgt gatgacttat aaagctctgg tagattcaaa atttgaaaga     420
```

```
aatcaagttt ttggattagg gactcattta gattctttga ggtttaaggt tgctattgct    480

aagtttttcg gtgttcatat tgatgaagtt aggacgagaa ttattggaga gcatggggac    540

agcatggttc cattgttaag tgctacctct atcggaggaa ttcctattca aaaatttgaa    600

agatttaagg aactgccaat agatgagatt atagaggatg ttaaaacaaa aggagagcag    660

attattagat tgaaaggagg ttctgagttt ggtccagcag cagccatttt aaatgttgtt    720

aggtgtattg tgaataatga gaaaagattg ctaactttat ccgcttacgt agatggagag    780

tttgatggaa ttagagatgt gtgtattgga gttccagtaa agattggaag agatgggata    840

gaagaggttg tatcaattga attggataaa gatgagataa ttgcatttag aaaatctgct    900

gaaatcatta aaaaatactg tgaagaagtt aaaaacttat aa                       942
```

```
<210> SEQ ID NO 25
<211> LENGTH: 313
<212> TYPE: PRT
<213> ORGANISM: Methanocaldococcus jannaschii

<400> SEQUENCE: 25

Met Lys Val Thr Ile Ile Gly Ala Ser Gly Arg Val Gly Ser Ala Thr
1               5                   10                  15

Ala Leu Leu Leu Ala Lys Glu Pro Phe Met Lys Asp Leu Val Leu Ile
            20                  25                  30

Gly Arg Glu His Ser Ile Asn Lys Leu Glu Gly Leu Arg Glu Asp Ile
        35                  40                  45

Tyr Asp Ala Leu Ala Gly Thr Arg Ser Asp Ala Asn Ile Tyr Val Glu
    50                  55                  60

Ser Asp Glu Asn Leu Arg Ile Ile Asp Glu Ser Asp Val Val Ile Ile
65                  70                  75                  80

Thr Ser Gly Val Pro Arg Lys Glu Gly Met Ser Arg Met Asp Leu Ala
                85                  90                  95

Lys Thr Asn Ala Lys Ile Val Gly Lys Tyr Ala Lys Lys Ile Ala Glu
            100                 105                 110

Ile Cys Asp Thr Lys Ile Phe Val Ile Thr Asn Pro Val Asp Val Met
        115                 120                 125

Thr Tyr Lys Ala Leu Val Asp Ser Lys Phe Glu Arg Asn Gln Val Phe
    130                 135                 140

Gly Leu Gly Thr His Leu Asp Ser Leu Arg Phe Lys Val Ala Ile Ala
145                 150                 155                 160

Lys Phe Phe Gly Val His Ile Asp Glu Val Arg Thr Arg Ile Ile Gly
                165                 170                 175

Glu His Gly Asp Ser Met Val Pro Leu Leu Ser Ala Thr Ser Ile Gly
            180                 185                 190

Gly Ile Pro Ile Gln Lys Phe Glu Arg Phe Lys Glu Leu Pro Ile Asp
        195                 200                 205

Glu Ile Ile Glu Asp Val Lys Thr Lys Gly Glu Gln Ile Ile Arg Leu
    210                 215                 220

Lys Gly Gly Ser Glu Phe Gly Pro Ala Ala Ala Ile Leu Asn Val Val
225                 230                 235                 240

Arg Cys Ile Val Asn Asn Glu Lys Arg Leu Leu Thr Leu Ser Ala Tyr
                245                 250                 255

Val Asp Gly Glu Phe Asp Gly Ile Arg Asp Val Cys Ile Gly Val Pro
            260                 265                 270

Val Lys Ile Gly Arg Asp Gly Ile Glu Glu Val Val Ser Ile Glu Leu
```

```
        275                 280                 285

Asp Lys Asp Glu Ile Ile Ala Phe Arg Lys Ser Ala Glu Ile Ile Lys
    290                 295                 300

Lys Tyr Cys Glu Glu Val Lys Asn Leu
305                 310
```

<210> SEQ ID NO 26
<211> LENGTH: 1203
<212> TYPE: DNA
<213> ORGANISM: Pseudomonas sp.

<400> SEQUENCE: 26

```
atggcaaaag tattatgtgt attatatgat gatccagtag atggatatcc aaaaacatat     60

gcaagagatg atttaccaaa aatagatcat tatccaggag gacaaacatt accaacacca    120

aaagcaatag attttacacc aggacaatta ttaggatcag tatcaggaga attaggatta    180

agaaaatatt tagaatcaaa tggacataca ttagtagtaa catcagataa agatggacca    240

gattcagtat ttgaaagaga attagtagat gcagatgtag taatatcaca accattttgg    300

ccagcatatt taacaccaga aagaatagca aaagcaaaaa atttaaaatt agcattaaca    360

gcaggaatag gatcagatca tgtagattta caatcagcaa tagatagaaa tgtaacagta    420

gcagaagtaa catattgtaa ttcaatatca gtagcagaac atgtagtaat gatgatatta    480

tcattagtaa gaaattattt accatcacat gaatgggcaa gaaaaggagg atggaatata    540

gcagattgtg tatcacatgc atatgattta gaagcaatgc atgtaggaac agtagcagca    600

ggaagaatag gattagcagt attaagaaga ttagcaccat ttgatgtaca tttacattat    660

acagatagac atagattacc agaatcagta gaaaaagaat taaatttaac atggcatgca    720

acaagagaag atatgtatcc agtatgtgat gtagtaacat taaattgtcc attacatcca    780

gaaacagaac atatgataaa tgatgaaaca ttaaaattat ttaaaagagg agcatatata    840

gtaaatacag caagaggaaa attatgtgat agagatgcag tagcaagagc attagaatca    900

ggaagattag caggatatgc aggagatgta tggtttccac aaccagcacc aaaagatcat    960

ccatggagaa caatgccata taatggaatg acaccacata tatcaggaac aacattaaca   1020

gcacaagcaa gatatgcagc aggaacaaga gaaatattag aatgtttttt tgaaggaaga   1080

ccaataagag atgaatattt aatagtacaa ggaggagcat tagcaggaac aggagcacat   1140

tcatattcaa aaggaaatgc aacaggagga tcagaagaag cagcaaaatt taaaaaagca   1200

gta                                                                 1203
```

<210> SEQ ID NO 27
<211> LENGTH: 401
<212> TYPE: PRT
<213> ORGANISM: Pseudomonas sp.

<400> SEQUENCE: 27

```
Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Thr Leu Pro Thr Pro Lys Ala Ile Asp Phe Thr Pro Gly
        35                  40                  45

Gln Leu Leu Gly Ser Val Ser Gly Glu Leu Gly Leu Arg Lys Tyr Leu
    50                  55                  60

Glu Ser Asn Gly His Thr Leu Val Val Thr Ser Asp Lys Asp Gly Pro
```

```
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Asp Arg His
    210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Val
```

<210> SEQ ID NO 28
<211> LENGTH: 2700
<212> TYPE: DNA
<213> ORGANISM: Moorella thermoaceticum

<400> SEQUENCE: 28

```
atggttaacc tgaccattga cggacaaagg gttacggctc cagagggcat gaccatcctg     60

gaggtggccc gggaaaatgg tatccatatc cccaccctgt gccaccatcc aaagttgcgg    120

cccctggggt attgccgtct gtgcctggtc gacatcgagg gcgccgcaaa acccatgacg    180

gcctgcaata cgccggtcgc cgagggtatg gtgatccgga ccagcacgcc tgttatagag    240
```

```
gagatgcgca agggtattat tgaaatgctt ttaagcctcc acccggagga ctgcctgacc    300
tgcgaaaaag caggtaactg ccagctccag gattgcgcct acacttacgg tgtaaagcat    360
ggcgaactgc cagtaaaacg cgaggaattg cccgttttga aggaaaatcc cttcattgtg    420
cgggattata ataaatgtat cgtttgcggc cgttgcgtcc gcgcctgcca ggaggtgcag    480
gtccagaggg tcgtggacct ggtgggtaaa ggcagcgccg cccgggtggg ggcgacgaag    540
gccggagcgg aagtaagcct ggaagaaggg ggctgcgtct tttgcggtaa ctgtgtccag    600
gtctgcccgg tgggagctct gacggagaag gccggcctgg gccagggccg cgagtgggag    660
ttcaaaaaag tccgcagtat ttgttcttac tgcggcgtgg gttgtaatct cacccttat    720
gtaaaagatg gtaaggtggt aaaagttagg ggttacgaaa accctgaggt aaacaacggc    780
tggctgtgcg taaaaggccg ctttggtttt gactatattc acaatcctga caggataacc    840
aggccgttga tccgggaggg agatagggaa aaaggctatt tccgggaggc ttcctgggaa    900
gaagctttag cccttgtatc ccagaaatta actcagatta aaggcagcta cggctctgaa    960
gctctgggct ttctttgttc agctaaatgt accaatgaag agaattatct cttacaaaag   1020
ctggcccggg gggtactggg caccaataat gttgatcact gtgctcgcct ccactcttct   1080
acagttgccg gtctggcaac aacctttggc agcggtgcaa tgaccaattc tatcgctgac   1140
atcgccagcg cagattgtat ctttgtcatt ggcagcaata caaccgagaa ccatcctgtt   1200
attgccctta aagtaaaaga agctgtccgt cgtggagcca ggctcattgt tgctgatccc   1260
cggcgtattg aactggtgaa cttcagttac ttgtggttaa gacaaaaacc cggaacagat   1320
cttgctctgc tgaatggact gcttcatgta atcatcaagg aagagcttta tgacaaagaa   1380
tttattgccc agaggacgga aggttttgag gctctaaaac ttgccgtaga ggagtataca   1440
ccagcaaagg tgtcagaagt tacaggtgtt ccggcaggcg atattatcga ggcagcaagg   1500
acttatgccc ggggtccgag ctctactatt ttgtacgcaa tgggaataac ccagcatata   1560
actggtacgg ccaacgtgat ggccctggcc aacctggcca tggcctgtgg tcaggtcggt   1620
aaagaaggta gcggcgtaaa tcccctgcgg gggcagagca atgtccaggg tgcctgcgat   1680
atgggtggat tacccaatgt attaccggga taccaaccag taacagatcc gggggttcgc   1740
cataaattta gcgaagcctg gggggtaccg gacttacccg gagaacctgg cctgacatta   1800
atggagatga tggcggcagc ccaagaaggc aaattgaaag ggatgtatat tttaggagaa   1860
aaccctgtct tgactgatcc agatgtctcc catgtaaaag aggcgttaaa gaacctggag   1920
tttctggtgg tacaggatat ttttttgacg gagacagcca ggatggcgga tgttgtttta   1980
cctggagctt cctttgcgga aaaggaaggt acctttacca gtacggagcg ccgggtgcag   2040
cttttgcata aagccattga acctcccggt gaagcacggc cggattggct tattttaaac   2100
gatttgttgc tgttaatggg atatccgcgg aaatattcgt cgcctgggga gataatgcag   2160
gagatagcag ggttaactcc cagctatgcg ggtataactt atgagcgcct ggaagataaa   2220
gggttacagt ggccggtgct ttccctcgaa catccgggta cacccgttct ccatcgggaa   2280
aaatttagca gaggttatgg gcagttccag gtagtgcatt accggccgcc ggccgaagaa   2340
cctgatgagg agtacccgtt cttatttacc actggcagga atttgtatca ctatcatact   2400
gttatttccc gtaagtccag gggggctggaa gagatgtgtc ctgctcctgt ggtggagatt   2460
aatgataacg atgcagcccg tttgggtata cgggaaggag aaatgattga gattgtttcc   2520
cgacgtggta aagtaagggt taaagcattg gttacggatc gcataccccg gggccaggta   2580
```

```
tttatgaatt tccatttcca tgaagcagca gccaacctgc ttacaattgc tgccctggat   2640

ccggttgcta aaatacccga gtataaaacc tgtgctgtag ctatcaaggt taaaaagtag   2700


<210> SEQ ID NO 29
<211> LENGTH: 899
<212> TYPE: PRT
<213> ORGANISM: Moorella thermoaceticum

<400> SEQUENCE: 29

Met Val Asn Leu Thr Ile Asp Gly Gln Arg Val Thr Ala Pro Glu Gly
1               5                   10                  15

Met Thr Ile Leu Glu Val Ala Arg Glu Asn Gly Ile His Ile Pro Thr
            20                  25                  30

Leu Cys His His Pro Lys Leu Arg Pro Leu Gly Tyr Cys Arg Leu Cys
        35                  40                  45

Leu Val Asp Ile Glu Gly Ala Ala Lys Pro Met Thr Ala Cys Asn Thr
    50                  55                  60

Pro Val Ala Glu Gly Met Val Ile Arg Thr Ser Thr Pro Val Ile Glu
65                  70                  75                  80

Glu Met Arg Lys Gly Ile Ile Glu Met Leu Leu Ser Leu His Pro Glu
                85                  90                  95

Asp Cys Leu Thr Cys Glu Lys Ala Gly Asn Cys Gln Leu Gln Asp Cys
            100                 105                 110

Ala Tyr Thr Tyr Gly Val Lys His Gly Glu Leu Pro Val Lys Arg Glu
        115                 120                 125

Glu Leu Pro Val Leu Lys Glu Asn Pro Phe Ile Val Arg Asp Tyr Asn
    130                 135                 140

Lys Cys Ile Val Cys Gly Arg Cys Val Arg Ala Cys Gln Glu Val Gln
145                 150                 155                 160

Val Gln Arg Val Val Asp Leu Val Gly Lys Gly Ser Ala Ala Arg Val
                165                 170                 175

Gly Ala Thr Lys Ala Gly Ala Glu Val Ser Leu Glu Glu Gly Gly Cys
            180                 185                 190

Val Phe Cys Gly Asn Cys Val Gln Val Cys Pro Val Gly Ala Leu Thr
        195                 200                 205

Glu Lys Ala Gly Leu Gly Gln Gly Arg Glu Trp Glu Phe Lys Lys Val
    210                 215                 220

Arg Ser Ile Cys Ser Tyr Cys Gly Val Gly Cys Asn Leu Thr Leu Tyr
225                 230                 235                 240

Val Lys Asp Gly Lys Val Val Lys Val Arg Gly Tyr Glu Asn Pro Glu
                245                 250                 255

Val Asn Asn Gly Trp Leu Cys Val Lys Gly Arg Phe Gly Phe Asp Tyr
            260                 265                 270

Ile His Asn Pro Asp Arg Ile Thr Arg Pro Leu Ile Arg Glu Gly Asp
        275                 280                 285

Arg Glu Lys Gly Tyr Phe Arg Glu Ala Ser Trp Glu Glu Ala Leu Ala
    290                 295                 300

Leu Val Ser Gln Lys Leu Thr Gln Ile Lys Gly Ser Tyr Gly Ser Glu
305                 310                 315                 320

Ala Leu Gly Phe Leu Cys Ser Ala Lys Cys Thr Asn Glu Glu Asn Tyr
                325                 330                 335

Leu Leu Gln Lys Leu Ala Arg Gly Val Leu Gly Thr Asn Asn Val Asp
            340                 345                 350

His Cys Ala Arg Leu His Ser Ser Thr Val Ala Gly Leu Ala Thr Thr
```

```
        355                 360                 365

Phe Gly Ser Gly Ala Met Thr Asn Ser Ile Ala Asp Ile Ala Ser Ala
    370                 375                 380

Asp Cys Ile Phe Val Ile Gly Ser Asn Thr Thr Glu Asn His Pro Val
385                 390                 395                 400

Ile Ala Leu Lys Val Lys Glu Ala Val Arg Arg Gly Ala Arg Leu Ile
                405                 410                 415

Val Ala Asp Pro Arg Arg Ile Glu Leu Val Asn Phe Ser Tyr Leu Trp
            420                 425                 430

Leu Arg Gln Lys Pro Gly Thr Asp Leu Ala Leu Leu Asn Gly Leu Leu
        435                 440                 445

His Val Ile Ile Lys Glu Glu Leu Tyr Asp Lys Glu Phe Ile Ala Gln
    450                 455                 460

Arg Thr Glu Gly Phe Glu Ala Leu Lys Leu Ala Val Glu Glu Tyr Thr
465                 470                 475                 480

Pro Ala Lys Val Ser Glu Val Thr Gly Val Pro Ala Gly Asp Ile Ile
                485                 490                 495

Glu Ala Ala Arg Thr Tyr Ala Arg Gly Pro Ser Ser Thr Ile Leu Tyr
            500                 505                 510

Ala Met Gly Ile Thr Gln His Ile Thr Gly Thr Ala Asn Val Met Ala
        515                 520                 525

Leu Ala Asn Leu Ala Met Ala Cys Gly Gln Val Gly Lys Glu Gly Ser
    530                 535                 540

Gly Val Asn Pro Leu Arg Gly Gln Ser Asn Val Gln Gly Ala Cys Asp
545                 550                 555                 560

Met Gly Gly Leu Pro Asn Val Leu Pro Gly Tyr Gln Pro Val Thr Asp
                565                 570                 575

Pro Gly Val Arg His Lys Phe Ser Glu Ala Trp Gly Val Pro Asp Leu
            580                 585                 590

Pro Gly Glu Pro Gly Leu Thr Leu Met Glu Met Met Ala Ala Ala Gln
        595                 600                 605

Glu Gly Lys Leu Lys Gly Met Tyr Ile Leu Gly Glu Asn Pro Val Leu
    610                 615                 620

Thr Asp Pro Asp Val Ser His Val Lys Glu Ala Leu Lys Asn Leu Glu
625                 630                 635                 640

Phe Leu Val Val Gln Asp Ile Phe Leu Thr Glu Thr Ala Arg Met Ala
                645                 650                 655

Asp Val Val Leu Pro Gly Ala Ser Phe Ala Glu Lys Glu Gly Thr Phe
            660                 665                 670

Thr Ser Thr Glu Arg Arg Val Gln Leu Leu His Lys Ala Ile Glu Pro
        675                 680                 685

Pro Gly Glu Ala Arg Pro Asp Trp Leu Ile Leu Asn Asp Leu Leu Leu
    690                 695                 700

Leu Met Gly Tyr Pro Arg Lys Tyr Ser Ser Pro Gly Glu Ile Met Gln
705                 710                 715                 720

Glu Ile Ala Gly Leu Thr Pro Ser Tyr Ala Gly Ile Thr Tyr Glu Arg
                725                 730                 735

Leu Glu Asp Lys Gly Leu Gln Trp Pro Val Leu Ser Leu Glu His Pro
            740                 745                 750

Gly Thr Pro Val Leu His Arg Glu Lys Phe Ser Arg Gly Tyr Gly Gln
        755                 760                 765

Phe Gln Val Val His Tyr Arg Pro Pro Ala Glu Glu Pro Asp Glu Glu
    770                 775                 780
```

```
Tyr Pro Phe Leu Phe Thr Thr Gly Arg Asn Leu Tyr His Tyr His Thr
785                 790                 795                 800

Val Ile Ser Arg Lys Ser Arg Gly Leu Glu Glu Met Cys Pro Ala Pro
                805                 810                 815

Val Val Glu Ile Asn Asp Asn Asp Ala Ala Arg Leu Gly Ile Arg Glu
            820                 825                 830

Gly Glu Met Ile Glu Ile Val Ser Arg Arg Gly Lys Val Arg Val Lys
        835                 840                 845

Ala Leu Val Thr Asp Arg Ile Pro Arg Gly Gln Val Phe Met Asn Phe
    850                 855                 860

His Phe His Glu Ala Ala Ala Asn Leu Leu Thr Ile Ala Ala Leu Asp
865                 870                 875                 880

Pro Val Ala Lys Ile Pro Glu Tyr Lys Thr Cys Ala Val Ala Ile Lys
                885                 890                 895

Val Lys Lys


<210> SEQ ID NO 30
<211> LENGTH: 2124
<212> TYPE: DNA
<213> ORGANISM: Moorella thermoaceticum

<400> SEQUENCE: 30

ttgggagagg tggtatttag cacctgggga ggaaaagttg tcgatcaccg gggcggtccg     60

tcggggggag gaccgtcctg ggccggggaa tttggcggtc ggcagttaaa ggcctttatt    120

ggctgggatg gtctcgtagt caccgacccg gccgtagacc tgctggctgc tttacaggct    180

tactaccagg ccgtccaggg ggaatcctgc ggccgctgcg taccctgccg ggtagggacc    240

agggttattt acaatgtcct ggtacgcatc gccgggggcg aaggccttcc ctccgattta    300

gaccttctcc gacgggtggc ctggattgta cgggatggtt ctctgtgcga gctcggccag    360

gctggggcca aagctgttct tgattttta gattattata gcgaggcctt gcgacctttc    420

ctggaggata gcggcagggt cgccgggggt caacggagac cagggcctgg aggccgggtg    480

caggttctgg cttccggacg ggtcctggtg gggaacgacc gcggaaaggg agcggccgcc    540

gcttccccgg cagccggttt aacctataaa ccttttgtta ctgcgccctg cctcaagcgg    600

tgcccggccc acctggacat cccggcttat attgacgcca ttaaggatgg ccgctatgag    660

gaatccctgg ccatcatccg ccagcggacc gccctggccg gtgtcctggg acgggtctgc    720

gtccacccgt gtgaagaaaa ctgccgccgc ggcaatgttg acgaacccct ggccatccgg    780

ggcctgaagc gcttcgtagc cgattatgag gtgaaacgcg gccgccggcc ggtcgccgtc    840

tgcgggggta atctctttac gggaccctgg cggccggcag gacaggccgg tggggaagaa    900

acaacggccg tcacttcagg caagaaggta gccatcatcg gtgccggacc ggcgggtctc    960

agcgccgcct accagctcgc cggtcggggc tataaagtga ctattttcga ggccttgccg   1020

gtggccggcg gtatgctggc ggtgggtatt cccagctacc ggttgccacg ggatatcctg   1080

gctggagaga tcgaggccat caaggctctg ggcgtaacca tcaacctcaa cacccgggtc   1140

ggcgtcgacg tgaccatgga ccaattacag cgcgattacg acgccgtctt tattgctacc   1200

ggcctccatg ccagctcccg catgggagta gccggcgagg atgaaggcta tggaggattt   1260

atccccgggg tcaagttcct gcgagatttg aacctggacc ggtgtccttc cctggagggc   1320

aaggtggtgg ccgtcgtcgg cggcggcaat gtagcgatgg attgcgcccg ttccgccctg   1380

cgccgggggg cccgggaggt gcaccttatt taccggcgtt cccgggcgga aatgccggcc   1440
```

```
catgcgaccg aggtcaggga tgccgaggcc gagggggtta tttatcactt cctggttaat   1500

cccaccgccc tggtagcgga aaaaggcaat atcaagggta tgcagtgcgt ccggatgaaa   1560

cttggcgagc cggacgattc tggccggcgc cggcccgtac ccgtgccggg aacggagttt   1620

ttcctgccct gcgatattgt ggtgccggct atcggccagg cggccgacct gtctttcctg   1680

gacggccgga tcgaggtggg caaacgtggt accatcagtg ttgacccggt gaccctggct   1740

accagtgtcc ccggcgtctt cgccggcggc gatatcgtcc tgggggccag gacggtagtt   1800

gaggccgtgg cccagggcaa ccgggcggca gtttccattg accagtacct gcgccagggg   1860

accaccagtc ccacggtaga ggacgagctg gacgcgtggc tggaaaaggt cggcgtctat   1920

gacccggaag aggatgtagg aatctacggc ggccggccgc ggcaggcaga aagggtggcg   1980

ccgttggccg agcgggtaaa ggacttccgg gaagttgaag gcggcttcga tttctacgca   2040

ggcagggccg aagccgaacg ctgcctgcgc tgttaccggg tcgggatgat ggtcctggcc   2100

ggagaggggg agagtaatgg ttaa                                          2124
```

```
<210> SEQ ID NO 31
<211> LENGTH: 707
<212> TYPE: PRT
<213> ORGANISM: Moorella thermoaceticum

<400> SEQUENCE: 31

Met Gly Glu Val Val Phe Ser Thr Trp Gly Gly Lys Val Val Asp His
1               5                   10                  15

Arg Gly Gly Pro Ser Gly Gly Gly Pro Ser Trp Ala Gly Glu Phe Gly
            20                  25                  30

Gly Arg Gln Leu Lys Ala Phe Ile Gly Trp Asp Gly Leu Val Val Thr
        35                  40                  45

Asp Pro Ala Val Asp Leu Leu Ala Ala Leu Gln Ala Tyr Tyr Gln Ala
    50                  55                  60

Val Gln Gly Glu Ser Cys Gly Arg Cys Val Pro Cys Arg Val Gly Thr
65                  70                  75                  80

Arg Val Ile Tyr Asn Val Leu Val Arg Ile Ala Gly Gly Glu Gly Leu
                85                  90                  95

Pro Ser Asp Leu Asp Leu Leu Arg Arg Val Ala Trp Ile Val Arg Asp
            100                 105                 110

Gly Ser Leu Cys Glu Leu Gly Gln Ala Gly Ala Lys Ala Val Leu Asp
        115                 120                 125

Phe Leu Asp Tyr Tyr Ser Glu Ala Leu Arg Pro Phe Leu Glu Asp Ser
    130                 135                 140

Gly Arg Val Ala Gly Gly Gln Arg Arg Pro Gly Pro Gly Gly Arg Val
145                 150                 155                 160

Gln Val Leu Ala Ser Gly Arg Val Leu Val Gly Asn Asp Arg Gly Lys
                165                 170                 175

Gly Ala Ala Ala Ala Ser Pro Ala Ala Gly Leu Thr Tyr Lys Pro Phe
            180                 185                 190

Val Thr Ala Pro Cys Leu Lys Arg Cys Pro Ala His Leu Asp Ile Pro
        195                 200                 205

Ala Tyr Ile Asp Ala Ile Lys Asp Gly Arg Tyr Glu Glu Ser Leu Ala
    210                 215                 220

Ile Ile Arg Gln Arg Thr Ala Leu Ala Gly Val Leu Gly Arg Val Cys
225                 230                 235                 240

Val His Pro Cys Glu Glu Asn Cys Arg Arg Gly Asn Val Asp Glu Pro
```

```
                245                 250                 255

Leu Ala Ile Arg Gly Leu Lys Arg Phe Val Ala Asp Tyr Glu Val Lys
            260                 265                 270

Arg Gly Arg Arg Pro Val Ala Val Cys Gly Gly Asn Leu Phe Thr Gly
        275                 280                 285

Pro Trp Arg Pro Ala Gly Gln Ala Gly Gly Glu Glu Thr Thr Ala Val
    290                 295                 300

Thr Ser Gly Lys Lys Val Ala Ile Ile Gly Ala Gly Pro Ala Gly Leu
305                 310                 315                 320

Ser Ala Ala Tyr Gln Leu Ala Gly Arg Gly Tyr Lys Val Thr Ile Phe
                325                 330                 335

Glu Ala Leu Pro Val Ala Gly Gly Met Leu Ala Val Gly Ile Pro Ser
            340                 345                 350

Tyr Arg Leu Pro Arg Asp Ile Leu Ala Gly Glu Ile Glu Ala Ile Lys
        355                 360                 365

Ala Leu Gly Val Thr Ile Asn Leu Asn Thr Arg Val Gly Val Asp Val
    370                 375                 380

Thr Met Asp Gln Leu Gln Arg Asp Tyr Asp Ala Val Phe Ile Ala Thr
385                 390                 395                 400

Gly Leu His Ala Ser Ser Arg Met Gly Val Ala Gly Glu Asp Glu Gly
                405                 410                 415

Tyr Gly Gly Phe Ile Pro Gly Val Lys Phe Leu Arg Asp Leu Asn Leu
            420                 425                 430

Asp Arg Cys Pro Ser Leu Glu Gly Lys Val Val Ala Val Val Gly Gly
        435                 440                 445

Gly Asn Val Ala Met Asp Cys Ala Arg Ser Ala Leu Arg Arg Gly Ala
    450                 455                 460

Arg Glu Val His Leu Ile Tyr Arg Arg Ser Arg Ala Glu Met Pro Ala
465                 470                 475                 480

His Ala Thr Glu Val Arg Asp Ala Glu Ala Glu Gly Val Ile Tyr His
                485                 490                 495

Phe Leu Val Asn Pro Thr Ala Leu Val Ala Glu Lys Gly Asn Ile Lys
            500                 505                 510

Gly Met Gln Cys Val Arg Met Lys Leu Gly Glu Pro Asp Asp Ser Gly
        515                 520                 525

Arg Arg Arg Pro Val Pro Val Pro Gly Thr Glu Phe Phe Leu Pro Cys
    530                 535                 540

Asp Ile Val Val Pro Ala Ile Gly Gln Ala Ala Asp Leu Ser Phe Leu
545                 550                 555                 560

Asp Gly Arg Ile Glu Val Gly Lys Arg Gly Thr Ile Ser Val Asp Pro
                565                 570                 575

Val Thr Leu Ala Thr Ser Val Pro Gly Val Phe Ala Gly Gly Asp Ile
            580                 585                 590

Val Leu Gly Ala Arg Thr Val Val Glu Ala Val Ala Gln Gly Asn Arg
        595                 600                 605

Ala Ala Val Ser Ile Asp Gln Tyr Leu Arg Gln Gly Thr Thr Ser Pro
    610                 615                 620

Thr Val Glu Asp Glu Leu Asp Ala Trp Leu Glu Lys Val Gly Val Tyr
625                 630                 635                 640

Asp Pro Glu Glu Asp Val Gly Ile Tyr Gly Gly Arg Pro Arg Gln Ala
                645                 650                 655

Glu Arg Val Ala Pro Leu Ala Glu Arg Val Lys Asp Phe Arg Glu Val
            660                 665                 670
```

```
Glu Gly Gly Phe Asp Phe Tyr Ala Gly Arg Ala Glu Ala Glu Arg Cys
        675                 680                 685

Leu Arg Cys Tyr Arg Val Gly Met Met Val Leu Ala Gly Glu Gly Glu
    690                 695                 700

Ser Asn Gly
705


<210> SEQ ID NO 32
<211> LENGTH: 1173
<212> TYPE: DNA
<213> ORGANISM: C.thermocellum

<400> SEQUENCE: 32

atggattaca gaaaagaatc actaaggctt cacggtgagt ggaagggtaa aattgaggtt      60

atacacaagg tacctgtttc aaccaaggaa gagttgtcgc ttgcttatac accgggtgtt     120

gcagaaccat gtcttgcaat tcagaaagat gttaatcttt cttatgaata tacaagacgt     180

tggaacctgg tagcggttat taccgacggt acggcggttt tagggctcgg agacatagga     240

cctgaagccg gaatgcctgt tatggaaggt aaatgcgtac tcttcaagag gtttggtgat     300

gtggacgcat ttccgctctg tatcaaatca aaagacgtag atgaaattgt aaaagacaatc    360

aagctcatct ccggaagctt tggcggtata aacctcgaag atatatccgc tccgagatgc     420

tttgaaatag aaagaagact caaagaggaa tgtgacattc caatattcca tgatgaccag     480

cacggtacag ccgttgttac tgttgcagca atgatcaatg cattaaagct tgtcaacaag     540

aaaatcgagg atatagaagt tgttgtaaac ggttcaggtg ctgccggcat agctgtaaca     600

agactgctca tgagtatggg gcttaagaaa gttatccttt gcgataccaa aggtgcaatt     660

tatgatggaa gagacaactt aaacagtgaa aaagccctga ttgctaaaat ctcgaacctc     720

gagaaaaaga aaggtactct tgaagatgta atcaagggag ctgacgtatt catcggtctt     780

tccgttccag gaacagttac aaaggatatg gtaaaatcca tggcaaagga tccgattatc     840

tttgctatgg caaatcctac tcctgaaata atgcctgatg aagcaaaaga agcaggagca     900

aaggtagtgg gtaccggaag atccgacttc ccgaaccaga taaacaacgt tcttgcgttc     960

cccggaatat tcagaggtgc gcttgatgta agagcaagag atatcaatga tgaaatgaag    1020

atagccgctg caaaagcaat agcttctctg gtaagcgatg aagagctcaa tcctgacttc    1080

attcttccgc tcccatttga cccaagagtc ggaaaaacag ttgctgcagc agttgctgaa    1140

gcagcaagaa aaaccggagt tgcaagaata taa                                 1173


<210> SEQ ID NO 33
<211> LENGTH: 390
<212> TYPE: PRT
<213> ORGANISM: C.thermocellum

<400> SEQUENCE: 33

Met Asp Tyr Arg Lys Glu Ser Leu Arg Leu His Gly Glu Trp Lys Gly
1               5                   10                  15

Lys Ile Glu Val Ile His Lys Val Pro Val Ser Thr Lys Glu Glu Leu
            20                  25                  30

Ser Leu Ala Tyr Thr Pro Gly Val Ala Glu Pro Cys Leu Ala Ile Gln
        35                  40                  45

Lys Asp Val Asn Leu Ser Tyr Glu Tyr Thr Arg Arg Trp Asn Leu Val
    50                  55                  60

Ala Val Ile Thr Asp Gly Thr Ala Val Leu Gly Leu Gly Asp Ile Gly
```

```
65                  70                  75                  80

Pro Glu Ala Gly Met Pro Val Met Glu Gly Lys Cys Val Leu Phe Lys
                85                  90                  95

Arg Phe Gly Asp Val Asp Ala Phe Pro Leu Cys Ile Lys Ser Lys Asp
            100                 105                 110

Val Asp Glu Ile Val Lys Thr Ile Lys Leu Ile Ser Gly Ser Phe Gly
        115                 120                 125

Gly Ile Asn Leu Glu Asp Ile Ser Ala Pro Arg Cys Phe Glu Ile Glu
    130                 135                 140

Arg Arg Leu Lys Glu Glu Cys Asp Ile Pro Ile Phe His Asp Asp Gln
145                 150                 155                 160

His Gly Thr Ala Val Val Thr Val Ala Ala Met Ile Asn Ala Leu Lys
                165                 170                 175

Leu Val Asn Lys Lys Ile Glu Asp Ile Glu Val Val Val Asn Gly Ser
            180                 185                 190

Gly Ala Ala Gly Ile Ala Val Thr Arg Leu Leu Met Ser Met Gly Leu
        195                 200                 205

Lys Lys Val Ile Leu Cys Asp Thr Lys Gly Ala Ile Tyr Asp Gly Arg
    210                 215                 220

Asp Asn Leu Asn Ser Glu Lys Ala Leu Ile Ala Lys Ile Ser Asn Leu
225                 230                 235                 240

Glu Lys Lys Lys Gly Thr Leu Glu Asp Val Ile Lys Gly Ala Asp Val
                245                 250                 255

Phe Ile Gly Leu Ser Val Pro Gly Thr Val Thr Lys Asp Met Val Lys
            260                 265                 270

Ser Met Ala Lys Asp Pro Ile Ile Phe Ala Met Ala Asn Pro Thr Pro
        275                 280                 285

Glu Ile Met Pro Asp Glu Ala Lys Glu Ala Gly Ala Lys Val Val Gly
    290                 295                 300

Thr Gly Arg Ser Asp Phe Pro Asn Gln Ile Asn Asn Val Leu Ala Phe
305                 310                 315                 320

Pro Gly Ile Phe Arg Gly Ala Leu Asp Val Arg Ala Arg Asp Ile Asn
                325                 330                 335

Asp Glu Met Lys Ile Ala Ala Ala Lys Ala Ile Ala Ser Leu Val Ser
            340                 345                 350

Asp Glu Glu Leu Asn Pro Asp Phe Ile Leu Pro Leu Pro Phe Asp Pro
        355                 360                 365

Arg Val Gly Lys Thr Val Ala Ala Ala Val Ala Glu Ala Ala Arg Lys
    370                 375                 380

Thr Gly Val Ala Arg Ile
385                 390


<210> SEQ ID NO 34
<211> LENGTH: 1622
<212> TYPE: DNA
<213> ORGANISM: Geobacillus stearothermophilus

<400> SEQUENCE: 34

ctgcagaaag gggcatgtac aataagggtt gtctttttcc ggttcatagg ataacatttg      60

taccgtaaga tgatttactg atttaaacaa aaatagagaa aaggaaggac gattggttat     120

ggcattacca ggcggggcag ccatgaacat tacgattcgt ctccagttcg aaaaagatat     180

cgtctcattc agcgatatcg ccgccgcgat tggcaaagcg ggcggggaca ttgtcgggat     240

tgacgtcatt tcgtcaagca aagttcacac ggtgcgcgat attaccgtca gcgccctcga     300
```

```
tacgaagcag tgcgacttga tcattgaggc gctgaaaaaa attcgcggcg tcaaaattgt    360
gaacgtttcc gaccgcacgt ttttgatgca catcgggggg aaaattgaaa caaattcaaa    420
aatcccagtg aaaacacgcg acgacttgtc gcgggtatac acgccgggcg tggcgcgcgt    480
ctgcacggcg attgccgaag atccgcgaaa ggcgtattcg ctgacgatta aacggaatac    540
ggtcgccgtt gtctcggacg gcacggcggt gcttgggctt ggcgacatcg gtccgtacgc    600
ggcgatgcca gtcatggaag ggaaagcgat gctgtttaag gaatttgccg gagtggacgc    660
gttcccgatt tgtttggata cgaaagacac ggaagaaatc attcaaattg tgaaagcgat    720
cgccccggcg tttggcggca ttaacctgga ggacatttcc gccccacgtt gttttgaaat    780
tgaaaagcgg ctgaaagaag agctggatat tcccgtgttt catgatgacc agcatggcac    840
ggcggtcgtg ctcttggcgg gactgcttaa cgcgctgaaa atcgttgaca aaaagctcga    900
agacattaaa gtcgtcttaa ccggcatcgg tgcggccggc atcgcctgca cgaaaatttt    960
gcttgcggcc ggcgtgcgca acattatcgg ggtcgaccgc catggcgcca tccaccgcga   1020
tgaaacgtac gaaaatccgt actggcaaga gtatgcgcaa ctcacgaacc cggataatct   1080
gaaaggaagc ttgtccgatg tcatcgccgg cgcagatgta tttatcggcg tttcggctcc   1140
gggcatttta aaagtggaag atgtgaaaaa aatggcgcgc gatccgatcg tgtttgcgat   1200
ggccaacccg attccggaaa ttgatccgga gctggccgaa ccgtacgtgc gcgtcatggc   1260
gaccgggcgt tccgactatc cgaaccaaat caacaacgtc ctttgcttcc cgggcatttt   1320
ccgcggggcg cttgactgcc gggcgagaga aattaacgag gaaatgaagc tcgctgccgc   1380
gaaggcgatt gcctctgtcg tgacggagga tgaattgaac gaaacataca tcatcccgag   1440
cgtcttcaac agcaaagtcg tcgaacgcgt cagacaagcg gtcgtcgaag cggcttaccg   1500
cactggggtg gcgcggaagg acaatatccc ggttggcgga tatacagggc agtaaagcaa   1560
ggaatgcgat ggaaccgacg gacggcttcc tttatagggg aagccgtttt ttttggctgc   1620
ag                                                                  1622
```

<210> SEQ ID NO 35
<211> LENGTH: 1011
<212> TYPE: DNA
<213> ORGANISM: C. thermocellum

<400> SEQUENCE: 35

```
atggcagtaa aaattggtat caacggtttt ggacgtatcg gtcgtcttgt gttcagggcc     60
agtctcaaca acccgaacgt tgaggttgta ggtataaacg acccatttat tgaccttgaa    120
tacatgcaat atatgttaaa gtatgataca gtacatggtc agttcaaagg tgaaatttca    180
caagacaacg gaaaactcgt tgtaaacggc agaaaaataa gtgtttatgg tttcactgat    240
cctgctgaga ttccgtggag cgaatgcggt gcggaataca tcgttgaatc aacgggtgta    300
ttcacaacta ctgaaaaggc ttcagctcac ttcaagggcg gtgcaaagaa ggtagttatc    360
agtgctcctt cggcagatgc tccgatgttt gttatgggtg taaaccatga taaatacaca    420
aaggatatga acgttgtatc taacgcttca tgtacaacaa actgccttgc tcctctggct    480
aaagttatac atgaaaactt cggaatcgta gaaggcttga tgactactgt acacgctaca    540
actgcaactc aaaagactgt tgacggtcct tcaaagaaag actggagagg cggacgtgca    600
gcagcaggca acatcattcc ttcatcaaca ggagctgcaa aggcagttgg aaaggttatc    660
cctgaattga acggtaagtt gacaggtatg gctttcagag ttccgactct tgacgtatct    720
```

```
gttgttgact tgacttgccg tcttgaaaaa ccggctactt atgatgaaat caaagccgct    780

gttaagaaag cttcagaaaa tgaacttaag ggtattttgg gatacactga ggatgcggtt    840

gtttcttcag acttcatcgg cgatccccgc acttcaattt tcgatgctga agcaggtatt    900

tctctcaaca gcaactttgt aaaacttgtt gcctggtacg acaatgaatg gggttattca    960

aacaaagttg ttgatttgat agttcatatg gcttcggttg atgcaaaata a            1011
```

<210> SEQ ID NO 36
<211> LENGTH: 336
<212> TYPE: PRT
<213> ORGANISM: C. thermocellum

<400> SEQUENCE: 36

```
Met Ala Val Lys Ile Gly Ile Asn Gly Phe Gly Arg Ile Gly Arg Leu
1               5                   10                  15

Val Phe Arg Ala Ser Leu Asn Asn Pro Asn Val Glu Val Val Gly Ile
            20                  25                  30

Asn Asp Pro Phe Ile Asp Leu Glu Tyr Met Gln Tyr Met Leu Lys Tyr
        35                  40                  45

Asp Thr Val His Gly Gln Phe Lys Gly Glu Ile Ser Gln Asp Asn Gly
    50                  55                  60

Lys Leu Val Val Asn Gly Arg Lys Ile Ser Val Tyr Gly Phe Thr Asp
65                  70                  75                  80

Pro Ala Glu Ile Pro Trp Ser Glu Cys Gly Ala Glu Tyr Ile Val Glu
                85                  90                  95

Ser Thr Gly Val Phe Thr Thr Thr Glu Lys Ala Ser Ala His Phe Lys
            100                 105                 110

Gly Gly Ala Lys Lys Val Val Ile Ser Ala Pro Ser Ala Asp Ala Pro
        115                 120                 125

Met Phe Val Met Gly Val Asn His Asp Lys Tyr Thr Lys Asp Met Asn
    130                 135                 140

Val Val Ser Asn Ala Ser Cys Thr Thr Asn Cys Leu Ala Pro Leu Ala
145                 150                 155                 160

Lys Val Ile His Glu Asn Phe Gly Ile Val Glu Gly Leu Met Thr Thr
                165                 170                 175

Val His Ala Thr Thr Ala Thr Gln Lys Thr Val Asp Gly Pro Ser Lys
            180                 185                 190

Lys Asp Trp Arg Gly Gly Arg Ala Ala Ala Gly Asn Ile Ile Pro Ser
        195                 200                 205

Ser Thr Gly Ala Ala Lys Ala Val Gly Lys Val Ile Pro Glu Leu Asn
    210                 215                 220

Gly Lys Leu Thr Gly Met Ala Phe Arg Val Pro Thr Leu Asp Val Ser
225                 230                 235                 240

Val Val Asp Leu Thr Cys Arg Leu Glu Lys Pro Ala Thr Tyr Asp Glu
                245                 250                 255

Ile Lys Ala Ala Val Lys Lys Ala Ser Glu Asn Glu Leu Lys Gly Ile
            260                 265                 270

Leu Gly Tyr Thr Glu Asp Ala Val Val Ser Ser Asp Phe Ile Gly Asp
        275                 280                 285

Pro Arg Thr Ser Ile Phe Asp Ala Glu Ala Gly Ile Ser Leu Asn Ser
    290                 295                 300

Asn Phe Val Lys Leu Val Ala Trp Tyr Asp Asn Glu Trp Gly Tyr Ser
305                 310                 315                 320

Asn Lys Val Val Asp Leu Ile Val His Met Ala Ser Val Asp Ala Lys
```

325 330 335

<210> SEQ ID NO 37
<211> LENGTH: 2229
<212> TYPE: DNA
<213> ORGANISM: C.thermocellum

<400> SEQUENCE: 37

```
atggatgcat ggcgcggatt taataaaggc aactggtgcc aggaaattga cgttcgtgat     60
tttataatta gaaattatac tccttatgaa ggcgatgaaa gctttcttgt aggacctacg    120
gatagaacgc ggaaactttg ggagaaggtt tccgaactgt taaagaaaga acgggagaac    180
ggcggggtat tggatgttga tacccataca atttcaacga ttacgtctca taaacctgga    240
tatatagata aagaacttga agttattgtc gggcttcaga cggatgagcc tttaaaaaga    300
gccataatgc cgtttggcgg tatacgtatg gtgattaagg gagccgaagc ttatggccac    360
agtgtggacc ctcaggttgt tgaaatattc acaaagtaca gaaagactca taaccaggga    420
gtttatgatg tatatactcc cgaaatgaga aaagccaaaa aagccgggat tattacagga    480
cttcccgacg catacggcag aggaagaata attggcgatt acagaagggt tgcactttat    540
ggcgttgaca ggctgattgc tgaaaaagag aaagaaatgg caagtcttga aagagattac    600
attgactatg agactgttcg agacagagaa gaaataagcg agcagattaa atctttaaaa    660
caacttaaag aaatggcttt aagttacggt tttgacatat cttgtcctgc aaaggatgcc    720
agagaagcct ttcaatggtt gtattttgca tatcttgcag cagtcaagga acagaacggc    780
gcggcaatga gtattggaag aatttcgact ttccttgaca tatacattga aagggatctc    840
aaagaaggaa aactcacgga ggagttggct caggaactgg ttgaccagct ggttataaag    900
ctgagaattg tgagattttt gagaactcct gagtatgaaa agctcttcag cggagacccc    960
acttgggtaa ccgaaagtat cggaggtatg gcgctggatg gaagaacgct ggttacaaaa   1020
tcttcgttca ggtttttgca cactcttttc aacctgggac atgcaccgga gcccaacctt   1080
acagtacttt ggtccgtcaa tcttcccgaa ggctttaaaa agtactgtgc aaaggtatca   1140
attcattcaa gctccatcca gtatgaaagc gacgacataa tgaggaaaca ctggggagac   1200
gattatggaa tagcatgctg tgtttctgct atgagaattg gaaaacagat gcagttcttc   1260
ggtgcaagat gcaatcttgc aaaagctctt ctttacgcta ttaacggcgg aaaggatgaa   1320
atgacgggag aacagattgc tccgatgttt gcaccggtgg aaaccgaata ccttgattac   1380
gaggacgtaa tgaagaggtt tgacatggtg cttgactggg tggcaaggct ttatatgaac   1440
accctcaata taattcacta catgcatgac aaatatgcct atgaggcgct gcagatggca   1500
ttgcatgaca aagacgtgtt caggacgatg gcatgcggaa tagccggttt gtctgtggtg   1560
gcagactccc ttagcgcgat aaaatatgca aaggttaaac cgatacgcaa tgaaaacaac   1620
ctcgttgttg actacgaagt tgagggtgat tatcctaaat tcggaaataa cgacgaacgt   1680
gttgatgaaa ttgcagtgca agtagtaaaa atgttcatga acaagcttag aaagcaaagg   1740
gcttacagaa gtgccactcc gaccctttcc atacttacca taacttcaaa cgtggtatat   1800
ggaaagaaaa ccggaaacac tcctgacggc agaaaagctg gagaaccttt ggcgccggga   1860
gcaaatccga tgcatggaag ggatataaac ggagcattgg ctgtactgaa cagtattgcg   1920
aagcttccct atgaatatgc ccaggacggc atttcatata ctttctccat aattccaaaa   1980
gctctgggaa gagacgagga aaccagaata aacaatctta aatcaatgct tgacggatat   2040
ttcaagcagg gcggccacca cataaatgta aatgtgtttg aaaaagagac actgttagat   2100
```

```
gccatggaac atccggaaaa atatccacaa cttaccataa gagtgtccgg gtatgcagtg   2160

aactttataa agcttacacg ggagcaacag ctggatgtta ttaacagaac gattcacgga   2220

aagatttaa                                                           2229


<210> SEQ ID NO 38
<211> LENGTH: 742
<212> TYPE: PRT
<213> ORGANISM: C.thermocellum

<400> SEQUENCE: 38

Met Asp Ala Trp Arg Gly Phe Asn Lys Gly Asn Trp Cys Gln Glu Ile
1               5                   10                  15

Asp Val Arg Asp Phe Ile Ile Arg Asn Tyr Thr Pro Tyr Glu Gly Asp
            20                  25                  30

Glu Ser Phe Leu Val Gly Pro Thr Asp Arg Thr Arg Lys Leu Trp Glu
        35                  40                  45

Lys Val Ser Glu Leu Leu Lys Lys Glu Arg Glu Asn Gly Gly Val Leu
    50                  55                  60

Asp Val Asp Thr His Thr Ile Ser Thr Ile Thr Ser His Lys Pro Gly
65                  70                  75                  80

Tyr Ile Asp Lys Glu Leu Glu Val Ile Val Gly Leu Gln Thr Asp Glu
                85                  90                  95

Pro Leu Lys Arg Ala Ile Met Pro Phe Gly Gly Ile Arg Met Val Ile
            100                 105                 110

Lys Gly Ala Glu Ala Tyr Gly His Ser Val Asp Pro Gln Val Val Glu
        115                 120                 125

Ile Phe Thr Lys Tyr Arg Lys Thr His Asn Gln Gly Val Tyr Asp Val
    130                 135                 140

Tyr Thr Pro Glu Met Arg Lys Ala Lys Lys Ala Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Arg Leu Ile Ala Glu Lys Glu Lys Glu
            180                 185                 190

Met Ala Ser Leu Glu Arg Asp Tyr Ile Asp Tyr Glu Thr Val Arg Asp
        195                 200                 205

Arg Glu Glu Ile Ser Glu Gln Ile Lys Ser Leu Lys Gln Leu Lys Glu
    210                 215                 220

Met Ala Leu Ser Tyr Gly Phe Asp Ile Ser Cys Pro Ala Lys Asp Ala
225                 230                 235                 240

Arg Glu Ala Phe Gln Trp Leu Tyr Phe Ala Tyr Leu Ala Ala Val Lys
                245                 250                 255

Glu Gln Asn Gly Ala Ala Met Ser Ile Gly Arg Ile Ser Thr Phe Leu
            260                 265                 270

Asp Ile Tyr Ile Glu Arg Asp Leu Lys Glu Gly Lys Leu Thr Glu Glu
        275                 280                 285

Leu Ala Gln Glu Leu Val Asp Gln Leu Val Ile Lys Leu Arg Ile Val
    290                 295                 300

Arg Phe Leu Arg Thr Pro Glu Tyr Glu Lys Leu Phe Ser Gly Asp Pro
305                 310                 315                 320

Thr Trp Val Thr Glu Ser Ile Gly Gly Met Ala Leu Asp Gly Arg Thr
                325                 330                 335

Leu Val Thr Lys Ser Ser Phe Arg Phe Leu His Thr Leu Phe Asn Leu
```

```
            340                 345                 350

Gly His Ala Pro Glu Pro Asn Leu Thr Val Leu Trp Ser Val Asn Leu
        355                 360                 365

Pro Glu Gly Phe Lys Lys Tyr Cys Ala Lys Val Ser Ile His Ser Ser
    370                 375                 380

Ser Ile Gln Tyr Glu Ser Asp Asp Ile Met Arg Lys His Trp Gly Asp
385                 390                 395                 400

Asp Tyr Gly Ile Ala Cys Cys Val Ser Ala Met Arg Ile Gly Lys Gln
                405                 410                 415

Met Gln Phe Phe Gly Ala Arg Cys Asn Leu Ala Lys Ala Leu Leu Tyr
            420                 425                 430

Ala Ile Asn Gly Gly Lys Asp Glu Met Thr Gly Glu Gln Ile Ala Pro
        435                 440                 445

Met Phe Ala Pro Val Glu Thr Glu Tyr Leu Asp Tyr Glu Asp Val Met
    450                 455                 460

Lys Arg Phe Asp Met Val Leu Asp Trp Val Ala Arg Leu Tyr Met Asn
465                 470                 475                 480

Thr Leu Asn Ile Ile His Tyr Met His Asp Lys Tyr Ala Tyr Glu Ala
                485                 490                 495

Leu Gln Met Ala Leu His Asp Lys Asp Val Phe Arg Thr Met Ala Cys
            500                 505                 510

Gly Ile Ala Gly Leu Ser Val Val Ala Asp Ser Leu Ser Ala Ile Lys
        515                 520                 525

Tyr Ala Lys Val Lys Pro Ile Arg Asn Glu Asn Asn Leu Val Val Asp
    530                 535                 540

Tyr Glu Val Glu Gly Asp Tyr Pro Lys Phe Gly Asn Asn Asp Glu Arg
545                 550                 555                 560

Val Asp Glu Ile Ala Val Gln Val Val Lys Met Phe Met Asn Lys Leu
                565                 570                 575

Arg Lys Gln Arg Ala Tyr Arg Ser Ala Thr Pro Thr Leu Ser Ile Leu
            580                 585                 590

Thr Ile Thr Ser Asn Val Val Tyr Gly Lys Lys Thr Gly Asn Thr Pro
        595                 600                 605

Asp Gly Arg Lys Ala Gly Glu Pro Leu Ala Pro Gly Ala Asn Pro Met
    610                 615                 620

His Gly Arg Asp Ile Asn Gly Ala Leu Ala Val Leu Asn Ser Ile Ala
625                 630                 635                 640

Lys Leu Pro Tyr Glu Tyr Ala Gln Asp Gly Ile Ser Tyr Thr Phe Ser
                645                 650                 655

Ile Ile Pro Lys Ala Leu Gly Arg Asp Glu Glu Thr Arg Ile Asn Asn
            660                 665                 670

Leu Lys Ser Met Leu Asp Gly Tyr Phe Lys Gln Gly Gly His His Ile
        675                 680                 685

Asn Val Asn Val Phe Glu Lys Glu Thr Leu Leu Asp Ala Met Glu His
    690                 695                 700

Pro Glu Lys Tyr Pro Gln Leu Thr Ile Arg Val Ser Gly Tyr Ala Val
705                 710                 715                 720

Asn Phe Ile Lys Leu Thr Arg Glu Gln Gln Leu Asp Val Ile Asn Arg
                725                 730                 735

Thr Ile His Gly Lys Ile
            740
```

<210> SEQ ID NO 39

<211> LENGTH: 717
<212> TYPE: DNA
<213> ORGANISM: C.thermocellum

<400> SEQUENCE: 39

```
atgacattaa agggcaggat acactcattt gaatcttttg ggacactgga cggaccgggt     60

ataagatttg tggttttcat gcagggctgt cccttgcgtt gtatatattg ccacaacagg    120

gatacctggg atgttaatgc ggggagtgag tacactcccc ggcaagtaat tgatgaaatg    180

atgaaataca tagactatat aaaggtctcc ggaggcggaa taactgttac cggcggggag    240

cctgttctcc aggccgattt tgtggccgag gtgttcagac ttgcaaaaga gcagggagtg    300

catacggcgc tggataccaa tggatttgct gacatagaga aggttgaaag gcttataaaa    360

tacaccgatc ttgtattgct ggatataaag catgcccggg aggataaaca taagataatt    420

accggtgtgt ccaacgaaaa aatcaagcgt tttgcgctgt atctttcgga ccagggagtg    480

cctatctgga taagatatgt ccttgtcccc ggatataccg acgatgaaga tgaccttaaa    540

atggcggctg atttcataaa aaagcttaaa acggtggaaa aaatcgaagt tcttccttat    600

cacaacatgg gagcatacaa atgggaaaaa cttggtcaga aatacatgct tgaaggagta    660

aaggggccga gtgcgcaaga ggtggaaaaa gcaaagagga ttctgtcagg caaataa       717
```

<210> SEQ ID NO 40
<211> LENGTH: 238
<212> TYPE: PRT
<213> ORGANISM: C.thermocellum

<400> SEQUENCE: 40

```
Met Thr Leu Lys Gly Arg Ile His Ser Phe Glu Ser Phe Gly Thr Leu
1               5                   10                  15

Asp Gly Pro Gly Ile Arg Phe Val Val Phe Met Gln Gly Cys Pro Leu
            20                  25                  30

Arg Cys Ile Tyr Cys His Asn Arg Asp Thr Trp Asp Val Asn Ala Gly
        35                  40                  45

Ser Glu Tyr Thr Pro Arg Gln Val Ile Asp Glu Met Met Lys Tyr Ile
    50                  55                  60

Asp Tyr Ile Lys Val Ser Gly Gly Gly Ile Thr Val Thr Gly Gly Glu
65                  70                  75                  80

Pro Val Leu Gln Ala Asp Phe Val Ala Glu Val Phe Arg Leu Ala Lys
                85                  90                  95

Glu Gln Gly Val His Thr Ala Leu Asp Thr Asn Gly Phe Ala Asp Ile
            100                 105                 110

Glu Lys Val Glu Arg Leu Ile Lys Tyr Thr Asp Leu Val Leu Leu Asp
        115                 120                 125

Ile Lys His Ala Arg Glu Asp Lys His Lys Ile Ile Thr Gly Val Ser
    130                 135                 140

Asn Glu Lys Ile Lys Arg Phe Ala Leu Tyr Leu Ser Asp Gln Gly Val
145                 150                 155                 160

Pro Ile Trp Ile Arg Tyr Val Leu Val Pro Gly Tyr Thr Asp Asp Glu
                165                 170                 175

Asp Asp Leu Lys Met Ala Ala Asp Phe Ile Lys Lys Leu Lys Thr Val
            180                 185                 190

Glu Lys Ile Glu Val Leu Pro Tyr His Asn Met Gly Ala Tyr Lys Trp
        195                 200                 205

Glu Lys Leu Gly Gln Lys Tyr Met Leu Glu Gly Val Lys Gly Pro Ser
    210                 215                 220
```

Ala Gln Glu Val Glu Lys Ala Lys Arg Ile Leu Ser Gly Lys
225 230 235

<210> SEQ ID NO 41
<211> LENGTH: 2652
<212> TYPE: DNA
<213> ORGANISM: C.thermocellum

<400> SEQUENCE: 41

```
atggcaaagt atgtgtattt gtttagtgaa ggcaatgcat caatgagaga cctgcttgga     60
ggaaaaggtg ccaatcttgc agaaatgaca agtttgggac ttccggtacc cagaggtttt    120
accattacca cggaagcttg tacacgctac tatcaagatg gaaaagtcat tgccaaggaa    180
atagaagatg aaatatacag aactatggag aagcttgaag agattgtcgg gaagaaattc    240
ggtgacccat caaatccgtt tcttgtttcc gttcgttccg gtgccagagt atcaatgccc    300
ggtatgatgg ataccatatt aaatctcgga cttaatgatg aagttgttgt aggtcttgca    360
aagcttacca ataatgaaag attcgcatat gacagctata gaagatttat tcaaatgttc    420
agcgatgttg tcatggaggt ggaaaagtcc aagtttgaag ctattcttga tgctgtgaaa    480
gaagaaaaca actgtgaaaa tgactgcgac ctttctgccg aaaatttaaa ggaagtagtc    540
agaagataca aggagctgtt caagaaagaa aagggatttg attttccgca ggatccgaaa    600
acacagttga tggaagccgt aaaagccgtt ttccgttcat gggaaaatcc aagggctatt    660
gtatatagaa gattaaatga catccccggc gactggggta ctgcagttaa cgttcaggaa    720
atggtttatg gaaatatggg aaatgattcg ggtacgggag ttgcctttac aaggaacccg    780
gctacgggag aaaagaagct ttatggtgaa ttccttatga atgcccaggg agaagacgtt    840
gttgcaggta tcagaactcc ccagtcaatt gaccagctga aagaagtaat gcctgatgta    900
tacaatcagt ttgtggagat agccgaaaaa cttgaaagac attatagaga tatgcaggat    960
atggagttta caattgaaag aggaaaactc ttcatgctcc agacaagaaa cggtaaaagg   1020
actgctgcgg ctgctttaaa aatagctgtt gatttggtaa atgagggaat ggtcacaaaa   1080
gaagaagcaa ttttaaaagt cgacccgaaa cagcttgata cactgctcca tccaaatttc   1140
gaaccttcag cgctgaaaaa tgcaaaacct atagcaaagg gattgccggc ttcaccggga   1200
gctgctaccg gaaagattta ctttagagcc gaggatgcgg tggaagcggc caaaaacgga   1260
gaaaaagaca tcattcttgt aagacttgaa acttcacccg aagatattga gggtatgcat   1320
gtatccaaag gaatacttac aggccgtggt ggaatgacat ctcatgctgc agttgttgca   1380
cgcggtatgg gtacttgctg cgttgccggc tgcagtgaaa taagaataaa tgaggaagag   1440
aaatactttg tagataaaaa cggaaagaaa tatgttgagg gtgattggat ttcccttgac   1500
ggttccacag gtaatgttta tggggaaaag cttcctacag tggagcctga aatgaccggc   1560
gactttgcca cacttatgca gtgggccgat gaaatcagaa ctcttaagat tagaaccaat   1620
gccgatactc cggctgatgc catccaggca agaaagttcg gtgcggaagg tatcggactt   1680
tgccgtacgg agcatatgtt cttcgattct gacagaattc cggcaatgag agaaatgata   1740
gttgcaagaa ccgaagaaca gagaagaaag gctttggata aactcctgcc gatgcagaga   1800
aaagattttg aagaactgtt tactgcaatg gaaggctatc ctgtgacgat cagattcctg   1860
gatcctccgc ttcatgagtt cctgccccag gaggatgaag acatagaagc cttggcaaaa   1920
gaaatgggaa ttactttcga tgaactgaaa gcaatagtaa ccgggcttca tgagttcaat   1980
cctatgatgg gacacagggg atgccgtctt gcagtcacat atccggaaat tgcggaaatg   2040
```

```
cagacgagag cggttattga agctgctatc aacgtgagca ggaagaatat aaaagttgtg   2100

cctgaaatta tgattccgtt ggtaggcgat gtcaaggagc tgaaatatgt caaggacgta   2160

gttgtcagaa cagccaatga attgattgaa aaatccggtg tgaagattga atataaagtc   2220

ggaaccatga tagaaattcc aagggcggcc attactgccg atgaaattgc aaaagaagct   2280

gaattcttct cctttggaac caacgacctg acccagatga cttttggatt cagccgtgac   2340

gatgcaggca agttccttga agaatactac aacaagaaga tatacgagtt cgatcctttt   2400

gcaaaactgg atcaggatgg agtggggaaa ctggttgaaa tggctgcgaa gcttggaaga   2460

caaacaagac cggatattaa gcttggtata tgcggtgaac atggcggaga tccgtcgtcc   2520

attgagttct gccaccaaat tgggctgaac tatgtatcat gctctccgtt ccgtgtgccg   2580

attgcaaggc ttgcagcggc tcaggcaaga gtaaatgaaa taaaaggtac aaaggatttg   2640

ggacagaaat aa                                                       2652


<210> SEQ ID NO 42
<211> LENGTH: 883
<212> TYPE: PRT
<213> ORGANISM: C.thermocellum

<400> SEQUENCE: 42

Met Ala Lys Tyr Val Tyr Leu Phe Ser Glu Gly Asn Ala Ser Met Arg
1               5                   10                  15

Asp Leu Leu Gly Gly Lys Gly Ala Asn Leu Ala Glu Met Thr Ser Leu
            20                  25                  30

Gly Leu Pro Val Pro Arg Gly Phe Thr Ile Thr Thr Glu Ala Cys Thr
        35                  40                  45

Arg Tyr Tyr Gln Asp Gly Lys Val Ile Ala Lys Glu Ile Glu Asp Glu
    50                  55                  60

Ile Tyr Arg Thr Met Glu Lys Leu Glu Glu Ile Val Gly Lys Lys Phe
65                  70                  75                  80

Gly Asp Pro Ser Asn Pro Phe Leu Val Ser Val Arg Ser Gly Ala Arg
                85                  90                  95

Val Ser Met Pro Gly Met Met Asp Thr Ile Leu Asn Leu Gly Leu Asn
            100                 105                 110

Asp Glu Val Val Val Gly Leu Ala Lys Leu Thr Asn Asn Glu Arg Phe
        115                 120                 125

Ala Tyr Asp Ser Tyr Arg Arg Phe Ile Gln Met Phe Ser Asp Val Val
    130                 135                 140

Met Glu Val Glu Lys Ser Lys Phe Glu Ala Ile Leu Asp Ala Val Lys
145                 150                 155                 160

Glu Glu Asn Asn Cys Glu Asn Asp Cys Asp Leu Ser Ala Glu Asn Leu
                165                 170                 175

Lys Glu Val Val Arg Arg Tyr Lys Glu Leu Phe Lys Lys Glu Lys Gly
            180                 185                 190

Phe Asp Phe Pro Gln Asp Pro Lys Thr Gln Leu Met Glu Ala Val Lys
        195                 200                 205

Ala Val Phe Arg Ser Trp Glu Asn Pro Arg Ala Ile Val Tyr Arg Arg
    210                 215                 220

Leu Asn Asp Ile Pro Gly Asp Trp Gly Thr Ala Val Asn Val Gln Glu
225                 230                 235                 240

Met Val Tyr Gly Asn Met Gly Asn Asp Ser Gly Thr Gly Val Ala Phe
                245                 250                 255
```

```
Thr Arg Asn Pro Ala Thr Gly Glu Lys Lys Leu Tyr Gly Glu Phe Leu
            260                 265                 270

Met Asn Ala Gln Gly Glu Asp Val Val Ala Gly Ile Arg Thr Pro Gln
        275                 280                 285

Ser Ile Asp Gln Leu Lys Glu Val Met Pro Asp Val Tyr Asn Gln Phe
    290                 295                 300

Val Glu Ile Ala Glu Lys Leu Glu Arg His Tyr Arg Asp Met Gln Asp
305                 310                 315                 320

Met Glu Phe Thr Ile Glu Arg Gly Lys Leu Phe Met Leu Gln Thr Arg
                325                 330                 335

Asn Gly Lys Arg Thr Ala Ala Ala Ala Leu Lys Ile Ala Val Asp Leu
            340                 345                 350

Val Asn Glu Gly Met Val Thr Lys Glu Glu Ala Ile Leu Lys Val Asp
        355                 360                 365

Pro Lys Gln Leu Asp Thr Leu Leu His Pro Asn Phe Glu Pro Ser Ala
    370                 375                 380

Leu Lys Asn Ala Lys Pro Ile Ala Lys Gly Leu Pro Ala Ser Pro Gly
385                 390                 395                 400

Ala Ala Thr Gly Lys Ile Tyr Phe Arg Ala Glu Asp Ala Val Glu Ala
                405                 410                 415

Ala Lys Asn Gly Glu Lys Asp Ile Ile Leu Val Arg Leu Glu Thr Ser
            420                 425                 430

Pro Glu Asp Ile Glu Gly Met His Val Ser Lys Gly Ile Leu Thr Gly
        435                 440                 445

Arg Gly Gly Met Thr Ser His Ala Ala Val Val Ala Arg Gly Met Gly
    450                 455                 460

Thr Cys Cys Val Ala Gly Cys Ser Glu Ile Arg Ile Asn Glu Glu Glu
465                 470                 475                 480

Lys Tyr Phe Val Asp Lys Asn Gly Lys Lys Tyr Val Glu Gly Asp Trp
                485                 490                 495

Ile Ser Leu Asp Gly Ser Thr Gly Asn Val Tyr Gly Glu Lys Leu Pro
            500                 505                 510

Thr Val Glu Pro Glu Met Thr Gly Asp Phe Ala Thr Leu Met Gln Trp
        515                 520                 525

Ala Asp Glu Ile Arg Thr Leu Lys Ile Arg Thr Asn Ala Asp Thr Pro
    530                 535                 540

Ala Asp Ala Ile Gln Ala Arg Lys Phe Gly Ala Glu Gly Ile Gly Leu
545                 550                 555                 560

Cys Arg Thr Glu His Met Phe Phe Asp Ser Asp Arg Ile Pro Ala Met
                565                 570                 575

Arg Glu Met Ile Val Ala Arg Thr Glu Glu Gln Arg Arg Lys Ala Leu
            580                 585                 590

Asp Lys Leu Leu Pro Met Gln Arg Lys Asp Phe Glu Glu Leu Phe Thr
        595                 600                 605

Ala Met Glu Gly Tyr Pro Val Thr Ile Arg Phe Leu Asp Pro Pro Leu
    610                 615                 620

His Glu Phe Leu Pro Gln Glu Asp Glu Asp Ile Glu Ala Leu Ala Lys
625                 630                 635                 640

Glu Met Gly Ile Thr Phe Asp Glu Leu Lys Ala Ile Val Thr Gly Leu
                645                 650                 655

His Glu Phe Asn Pro Met Met Gly His Arg Gly Cys Arg Leu Ala Val
            660                 665                 670

Thr Tyr Pro Glu Ile Ala Glu Met Gln Thr Arg Ala Val Ile Glu Ala
```

```
        675                 680                 685

Ala Ile Asn Val Ser Arg Lys Asn Ile Lys Val Val Pro Glu Ile Met
    690                 695                 700

Ile Pro Leu Val Gly Asp Val Lys Glu Leu Lys Tyr Val Lys Asp Val
705                 710                 715                 720

Val Val Arg Thr Ala Asn Glu Leu Ile Glu Lys Ser Gly Val Lys Ile
                725                 730                 735

Glu Tyr Lys Val Gly Thr Met Ile Glu Ile Pro Arg Ala Ala Ile Thr
            740                 745                 750

Ala Asp Glu Ile Ala Lys Glu Ala Glu Phe Phe Ser Phe Gly Thr Asn
        755                 760                 765

Asp Leu Thr Gln Met Thr Phe Gly Phe Ser Arg Asp Asp Ala Gly Lys
    770                 775                 780

Phe Leu Glu Glu Tyr Tyr Asn Lys Lys Ile Tyr Glu Phe Asp Pro Phe
785                 790                 795                 800

Ala Lys Leu Asp Gln Asp Gly Val Gly Lys Leu Val Glu Met Ala Ala
                805                 810                 815

Lys Leu Gly Arg Gln Thr Arg Pro Asp Ile Lys Leu Gly Ile Cys Gly
            820                 825                 830

Glu His Gly Gly Asp Pro Ser Ser Ile Glu Phe Cys His Gln Ile Gly
        835                 840                 845

Leu Asn Tyr Val Ser Cys Ser Pro Phe Arg Val Pro Ile Ala Arg Leu
    850                 855                 860

Ala Ala Ala Gln Ala Arg Val Asn Glu Ile Lys Gly Thr Lys Asp Leu
865                 870                 875                 880

Gly Gln Lys
```

<210> SEQ ID NO 43
<211> LENGTH: 1818
<212> TYPE: DNA
<213> ORGANISM: C.thermocellum

<400> SEQUENCE: 43

```
atgacatcaa caaacatgac aaaaaacaaa aaactgctgg attgggttaa ggaaatggct      60

gaaatgtgtc agcctgatga aatttattgg tgcgatggtt cggaggaaga aaatgagcgc     120

ttgataaagt tgatggtgga ttcaggtttg gctacgcctt tgaatcctga aaagcgacct     180

ggatgttatc tcttccgcag cgatccgtcc gacgttgccc gtgttgagga cagaactttt     240

attgcatcca aaaccaaaga agatgcagga cctacaaaca actggataga tccggttgag     300

ctcaaggcaa ctatgaaaga gttgtacaag ggttgtatga agggaagaac aatgtatgtt     360

attcctttct ccatgggacc tatcggttca cccatttcaa aaatcggcgt tgaattgacc     420

gacagccctt atgttgttgt taacatgcgc attatgactc gcataggcaa ggctgtgttg     480

gatcagctcg gagaagacgg agattttgta ccttgtctcc actcagtcgg tgctccgctc     540

aaagagggag aaaaggataa aggttggcca tgcgcaccaa tcgaaaagaa atacataagc     600

cacttcccgg aagaaaggac tatatggtca tatggttccg gatacggtgg aaatgcgctt     660

ttaggaaaga aatgctttgc acttcgtatt gcatctgtta tggcacgtga cgaaggttgg     720

cttgctgaac acatgcttat ccttcgcata acagaccctg aaggaaacaa gacatatgtt     780

acaggtgctt tcccaagcgc atgcggaaag acgaacctgg ctatgcttat tcctacaatt     840

cccggatgga aagttgaaac aatcggtgac gatattgcat ggatgagatt tggaaaagac     900

ggccgtttgt atgctatcaa ccctgaagca ggattctttg gtgttgctcc gggtacatcc     960
```

```
atggattcaa atccgaacgc aatgcataca attaagaaaa atactatatt tacaaacgtt   1020

gcattgactg atgacggcga tgtttggtgg gaaggcatcg gaactgaacc gccggctcat   1080

ctcatagact ggcagggtaa agactggact cctgattccg gaactttggc agcacatccc   1140

aacggacgtt ttacagcacc tgcaagtcag tgccctgtaa ttgctcctga atgggaggat   1200

ccggaaggtg tgccgatttc agcaatcctt atcggtggac gccgtccgaa caccattccg   1260

cttgttcatg aaagctttga ctggaaccat ggtgtattca tgggttcaat catgggttct   1320

gaaattacgg ctgccgcaat ttcaaacaaa atcggacagg tacgccgtga cccgtttgct   1380

atgctgcctt tcataggcta caacgtaaat gactatttgc agcactggtt gaacatgggt   1440

accaagactg acccaagcaa gcttcccaag atattctatg taaactggtt ccgcaaggac   1500

agcaacggta aatggttgtg gcctggatac ggtgaaaaca gccgtgttct caagtggatt   1560

gttgaaagag tcaacggaaa aggtaaagca gtaaagacac ctataggata tatgcctaca   1620

gttgacgcta tcgacacaac cggccttgat gtaagcaaag aggatatgga agaactcttg   1680

agcgttaaca aagaacagtg gctccaggaa gttgagtcaa taaaagaaca ttataagtca   1740

tacggagaaa aactgccgaa agaattgtgg gcacaattgg aggctcttga acaacgtttg   1800

aaagagtata acggttaa                                                  1818
```

<210> SEQ ID NO 44
<211> LENGTH: 605
<212> TYPE: PRT
<213> ORGANISM: C.thermocellum

<400> SEQUENCE: 44

```
Met Thr Ser Thr Asn Met Thr Lys Asn Lys Lys Leu Leu Asp Trp Val
1               5                   10                  15

Lys Glu Met Ala Glu Met Cys Gln Pro Asp Glu Ile Tyr Trp Cys Asp
            20                  25                  30

Gly Ser Glu Glu Glu Asn Glu Arg Leu Ile Lys Leu Met Val Asp Ser
        35                  40                  45

Gly Leu Ala Thr Pro Leu Asn Pro Glu Lys Arg Pro Gly Cys Tyr Leu
    50                  55                  60

Phe Arg Ser Asp Pro Ser Asp Val Ala Arg Val Glu Asp Arg Thr Phe
65                  70                  75                  80

Ile Ala Ser Lys Thr Lys Glu Asp Ala Gly Pro Thr Asn Asn Trp Ile
                85                  90                  95

Asp Pro Val Glu Leu Lys Ala Thr Met Lys Glu Leu Tyr Lys Gly Cys
            100                 105                 110

Met Lys Gly Arg Thr Met Tyr Val Ile Pro Phe Ser Met Gly Pro Ile
        115                 120                 125

Gly Ser Pro Ile Ser Lys Ile Gly Val Glu Leu Thr Asp Ser Pro Tyr
    130                 135                 140

Val Val Val Asn Met Arg Ile Met Thr Arg Ile Gly Lys Ala Val Leu
145                 150                 155                 160

Asp Gln Leu Gly Glu Asp Gly Asp Phe Val Pro Cys Leu His Ser Val
                165                 170                 175

Gly Ala Pro Leu Lys Glu Gly Glu Lys Asp Lys Gly Trp Pro Cys Ala
            180                 185                 190

Pro Ile Glu Lys Lys Tyr Ile Ser His Phe Pro Glu Glu Arg Thr Ile
        195                 200                 205

Trp Ser Tyr Gly Ser Gly Tyr Gly Gly Asn Ala Leu Leu Gly Lys Lys
```

```
    210                 215                 220

Cys Phe Ala Leu Arg Ile Ala Ser Val Met Ala Arg Asp Glu Gly Trp
225                 230                 235                 240

Leu Ala Glu His Met Leu Ile Leu Arg Ile Thr Asp Pro Glu Gly Asn
                245                 250                 255

Lys Thr Tyr Val Thr Gly Ala Phe Pro Ser Ala Cys Gly Lys Thr Asn
            260                 265                 270

Leu Ala Met Leu Ile Pro Thr Ile Pro Gly Trp Lys Val Glu Thr Ile
        275                 280                 285

Gly Asp Asp Ile Ala Trp Met Arg Phe Gly Lys Asp Gly Arg Leu Tyr
    290                 295                 300

Ala Ile Asn Pro Glu Ala Gly Phe Phe Gly Val Ala Pro Gly Thr Ser
305                 310                 315                 320

Met Asp Ser Asn Pro Asn Ala Met His Thr Ile Lys Lys Asn Thr Ile
                325                 330                 335

Phe Thr Asn Val Ala Leu Thr Asp Asp Gly Asp Val Trp Trp Glu Gly
            340                 345                 350

Ile Gly Thr Glu Pro Pro Ala His Leu Ile Asp Trp Gln Gly Lys Asp
        355                 360                 365

Trp Thr Pro Asp Ser Gly Thr Leu Ala Ala His Pro Asn Gly Arg Phe
    370                 375                 380

Thr Ala Pro Ala Ser Gln Cys Pro Val Ile Ala Pro Glu Trp Glu Asp
385                 390                 395                 400

Pro Glu Gly Val Pro Ile Ser Ala Ile Leu Ile Gly Gly Arg Arg Pro
                405                 410                 415

Asn Thr Ile Pro Leu Val His Glu Ser Phe Asp Trp Asn His Gly Val
            420                 425                 430

Phe Met Gly Ser Ile Met Gly Ser Glu Ile Thr Ala Ala Ala Ile Ser
        435                 440                 445

Asn Lys Ile Gly Gln Val Arg Arg Asp Pro Phe Ala Met Leu Pro Phe
    450                 455                 460

Ile Gly Tyr Asn Val Asn Asp Tyr Leu Gln His Trp Leu Asn Met Gly
465                 470                 475                 480

Thr Lys Thr Asp Pro Ser Lys Leu Pro Lys Ile Phe Tyr Val Asn Trp
                485                 490                 495

Phe Arg Lys Asp Ser Asn Gly Lys Trp Leu Trp Pro Gly Tyr Gly Glu
            500                 505                 510

Asn Ser Arg Val Leu Lys Trp Ile Val Glu Arg Val Asn Gly Lys Gly
        515                 520                 525

Lys Ala Val Lys Thr Pro Ile Gly Tyr Met Pro Thr Val Asp Ala Ile
    530                 535                 540

Asp Thr Thr Gly Leu Asp Val Ser Lys Glu Asp Met Glu Glu Leu Leu
545                 550                 555                 560

Ser Val Asn Lys Glu Gln Trp Leu Gln Glu Val Glu Ser Ile Lys Glu
                565                 570                 575

His Tyr Lys Ser Tyr Gly Glu Lys Leu Pro Lys Glu Leu Trp Ala Gln
            580                 585                 590

Leu Glu Ala Leu Glu Gln Arg Leu Lys Glu Tyr Asn Gly
        595                 600                 605
```

<210> SEQ ID NO 45
<211> LENGTH: 954
<212> TYPE: DNA
<213> ORGANISM: C.thermocellum

<400> SEQUENCE: 45

```
atgaacaata acaaagtaat taaaaaagta accgtagttg gtgcaggctt tgtaggttcc      60
accacagctt atacattgat gctcagcgga cttatatctg aaattgtact gatagacata     120
aatgcaaaaa aagccgacgg agaagtcatg gacttaaatc acggcatgcc ttttgtaagg     180
cccgttgaaa tttatcgtgg tgactacaaa gactgtgccg gatccgacat agtaatcatt     240
accgccggtg ccaaccaaaa agaaggcgaa acgagaatag atcttgttaa aagaaacacg     300
gaagtattca aaaatatcat aaatgaaatt gtaaagtaca acaacgattg tattcttctg     360
gtagtcacaa atccggtgga tattttaacc tatgtaactt acaaactatc cggattcccg     420
aaaaacaaag taataggttc cggaacggtt ttggacacag ccaggttccg ttatctttta     480
agcgaacatg taaaagtgga tgcacgaaat gtacatgctt atattattgg cgaacacggt     540
gacaccgaag ttgcggcctg gagtcttgca aatattgcgg gaattcccat ggatcgctac     600
tgtgacgaat gccatcagtg cgaggagcag atttcccgga ataaaaatata tgaaagtgtt    660
aaaaatgcag cttatgaaat catcaggaac aaaggtgcaa cctattatgc cgtagccctt     720
gccgtaagaa gaatcgttga agccattgta agaaatgaaa actccatcct taccgtttca     780
agccttttgg aaggacagta cggacttagc gatgtatgct taagtgttcc gacaatcgtg     840
ggtgtaaacg gtattgagga aatattgaac gtgcctttca acgatgaaga aattcagctt     900
ctcagaaagt ccggaaacac tctaaaagaa ataataaaaa cactagatat atga           954
```

<210> SEQ ID NO 46
<211> LENGTH: 317
<212> TYPE: PRT
<213> ORGANISM: C.thermocellum

<400> SEQUENCE: 46

```
Met Asn Asn Asn Lys Val Ile Lys Lys Val Thr Val Val Gly Ala Gly
1               5                   10                  15

Phe Val Gly Ser Thr Thr Ala Tyr Thr Leu Met Leu Ser Gly Leu Ile
            20                  25                  30

Ser Glu Ile Val Leu Ile Asp Ile Asn Ala Lys Lys Ala Asp Gly Glu
        35                  40                  45

Val Met Asp Leu Asn His Gly Met Pro Phe Val Arg Pro Val Glu Ile
    50                  55                  60

Tyr Arg Gly Asp Tyr Lys Asp Cys Ala Gly Ser Asp Ile Val Ile Ile
65                  70                  75                  80

Thr Ala Gly Ala Asn Gln Lys Glu Gly Glu Thr Arg Ile Asp Leu Val
                85                  90                  95

Lys Arg Asn Thr Glu Val Phe Lys Asn Ile Ile Asn Glu Ile Val Lys
            100                 105                 110

Tyr Asn Asn Asp Cys Ile Leu Leu Val Val Thr Asn Pro Val Asp Ile
        115                 120                 125

Leu Thr Tyr Val Thr Tyr Lys Leu Ser Gly Phe Pro Lys Asn Lys Val
    130                 135                 140

Ile Gly Ser Gly Thr Val Leu Asp Thr Ala Arg Phe Arg Tyr Leu Leu
145                 150                 155                 160

Ser Glu His Val Lys Val Asp Ala Arg Asn Val His Ala Tyr Ile Ile
                165                 170                 175

Gly Glu His Gly Asp Thr Glu Val Ala Ala Trp Ser Leu Ala Asn Ile
            180                 185                 190
```

```
Ala Gly Ile Pro Met Asp Arg Tyr Cys Asp Glu Cys His Gln Cys Glu
        195                 200                 205

Glu Gln Ile Ser Arg Asn Lys Ile Tyr Glu Ser Val Lys Asn Ala Ala
    210                 215                 220

Tyr Glu Ile Ile Arg Asn Lys Gly Ala Thr Tyr Tyr Ala Val Ala Leu
225                 230                 235                 240

Ala Val Arg Arg Ile Val Glu Ala Ile Val Arg Asn Glu Asn Ser Ile
                245                 250                 255

Leu Thr Val Ser Ser Leu Leu Glu Gly Gln Tyr Gly Leu Ser Asp Val
            260                 265                 270

Cys Leu Ser Val Pro Thr Ile Val Gly Val Asn Gly Ile Glu Glu Ile
        275                 280                 285

Leu Asn Val Pro Phe Asn Asp Glu Glu Ile Gln Leu Leu Arg Lys Ser
    290                 295                 300

Gly Asn Thr Leu Lys Glu Ile Ile Lys Thr Leu Asp Ile
305                 310                 315


<210> SEQ ID NO 47
<211> LENGTH: 1077
<212> TYPE: DNA
<213> ORGANISM: C.thermocellum

<400> SEQUENCE: 47

gtgataatat atagttataa gtattacaaa tacagttttt atgataacag ttttgggatt      60

atgaaaggag aagaatttat gagtttttg gaacaaataa ttgaaagggc gaaatcagac     120

gtaaaaacca tagttttgcc ggaaagtacg gatctgaggg ttattaaagc cgcatccatg     180

atagtgaaaa agggaattgc aaaggttgta ctgataggca atgaaaagga gattaagagt     240

ctggcggggg atattgatct tgaaggagtg atgatagagg attccttaaa ttccgaaaaa     300

ttggaggatt atgcaaatac actgtatgag cttagaaaat cgaagggtat gactatagaa     360

gccgcaaggg aaacgatcaa agaccctctt tattatggag ttatgatggt aaaaaaaggt     420

gaagcggatg gtatggtggc gggtgctgtc aattccactg caaatacttt gagaccggct     480

ttgcagatat taaagacggc cccggggaca aaactcgtat catccttttt tgttatggtt     540

gtacccaact gtgaatatgg tcataacgga acctttgtat atgccgattg cggcttggtg     600

gaaaatccgg atgcagacca gctttctgaa attgcaatat ctgcatccaa atcttttgag     660

atgctggttg gagcaaaacc tcaggtggca atgctttctt attcttctta cggcagtgcc     720

aaaagtgagc tgaccgaaaa ggtaatcaag gcaacacagc ttgcaaagga aaaagctccc     780

caccttgcaa ttgacggaga acttcaggtg gatgccgcca ttgttccgga agtggcaaaa     840

tcgaaggcaa agggaagcag tgttgcagga aaggccaatg ttcttatttt cccggatctt     900

gatgccggaa atattgcata caagcttaca cagagattgg caaaagctga agcttacggc     960

ccgataacac aaggtttggc aagaccggta aatgagctgt cacgaggctg cagtgccgag    1020

gatatagtcg ggttgcggc aattactgcg gttcaggctc aatatgtcaa ggcataa      1077


<210> SEQ ID NO 48
<211> LENGTH: 358
<212> TYPE: PRT
<213> ORGANISM: C.thermocellum

<400> SEQUENCE: 48

Val Ile Ile Tyr Ser Tyr Lys Tyr Tyr Lys Tyr Ser Phe Tyr Asp Asn
1               5                   10                  15
```

```
Ser Phe Gly Ile Met Lys Gly Glu Glu Phe Met Ser Phe Leu Glu Gln
            20                  25                  30

Ile Ile Glu Arg Ala Lys Ser Asp Val Lys Thr Ile Val Leu Pro Glu
        35                  40                  45

Ser Thr Asp Leu Arg Val Ile Lys Ala Ala Ser Met Ile Val Lys Lys
    50                  55                  60

Gly Ile Ala Lys Val Val Leu Ile Gly Asn Glu Lys Glu Ile Lys Ser
65                  70                  75                  80

Leu Ala Gly Asp Ile Asp Leu Glu Gly Val Met Ile Glu Asp Ser Leu
                85                  90                  95

Asn Ser Glu Lys Leu Glu Asp Tyr Ala Asn Thr Leu Tyr Glu Leu Arg
            100                 105                 110

Lys Ser Lys Gly Met Thr Ile Glu Ala Ala Arg Glu Thr Ile Lys Asp
        115                 120                 125

Pro Leu Tyr Tyr Gly Val Met Met Val Lys Lys Gly Glu Ala Asp Gly
    130                 135                 140

Met Val Ala Gly Ala Val Asn Ser Thr Ala Asn Thr Leu Arg Pro Ala
145                 150                 155                 160

Leu Gln Ile Leu Lys Thr Ala Pro Gly Thr Lys Leu Val Ser Ser Phe
                165                 170                 175

Phe Val Met Val Val Pro Asn Cys Glu Tyr Gly His Asn Gly Thr Phe
            180                 185                 190

Val Tyr Ala Asp Cys Gly Leu Val Glu Asn Pro Asp Ala Asp Gln Leu
        195                 200                 205

Ser Glu Ile Ala Ile Ser Ala Ser Lys Ser Phe Glu Met Leu Val Gly
    210                 215                 220

Ala Lys Pro Gln Val Ala Met Leu Ser Tyr Ser Ser Tyr Gly Ser Ala
225                 230                 235                 240

Lys Ser Glu Leu Thr Glu Lys Val Ile Lys Ala Thr Gln Leu Ala Lys
                245                 250                 255

Glu Lys Ala Pro His Leu Ala Ile Asp Gly Glu Leu Gln Val Asp Ala
            260                 265                 270

Ala Ile Val Pro Glu Val Ala Lys Ser Lys Ala Lys Gly Ser Ser Val
        275                 280                 285

Ala Gly Lys Ala Asn Val Leu Ile Phe Pro Asp Leu Asp Ala Gly Asn
    290                 295                 300

Ile Ala Tyr Lys Leu Thr Gln Arg Leu Ala Lys Ala Glu Ala Tyr Gly
305                 310                 315                 320

Pro Ile Thr Gln Gly Leu Ala Arg Pro Val Asn Glu Leu Ser Arg Gly
                325                 330                 335

Cys Ser Ala Glu Asp Ile Val Gly Val Ala Ala Ile Thr Ala Val Gln
            340                 345                 350

Ala Gln Tyr Val Lys Ala
        355
```

<210> SEQ ID NO 49
<211> LENGTH: 1200
<212> TYPE: DNA
<213> ORGANISM: C.thermocellum

<400> SEQUENCE: 49

```
atgaatattt tggttattaa taccggaagc tcatcactaa agtatcagct gattgacatg      60

acaaacgagt ctgtgcttgc aaaaggtgtg tgtgacagaa ttggtcttga acattccttt     120

ttaaagcata caaagaccgg aggggaaacc gtagttatag aaaaagacct gtacaatcac     180
```

```
aagcttgcca tacaggaggt aatttcggct cttacggatg aaaaaatcgg agtcataaaa    240

agcatgtcgg aaatttctgc cgtcggtcat cgtattgttc acggcggaga gaagtttaag    300

gaatctgcca taattgatga agatgtaatg aaagcaatca gggattgtgt tgaactggct    360

ccgctccaca atccgtcaaa tataatcgga attgaagcct gtaaacagat actgcccgat    420

gtgccgatgg ttgctgtgtt tgacacagct tttcatcaga caatgccaag gcatgcatat    480

atttatgccc tcccttatga gatatatgag aagtataaat tgagaaaata cggattccac    540

ggaacttccc acaaatatgt ggcccacagg gcggctcaga tgctgggcaa acctattgag    600

agcctgaagc tgataacctg ccatcttgga aacggagcga gtatttgtgc ggtaaaaggc    660

ggaaaatccg ttgacacctc aatgggattt actcctctgc aggggttgtg catgggtacc    720

agaagcggca atgttgaccc tgcggttata acttatttga tggaaaagga aaaaatgaat    780

attaacgata taaacaattt ccttaacaag aaatcaggtg tgcttggaat ttcaggtgta    840

agcagtgatt tcagagatgt tcaggatgcc gcagaaaagg gagatgacag ggcgcagctg    900

gcattggata ttttctgcta tggtgttagg aaatatattg gaaaatatat tgcagtgctg    960

aacggcgttg atgcggtggt attcactgca ggtatcggcg aaaacaatgc ttatataaga   1020

agagaagttt tgaaggatat ggactttttc ggaattaaaa tagatttgga taaaaatgaa   1080

gtgaaaggca aagaagcgga tatcagtgct cccgatgcga aagtaaagac tttggttatc   1140

ccgacaaatg aggagcttga gattgcaagg gagactttaa gacttgtaaa aaacttataa   1200


<210> SEQ ID NO 50
<211> LENGTH: 399
<212> TYPE: PRT
<213> ORGANISM: C.thermocellum

<400> SEQUENCE: 50

Met Asn Ile Leu Val Ile Asn Thr Gly Ser Ser Ser Leu Lys Tyr Gln
1               5                   10                  15

Leu Ile Asp Met Thr Asn Glu Ser Val Leu Ala Lys Gly Val Cys Asp
            20                  25                  30

Arg Ile Gly Leu Glu His Ser Phe Leu Lys His Thr Lys Thr Gly Gly
        35                  40                  45

Glu Thr Val Val Ile Glu Lys Asp Leu Tyr Asn His Lys Leu Ala Ile
    50                  55                  60

Gln Glu Val Ile Ser Ala Leu Thr Asp Glu Lys Ile Gly Val Ile Lys
65                  70                  75                  80

Ser Met Ser Glu Ile Ser Ala Val Gly His Arg Ile Val His Gly Gly
                85                  90                  95

Glu Lys Phe Lys Glu Ser Ala Ile Ile Asp Glu Asp Val Met Lys Ala
            100                 105                 110

Ile Arg Asp Cys Val Glu Leu Ala Pro Leu His Asn Pro Ser Asn Ile
        115                 120                 125

Ile Gly Ile Glu Ala Cys Lys Gln Ile Leu Pro Asp Val Pro Met Val
    130                 135                 140

Ala Val Phe Asp Thr Ala Phe His Gln Thr Met Pro Arg His Ala Tyr
145                 150                 155                 160

Ile Tyr Ala Leu Pro Tyr Glu Ile Tyr Glu Lys Tyr Lys Leu Arg Lys
                165                 170                 175

Tyr Gly Phe His Gly Thr Ser His Lys Tyr Val Ala His Arg Ala Ala
            180                 185                 190
```

```
Gln Met Leu Gly Lys Pro Ile Glu Ser Leu Lys Leu Ile Thr Cys His
        195                 200                 205

Leu Gly Asn Gly Ala Ser Ile Cys Ala Val Lys Gly Gly Lys Ser Val
    210                 215                 220

Asp Thr Ser Met Gly Phe Thr Pro Leu Gln Gly Leu Cys Met Gly Thr
225                 230                 235                 240

Arg Ser Gly Asn Val Asp Pro Ala Val Ile Thr Tyr Leu Met Glu Lys
                245                 250                 255

Glu Lys Met Asn Ile Asn Asp Ile Asn Asn Phe Leu Asn Lys Lys Ser
            260                 265                 270

Gly Val Leu Gly Ile Ser Gly Val Ser Ser Asp Phe Arg Asp Val Gln
        275                 280                 285

Asp Ala Ala Glu Lys Gly Asp Asp Arg Ala Gln Leu Ala Leu Asp Ile
    290                 295                 300

Phe Cys Tyr Gly Val Arg Lys Tyr Ile Gly Lys Tyr Ile Ala Val Leu
305                 310                 315                 320

Asn Gly Val Asp Ala Val Val Phe Thr Ala Gly Ile Gly Glu Asn Asn
                325                 330                 335

Ala Tyr Ile Arg Arg Glu Val Leu Lys Asp Met Asp Phe Phe Gly Ile
            340                 345                 350

Lys Ile Asp Leu Asp Lys Asn Glu Val Lys Gly Lys Glu Ala Asp Ile
        355                 360                 365

Ser Ala Pro Asp Ala Lys Val Lys Thr Leu Val Ile Pro Thr Asn Glu
    370                 375                 380

Glu Leu Glu Ile Ala Arg Glu Thr Leu Arg Leu Val Lys Asn Leu
385                 390                 395
```

<210> SEQ ID NO 51
<211> LENGTH: 56
<212> TYPE: DNA
<213> ORGANISM: Artificial Sequence
<220> FEATURE:
<223> OTHER INFORMATION: primer

<400> SEQUENCE: 51

```
aaaataagct atatgaaggg agaatggaga tgaacaatag acaacccctt tctgtg         56
```

<210> SEQ ID NO 52
<211> LENGTH: 6259
<212> TYPE: DNA
<213> ORGANISM: Artificial Sequence
<220> FEATURE:
<223> OTHER INFORMATION: pAMG206::Pcbp-Mj_mdh

<400> SEQUENCE: 52

```
gagtcgtgac taagaacgtc aaagtaatta acaatacagc tatttttctc atgcttttac     60

ccctttcata aaatttaatt ttatcgttat cataaaaaat tatagacgtt atattgcttg    120

ccgggatata gtgctgggca ttcgttggtg caaaatgttc ggagtaaggt ggatattgat    180

ttgcatgttg atctattgca ttgaaatgat tagttatccg taaatattaa ttaatcatat    240

cataaattaa ttatatcata attgttttga cgaatgaagg tttttggata aattatcaag    300

taaaggaacg ctaaaaattt tggcgtaaaa tatcaaaatg accacttgaa ttaatatggt    360

aaagtagata taatattttg gtaaacatgc cttcagcaag gttagattag ctgtttccgt    420

ataaattaac cgtatggtaa aacggcagtc agaaaaataa gtcataagat tccgttatga    480

aaatatactt cggtagttaa taataagaga tatgaggtaa gagatacaag ataagagata    540
```

```
taaggtacga atgtataaga tggtgctttt aggcacacta aataaaaaac aaataaacga    600
aaattttaag gaggacgaaa gatgaaagtt acaattatag gagcttctgg tagagttggg    660
agtgcaacag ccttattatt agctaaagaa ccttttatga aggatttggt gttaattgga    720
agagaacatt caataaataa attggaagga ttgagagaag acatctacga tgccttagct    780
gggacaagaa gtgatgcaaa tatatacgtt gagagtgatg aaaatctaag gataattgat    840
gaaagtgatg ttgttataat aacaagcggt gttccaagaa aagagggaat gagtaggatg    900
gatttggcaa aaacaaatgc aaaaattgtt gggaagtatg ctaaaaaaat agctgaaatc    960
tgcgatacaa aaatatttgt tataacaaac cctgtggatg tgatgactta taaagctctg   1020
gtagattcaa aatttgaaag aaatcaagtt tttggattag ggactcattt agattctttg   1080
aggtttaagg ttgctattgc taagtttttc ggtgttcata ttgatgaagt taggacgaga   1140
attattggag agcatgggga cagcatggtt ccattgttaa gtgctacctc tatcggagga   1200
attcctattc aaaaatttga aagatttaag gaactgccaa tagatgagat tatagaggat   1260
gttaaaacaa aaggagagca gattattaga ttgaaaggag gttctgagtt tggtccagca   1320
gcagccattt taaatgttgt taggtgtatt gtgaataatg agaaaagatt gctaacttta   1380
tccgcttacg tagatggaga gtttgatgga attagagatg tgtgtattgg agttccagta   1440
aagattggaa gagatgggat agaagaggtt gtatcaattg aattggataa agatgagata   1500
attgcattta gaaaatctgc tgaaatcatt aaaaaatact gtgaagaagt taaaaactta   1560
taaaccaaaa tcccttaacg tgagttttcg ttccactgag cgtcagaccc cgtagaaaag   1620
atcaaaggat cttcttgaga tccttttttt ctgcgcgtaa tctgctgctt gcaaacaaaa   1680
aaaccaccgc taccagcggt ggtttgtttg ccggatcaag agctaccaac tctttttccg   1740
aaggtaactg gcttcagcag agcgcagata ccaaatactg tccttctagt gtagccgtag   1800
ttaggccacc acttcaagaa ctctgtagca ccgcctacat acctcgctct gctaatcctg   1860
ttaccagtgg ctgctgccag tggcgataag tcgtgtctta ccgggttgga ctcaagacga   1920
tagttaccgg ataaggcgca gcggtcgggc tgaacggggg gttcgtgcac acagcccagc   1980
ttggagcgaa cgacctacac cgaactgaga tacctacagc gtgagctatg agaaagcgcc   2040
acgcttcccg aagggagaaa ggcggacagg tatccggtaa gcggcagggt cggaacagga   2100
gagcgcacga gggagcttcc agggggaaac gcctggtatc tttatagtcc tgtcgggttt   2160
cgccacctct gacttgagcg tcgatttttg tgatgctcgt caggggggcg gagcctatgg   2220
aaaaacgcca gcaacgcggc ctttttacgg ttcctgggct tttgctggcc ttttgctcac   2280
atgttctttc ctgcgttatc ccctgattct gtggataacc gtattaccgc ctttgagtga   2340
gctgataccg ctcgccgcag ccgaacgacc gagcgcagcg agtcagtgag cgaggaagcg   2400
gaagagcgcc caatacgcaa accgcctctc cccgcgcgtt ggccgattca ttaatgcagg   2460
gccgcagctt gcaaattaaa gccttcgagc gtcccaaaac cttctcaagc aaggttttca   2520
gtataatgtt acatgcgtac acgcgtctgt acagaaaaaa aagaaaaatt tgaaatataa   2580
ataacgttct taatactaac ataactataa aaaaataaat agggacctag acttcaggtt   2640
gtctaactcc ttccttttcg gttagagcgg atgtgggggg agggcgtgaa tgtaagcgtg   2700
acataactaa ttacatgatg cggccctcta ggatcagcgg gtttaaacgc tgaggcgcgc   2760
cgaattcggt accaaaacaa aaggcccagt cttccgactg agccttttgt tttctcgagg   2820
cccgggctta gctgtacatt tcaggtttca aaacgcctat aaaaggaagg ttcctgtact   2880
tttcatcaaa gtccaatcca taacccacga caaacttatc aggtatctta aatcctacat   2940
```

```
aatcgacttt tacagatgct tctcttctct ccggtttgtc taatattgtg catattttca   3000

ggctttttgg cttccttcca agtaaagttt cccttaagta agacaaagtc aaaccgctgt   3060

caattatgtc ttccacaatc agaacatctt tgccttctat gcttatatca agatctttga   3120

ttatctttac tattcctgat gaatgagttg agcttccata gctggaaaca gccataaaat   3180

caagtgataa aggcaaatct atgtgtcttg acaaatcagc cataaacatt aaagcacctt   3240

ttaaaactcc taccaacatc aaatttttcc ctttgtagtc ttttgtgatt tgcctcccaa   3300

gctcttttat cttttcctta agttcttctt ctgtgatcaa aatttcatcg atgtcttttg   3360

ataaatttc catgacgtcg acctccttta ttataaaagc cagtcattag gcctatctga    3420

caattcctga atagagttca taaacaatcc tgcatgataa ccatcacaaa cagaatgatg   3480

tacctgtaaa gatagcggta aatatattga attaccttta ttaatgaatt ttcctgctgt   3540

aataatgggt agaaggtaat tactattatt attgatattt aagttaaacc cagtaaatga   3600

agtccatgga ataatagaaa gagaaaaagc attttcaggt ataggtgttt tgggaaacaa   3660

tttccccgaa ccattatatt tctctacatc agaaaggtat aaatcataaa actctttgaa   3720

gtcattcttt acaggagtcc aaataccaga gaatgtttta gatacaccat caaaaattgt   3780

ataaagtggc tctaacttat cccaataacc taactctccg tcgctattgt aaccagttct   3840

aaaagctgta tttgagttta tcacccttgt cactaagaaa ataaatgcag ggtaaaattt   3900

atatccttct tgttttatgt ttcggtataa aacactaata tcaatttctg tggttatact   3960

aaaagtcgtt tgttggttca aataatgatt aaatatctct tttctcttcc aattgtctaa   4020

atcaatttta ttaaagttca ttaatatcgc ctcctattgt aaattaaaat ttaatttaat   4080

gcctctatta gctgccataa agcatgaatg cagtaaaata ttcatcctct ggcaagtatc   4140

tcttgcacta tgattcattt tatattattt tattttcatt ttcaatagtt tagataaaaa   4200

ataattaatt ttttaacaaa gtatttttat cttcctttga tgtaattctt tgtttttttg   4260

tccattaata ttatggacaa tttttttatt tctagtcaat aattttaatc tttattaaaa   4320

cctggcaatg ccagagagat acagtaatta ttgcatataa aagaaaacag acgcgccctg   4380

tttgtttcct gaaaaaccac ctcgtcctcc aaagtatcca gctttttaaa atccatcctc   4440

attcccagac gaaaaagttt tgacaaagcc tcttttcttg tccatagaat tgtactctgc   4500

acacaatatt catcagtatt tccaaaactc tttagaatct tttcctctct ttcggaaaag   4560

aaatacttta tcaatgcatc ctcgggcaaa aaaatctttt ccatgtctat tcccaccgcc   4620

ctgtccgaaa ccattccgat acaatacgga aacgcatggg ttattgatac acccatgtca   4680

gaatactggc cggcctcgcg aggatccaag cttactagct atgggaaaca aaatattgcg   4740

tatgcgactg ttcacatgga cgagaaaacc cctcacatgc atttaggagt tgttcctatg   4800

cgcctagagg gcttttcgtg cgtcagcatg agcgatcgga agaaaagaag aatacttttt   4860

cgcttcaaga tgttttgcag cgtgatcgag aacttcgtga gcaaagaaaa gcaaagagga   4920

aaaaatcgca tgatttggag cgataagaaa aagcactcga atgagtgctt tttttgcgtt   4980

ttgagcgtag cgaaaaacga gttctttcta ttcttgatac atatagaaat aacgtcattt   5040

ttattttagt tgctgaaagg tgcgttgaag tgttggtatg tatgtgtttt aaagtattga   5100

aaacccttaa aattggttgc acagaaaaac cccatctgtt aaagttataa gtgaccaaac   5160

aaataactaa atagatgggg gtttctttta atattatgtg tcctaatagt agcatttatt   5220

cagatgaaaa atcaagggtt ttagtggaca agacaaaaag tggaaaagtg agaccatgga   5280
```

```
gagaaaagaa aatcgctaat gttgattact ttgaacttct gcatattctt gaatttaaaa   5340

aggctgaaag agtaaaagat tgtgctgaaa tattagagta taaacaaaat cgtgaaacag   5400

gcgaaagaaa gttgtatcga gtgtggtttt gtaaatccag gctttgtcca atgtgcaact   5460

ggaggagagc aatgaaacat ggcattcagt cacaaaaggt tgttgctgaa gttattaaac   5520

aaaagccaac agttcgttgg ttgtttctca cattaacagt taaaaatgtt tatgatggcg   5580

aagaattaaa taagagtttg tcagatatgg ctcaaggatt tcgccgaatg atgcaatata   5640

aaaaaattaa taaaaatctt gttggtttta tgcgtgcaac ggaagtgaca ataaataata   5700

aagataattc ttataatcag cacatgcatg tattggtatg tgtggaacca acttatttta   5760

agaatacaga aaactacgtg aatcaaaaac aatggattca attttggaaa aaggcaatga   5820

aattagacta tgatccaaat gtaaaagttc aaatgattcg accgaaaaat aaatataaat   5880

cggatataca atcggcaatt gacgaaactg caaaatatcc tgtaaaggat acggatttta   5940

tgaccgatga tgaagaaaag aatttgaaac gtttgtctga tttggaggaa ggtttacacc   6000

gtaaaaggtt aatctcctat ggtggtttgt taaaagaaat acataaaaaa ttaaaccttg   6060

atgacacaga agaaggcgat ttgattcata cagatgatga cgaaaaagcc gatgaagatg   6120

gattttctat tattgcaatg tggaattggg aacggaaaaa ttattttatt aaagagtagt   6180

tcaacaaacg ggattgactt ttaaaaaagg attgattcta atgaagaaag cagacaagta   6240

agcctcctaa attcactag                                                6259
```

<210> SEQ ID NO 53
<211> LENGTH: 67
<212> TYPE: DNA
<213> ORGANISM: Artificial Sequence
<220> FEATURE:
<223> OTHER INFORMATION: primer

<400> SEQUENCE: 53

```
acaagaaacc tttgtatatt ttttagtcca tatcttctca gaattctttc tcctccttct     60

tttatcc                                                               67
```

<210> SEQ ID NO 54
<211> LENGTH: 72
<212> TYPE: DNA
<213> ORGANISM: Artificial Sequence
<220> FEATURE:
<223> OTHER INFORMATION: primer

<400> SEQUENCE: 54

```
aaaaaccggc atattggtgt taagtgaaag acgacggcag ggaaatatta aaatggaaat     60

gttgaaaaaa tg                                                         72
```

<210> SEQ ID NO 55
<211> LENGTH: 55
<212> TYPE: DNA
<213> ORGANISM: Artificial Sequence
<220> FEATURE:
<223> OTHER INFORMATION: primer

<400> SEQUENCE: 55

```
caagatcaca gaaaggggtt gtctattgtt catctccatt ctcccttcat atagc          55
```

<210> SEQ ID NO 56
<211> LENGTH: 29
<212> TYPE: DNA
<213> ORGANISM: Artificial Sequence
<220> FEATURE:
<223> OTHER INFORMATION: primer

<400> SEQUENCE: 56
gagcgatgac aagggagtaa ttttagatc 29

<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57
ttcgactatt tcccttagct cctctttctc 30

<210> SEQ ID NO 58
<211> LENGTH: 45
<212> TYPE: DNA
<213> ORGANISM: Artificial Sequence
<220> FEATURE:
<223> OTHER INFORMATION: primer

<400> SEQUENCE: 58
tttaaggagg acgaaagatg aaagttacaa ttataggagc ttctg 45

<210> SEQ ID NO 59
<211> LENGTH: 45
<212> TYPE: DNA
<213> ORGANISM: Artificial Sequence
<220> FEATURE:
<223> OTHER INFORMATION: primer

<400> SEQUENCE: 59
ttaagggatt ttggtttata agtttttaac ttcttcacag tattt 45

<210> SEQ ID NO 60
<211> LENGTH: 24
<212> TYPE: DNA
<213> ORGANISM: Artificial Sequence
<220> FEATURE:
<223> OTHER INFORMATION: primer

<400> SEQUENCE: 60
ctttcgtcct ccttaaaatt ttcg 24

<210> SEQ ID NO 61
<211> LENGTH: 44
<212> TYPE: DNA
<213> ORGANISM: Artificial Sequence
<220> FEATURE:
<223> OTHER INFORMATION: primer

<400> SEQUENCE: 61
aagcctccta aattcactag gagtcgtgac taagaacgtc aaag 44

ENGINEERING AN INCREASE IN ETHANOL PRODUCTION BY ALTERING COFACTOR SPECIFICITY

CROSS-REFERENCE TO RELATED APPLICATIONS

This application is the National Stage of International Application Number PCT/US2012/067216, filed Nov. 30, 2012, which claims the benefit of U.S. Provisional Application No. 61/565,261, filed Nov. 30, 2011, which are incorporated by reference herein.

STATEMENT REGARDING FEDERALLY-SPONSORED RESEARCH AND DEVELOPMENT

This invention was funded, in part, by the United States government under a Department of Energy Biomass Program award # DE-FC36-07G017057. This invention was also funded, in part, by the BioEnergy Science Center (BESC) under the DOE Office of Science through award number DE-POS2-06ER64304. The U.S. Government has certain rights in this invention.

REFERENCE TO A SEQUENCE LISTING SUBMITTED ELECTRONICALLY VIA EFS-WEB

The content of the electronically submitted sequence listing (Name: 2608_0650001SEQIDListing_ascii.txt; Size: 201,728 bytes; and Date of Creation: May 23, 2014) is herein incorporated by reference in its entirety.

BACKGROUND OF THE INVENTION

The ability to provide for the fuel and energy needs of the world's growing population has emerged as one of the great challenges of this century. Current fuel and energy needs are primarily met by non-renewable fossil fuels, a source that is both unsustainable and increasingly cost-inefficient. Therefore, new approaches to solving the world's energy needs are required to address these mounting concerns.

Among forms of plant biomass, lignocellulosic biomass is particularly well-suited for energy applications because of its large-scale availability, low cost, and environmentally benign production. In particular, many energy production and utilization cycles based on cellulosic biomass have very low greenhouse gas emissions on a life-cycle basis. The primary obstacle impeding the more widespread production of energy from biomass feedstocks is the general absence of low-cost technology for overcoming the recalcitrance of biomass feedstocks to conversion into useful products. Lignocellulosic biomass contains carbohydrate fractions (e.g., cellulose and hemicellulose) that can be converted into ethanol or other end-products including lactic acid and acetic acid. In order to convert the carbohydrate fractions, the cellulose or hemicellulose must ultimately be converted, or hydrolyzed, into monosaccharides. The hydrolysis of cellulose and hemicellulose has historically proven to be problematic.

Cellulose digesting anaerobic bacteria are of great potential utility because they can be used to produce ethanol or other fuels from abundant substrates such as forestry, municipal and agricultural waste. However, it has been challenging to realize the potential utility of biomass because of difficulty in the genetic manipulation of anaerobic bacteria and a lack of understanding of their metabolic biochemistry. Genome sequence data and recent advances in biotechnological tools for genetic modification of *Clostridium thermocellum* and other similar organisms have made it possible to make progress in the utilization of biomass for fuel, but the great complexity of metabolism makes it difficult to achieve a desired outcome such as near theoretical ethanol yield from cellulosic substrates.

Many microorganisms can metabolize glucose, cellulose or cellodextrins anaerobically, but they vary in the pathways utilized and the products generated. It has been demonstrated in genetically modified *Thermoanaerobacterium saccharolyticum* that glucose and cellobiose can be fermented to ethanol at very close to theoretical yield, but similar genetic manipulations in *Clostridium thermocellum* have not had the same outcome. Argyros et al. "High ethanol titers from cellulose using metabolically engineered thermophilic, anaerobic microbes." *Appl. Env. Microbiol.,* 2011 doi:10.1128/AEM.00646-11 (epub ahead of publication).

*Clostridium thermocellum* has both cellulolytic and ethanologenic fermentation capabilities and can directly convert a cellulose-based substrate into ethanol. However, *C. thermocellum* possesses a branched carbon utilization pathway that generates undesirable products, and thus its yield of ethanol is low. Furthermore, *C. thermocellum* is not as amenable to manipulation for ethanol production as *T. saccharolyticum*. The difficulty in manipulating *C. thermocellum* for ethanol production is exemplified more clearly when the carbon utilization pathways from *C. thermocellum* and *T. saccharolyticum* are compared. In homoethanologenic *T. saccharolyticum*, the carbon atoms from glucose flow down a linear central metabolic pathway to ethanol (FIG. 1A). In *C. thermocellum*, a different set of enzymes is present and thus the carbon utilization pathway (FIG. 1B) is different that the carbon utilization pathway in *T. saccharolyticum*. The difference in the carbon-utilization pathways of *C. thermocellum* compared to *T. saccharolyticum* makes it infeasible to produce ethanol at theoretical yield with the same modifications.

Many enzymes in carbon-utilizing metabolic processes use a nicotinamide adenine dinucleotide as a cofactor. There are two common types of nicotinamide adenine dinucleotide cofactors, $NAD^+$ and $NADP^+$. Each can exist in a reduced or oxidized form. In order to maintain steady state, each cofactor involved in a reaction must be regenerated at the same rate it is consumed. In other words, the cell must be reduction-oxidation ("redox") balanced. Enzymes are typically specific for (i.e. react with) either the phosphorylated ($NADP^+$, NADPH) or non-phosphorylated ($NAD^+$, NADH) nicotinamide cofactors. The specificity of an enzyme can sometimes be switched from one nicotinamide cofactor to the other by mutations in the cofactor binding region of the protein. It is also possible to find different isoforms of an enzyme that carry out the same enzymatic activity, but use different cofactors (e.g. $NAD^+$ instead of $NADP^+$). Isoforms with altered cofactor specificity may be found for example in different species.

The *T. saccharolyticum* oxidation-reduction reactions in the metabolic pathway from cellobiose to ethanol are:

(1) D-glyceraldehyde 3-phosphate+phosphate+$NAD^+$=3-phospho-D-glyceroyl phosphate+NADH+$H^+$ (catalyzed by glyceraldehyde-3-phosphate dehydrogenase)

(2) pyruvate+CoA+oxidized ferredoxin=acetyl-CoA+$CO_2$+reduced ferredoxin+$H^+$ (catalyzed by pyruvate oxidoreductase)

(3) reduced ferredoxin+NADH+2 $NADP^+$+$H^+$=oxidized ferredoxin+$NAD^+$+2 NADPH (catalyzed by NADH-dependent reduced ferredoxin:NADP+oxidoreductase)

(4) acetyl-CoA+NADPH+$H^+$=acetaldehyde+CoA+$NADP^+$ (catalyzed by acetaldehyde dehydrogenase)

(5) acetaldehyde+NADPH+$H^+$=ethanol+$NADP^+$ (catalyzed by alcohol dehydrogenase)

Reactions 1-5 above are redox and cofactor balanced. A single polypeptide called AdhE contains both catalytic activities of steps 4 and 5. Activity of AdhE is detectable with both NADH and NADPH cofactors (See Shaw et al., "Metabolic engineering of a thermophilic bacterium to produce ethanol at high yield." *PNAS* 2008. 105(37): 13769-74). In *C. thermocellum*, activity can be detected for both cofactors in the alcohol dehydrogenase reaction, but the aldehyde dehydrogenase reaction is specific to NADH only (See Brown et al., "Mutant alcohol dehydrogenase leads to improved ethanol tolerance in *Clostridium thermocellum." PNAS* 2011. 108(33): 13753-7 and Rydzak et al., "Growth phase-dependent enzyme profile of pyruvate catabolism and end-product formation in *Clostridium thermocellum* ATCC 27405.*" J. of Biotech.* 2009. 104(3-4): 169-75). Therefore, reaction 4 above cannot occur in *C. thermocellum*. Reaction 4 can occur with NADH as the cofactor, but use of NADH would lead to an overabundance of NADPH and depletion of NADH in the cell. The oxidation-reduction reactions in *C. thermocellum* in the pathway from cellobiose to ethanol are the same as 1-5 above, but with the addition of two more:

(6) oxaloacetate+NADH+$H^+$=malate+$NAD^+$ (catalyzed by malate dehydrogenase)

(7) malate+$NADP^+$=pyruvate+$CO_2$+NADPH (catalyzed by malic enzyme)

The net effect of these two additional reactions in *C. thermocellum* is that electrons are transferred from NADH to NADPH. This leads to a further accumulation of NADPH and makes the pathway from cellobiose to ethanol unbalanced for cofactors and therefore infeasible in this configuration. As a result, *C. thermocellum* strains lacking the ability to make other end products (e.g. mutants for lactate dehydrogenase and phosphotransacetylase) show poor ethanol productivity and secrete amino acids that consume NADPH during their biosynthesis.

Consequently, in order to optimize ethanol production in *C. thermocellum*, there is a need for mutant strains of *C. thermocellum* that are reduction-oxidation and cofactor balanced.

The present invention relates to cellulose-digesting organisms that have been genetically modified to allow the production of ethanol at high yield by changing cofactor usage and/or production at key steps of central metabolism.

BRIEF SUMMARY OF THE INVENTION

In one embodiment, the invention relates to a recombinant microorganism capable of fermenting biomass and producing ethanol. In some embodiments, the microorganism is a prokaryote.

In some embodiments, the invention relates to a recombinant microorganism that expresses at least one enzyme with an altered cofactor specificity in the metabolic pathway from cellobiose to ethanol.

In one embodiment, the invention relates to a recombinant prokaryotic microorganism comprising a heterologous nucleic acid encoding alcohol dehydrogenase with an altered cofactor specificity relative to the endogenous enzyme wherein the polynucleotide is at least about 95% identical to SEQ ID NO: 3, or encodes a polypeptide at least about 95% identical to the polypeptide sequence of SEQ ID NOs: 2, 7, 9, 11, 13, 15, 17, 19, or 21.

In one embodiment, the invention relates to a recombinant prokaryotic microorganism comprising a heterologous nucleic acid encoding alcohol dehydrogenase with an altered cofactor specificity relative to the endogenous enzyme wherein the polynucleotide is at least about 95% identical to SEQ ID NO: 3, or encodes a polypeptide at least about 95% identical to the polypeptide sequence of SEQ ID NOs: 2, 7, 9, 11, 13, 15, 17, 19, or 21, and a genetic modification that leads to the down-regulation of an enzyme in a pyruvate metabolism pathway wherein the polynucleotide encoding for the down-regulated enzyme encodes a polypeptide sequence at least about 95% identical to the polypeptide sequence of SEQ ID NOs: 38, 40, 42, 44, 46, 48 or 50.

In one embodiment, the invention relates to a recombinant prokaryotic microorganism comprising a heterologous nucleic acid encoding acetaldehyde dehydrogenase with an altered cofactor specificity relative to the endogenous enzyme, wherein the polynucleotide encodes a polypeptide sequence at least about 95% identical to the polypeptide sequence of SEQ ID NOs: 5, 7, 9, 11, 13, 15, 17, 19, or 21.

In one embodiment, the invention relates to a recombinant prokaryotic microorganism comprising a heterologous nucleic acid encoding acetaldehyde dehydrogenase with an altered cofactor specificity relative to the endogenous enzyme, wherein the polynucleotide encodes a polypeptide sequence at least about 95% identical to the polypeptide sequence of SEQ ID NOs: 5, 7, 9, 11, 13, 15, 17, 19, or 21, and a genetic modification that leads to the down-regulation of an enzyme in a pyruvate metabolism pathway wherein the polynucleotide encoding for the down-regulated enzyme has a nucleotide sequence at least about 95% identical to the polypeptide sequence of SEQ ID NOs: 38, 40, 42, 44, 46, 48 or 50.

In one embodiment, the invention relates to a recombinant prokaryotic microorganism comprising a heterologous nucleic acid encoding malate dehydrogenase with an altered cofactor specificity relative to the endogenous enzyme, wherein the polynucleotide encodes a polypeptide sequence at least about 95% identical to the polypeptide sequence of SEQ ID NOs: 23 or 25.

In one embodiment, the invention relates to a recombinant prokaryotic microorganism comprising a heterologous nucleic acid encoding malate dehydrogenase with an altered cofactor specificity relative to the endogenous enzyme, wherein the polynucleotide encodes a polypeptide sequence at least about 95% identical to the polypeptide sequence of SEQ ID NOs: 23 or 25, and a genetic modification that leads to the down-regulation of an enzyme in a pyruvate metabolism pathway wherein the polynucleotide encoding for the down-regulated enzyme encodes a polypeptide sequence at least about 95% identical to the polypeptide sequence of SEQ ID NOs: 38, 40, 42, 44, 46, 48 or 50.

In one embodiment, the invention relates to a recombinant prokaryotic microorganism comprising a heterologous nucleic acid encoding formate dehydrogenase with an altered cofactor specificity relative to the endogenous enzyme, if any, wherein the polynucleotide encodes a polypeptide sequence at least about 95% identical to the polypeptide sequence of SEQ ID NO: 27, 29, or 31.

In one embodiment, the invention relates to a recombinant prokaryotic microorganism comprising a heterologous nucleic acid encoding formate dehydrogenase with an altered cofactor specificity relative to the endogenous enzyme, if any, wherein the polynucleotide encodes a polypeptide sequence at least about 95% identical to the polypeptide sequence of SEQ ID NO: 27, 29, or 31, and a genetic modification that leads to the down-regulation of an enzyme in a pyruvate metabolism pathway wherein the polynucleotide encoding for the down-regulated enzyme encodes a polypeptide sequence at least about 95% identical to the polypeptide sequence of SEQ ID NOs: 38, 40, 42, 44, 46, 48 or 50.

In one embodiment, the invention relates to a recombinant prokaryotic microorganism comprising a heterologous nucleic acid encoding malic enzyme with an altered cofactor specificity relative to the endogenous enzyme, wherein the polynucleotide has a nucleotide sequence at least about 95% identical to SEQ ID NO: 34, or encodes a polypeptide at least about 95% identical to the polypeptide sequence of SEQ ID NO: 33.

In one embodiment, the invention relates to a recombinant prokaryotic microorganism comprising a heterologous nucleic acid encoding malic enzyme with an altered cofactor specificity relative to the endogenous enzyme, wherein the polynucleotide has a nucleotide sequence at least about 95% identical to SEQ ID NO: 34, or encodes a polypeptide at least about 95% identical to the polypeptide sequence of SEQ ID NO: 33, and a genetic modification that leads to the down-regulation of an enzyme in a pyruvate metabolism pathway wherein the polynucleotide encoding for the down-regulated enzyme encodes a polypeptide sequence at least about 95% identical to the polypeptide sequence of SEQ ID NOs: 38, 40, 42, 44, 46, 48 or 50.

In one embodiment, the invention relates to a recombinant prokaryotic microorganism comprising a heterologous nucleic acid encoding glyceraldehyde-3-phosphate dehydrogenase with an altered cofactor specificity relative to the endogenous enzyme, wherein the polynucleotide encodes a polypeptide sequence at least about 95% identical to the polypeptide sequence of SEQ ID NO: 36.

In one embodiment, the invention relates to a recombinant prokaryotic microorganism comprising a heterologous nucleic acid encoding glyceraldehyde-3-phosphate dehydrogenase with an altered cofactor specificity relative to the endogenous enzyme, wherein the polynucleotide encodes a polypeptide sequence at least about 95% identical to the polypeptide sequence of SEQ ID NO: 36, and a genetic modification that leads to the down-regulation of an enzyme in a pyruvate metabolism pathway wherein the polynucleotide encoding for the down-regulated enzyme encodes a polypeptide sequence at least about 95% identical to the polypeptide sequence of SEQ ID NOs: 38, 40, 42, 44, 46, 48 or 50.

In some embodiments, the cells of the invention comprise multiple combinations of up-regulated enzymes with altered cofactor specificities relative to the endogenous enzyme and genetic modifications that lead to the down-regulation of enzymes in a pyruvate metabolism pathway.

BRIEF DESCRIPTION OF THE DRAWINGS/FIGURES

FIG. 1 depicts a simplified metabolic pathway from cellobiose to ethanol in *T. saccharolyticum* (A) and *C. thermocellum* (B). Only reduced nicotinamide cofactors are shown; the oxidized forms are implied. The cofactors involved in acetate and lactate production are not shown. The multiple steps from cellobiose to phosphoenolpyruvate are represented by a dotted line, but all other arrows represent single biochemical reactions. Abbreviations are PEP=phosphoenolpyruvate, Pyr=pyruvate, Oxa=oxaloacetate. Mal=malate, Ac-CoA=acetyl-CoA, Aceald=acetaldehyde, EtOH=ethanol, Ac-P=acetyl phosphate, Fdred=reduced ferredoxin, Fdox=oxidized ferredoxin. The names of the genes encoding the enzymes that catalyze each step are shown in italics.

FIG. 2 depicts the successful integration of the adhB gene from *T. ethanolicus* into the hpt locus of *C. thermocellum* without extraneous plasmid sequences or antibiotic resistance genes. FIG. 2 shows a gel image of PCR products from different isolates. Colonies from agar plates were subjected to PCR using primers flanking hpt and external to the homology regions in the integrating construct. DNA size standards are present on both sides of the gel. Lane 1: colony #1 from AZH selection plate, Lane 2: colony #2 from AZH selection plate, Lane 3: colony #3 from AZH selection plate, Lane 4: cells from culture before AZH selection, Lane 5: DNA from WT *C. thermocellum* strain DSM1313. The gel shows bands larger than those of WT in lanes 1-3 which indicated the presence of inserted DNA, but smaller than the band in Lane 5, which indicates the presence of a complete integrated plasmid.

FIG. 3 depicts growth curves from 18 different cultures in a 96-well microtiter plate over 24 hours. In each box, optical density is plotted on the Y axis and time is plotted on the X axis. Three different strains of *C. thermocellum* were tested in media containing added ethanol at the concentrations indicated. The strains were WT, an ethanol adapted strain called adhE* described in Brown et al. "Mutant alcohol dehydrogenase leads to improved ethanol tolerance in *Clostridium thermocellum." PNAS* 2011. 108(33):13752-7, and a strain with the adhB gene from *T. ethanolicus* inserted into the hpt locus described below. The results show that the adhE* and adhB strains grow at a higher concentration of ethanol than the WT.

DETAILED DESCRIPTION OF THE INVENTION

Definitions

Figure 1:
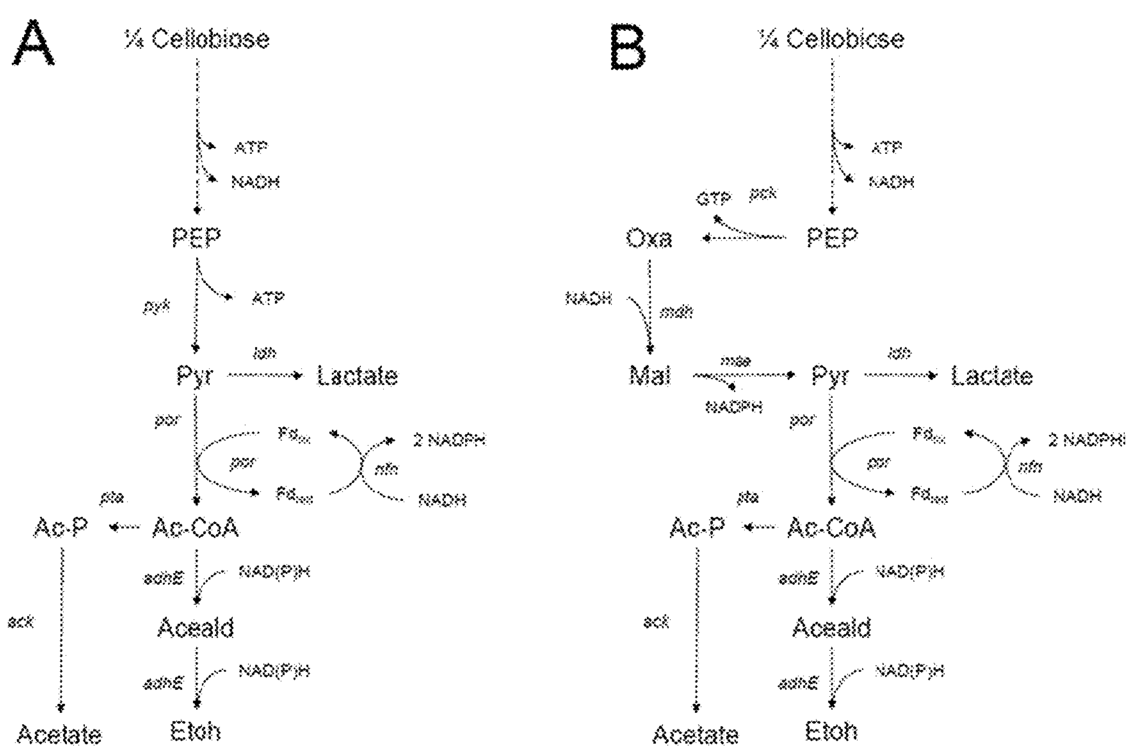

Unless defined otherwise, all technical and scientific terms used herein have the same meaning as commonly understood to one of ordinary skill in the art of microbial metabolic engineering. Although methods and materials similar or equivalent to those described herein can be used in the practice of the disclosed methods and compositions, exemplary methods, devices and materials are described herein.

The embodiment(s) described, and references in the specification to "one embodiment", "an embodiment", "an example embodiment", etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein may refer to a single item or multiple items. It is understood that wherever embodiments are described herein with the language "comprising," otherwise analogous embodiments described in terms of "consisting of" and/or "consisting essentially of" are also provided. Thus, for example, reference to "a polynucleotide" includes a plurality of such polynucleotides and reference to "the microorganism" includes reference to one or more microorganisms, and so forth.

The term "heterologous" is used in reference to a polynucleotide or a gene not normally found in the host organism. "Heterologous" includes up-regulated or down-regulated endogenous genes. "Heterologous" also includes a native coding region, or portion thereof, that is reintroduced into the source organism in a form that is different from the corresponding native gene, e.g. not in its natural location in the organism's genome. "Heterologous" also includes any gene that has been modified and placed into an organism. A heterologous gene may include a native coding region that is a portion of a chimeric gene including a non-native regulatory region that is reintroduced into the native host or modifications to the native regulatory sequences that affect the expression level of the gene. Foreign genes can comprise native genes inserted into a non-native organism, or chimeric genes. A heterologous polynucleotide, gene, polypeptide, or an enzyme may be derived from any source, e.g., eukaryotes, prokaryotes, viruses, or synthetic polynucleotide fragments, and includes up-regulated endogenous genes.

The terms "gene(s)" or "polynucleotide" or "nucleic acid" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. Also, the terms are intended to include a specific gene for a selected purpose. The gene may be endogenous to the host cell or may be recombinantly introduced into the host cell, e.g. as a plasmid maintained episomally or a plasmid (or fragment thereof) that is stably integrated into the genome. In addition to the plasmid form, a gene may, for example, be in the form of linear DNA or RNA. The term "gene" is also intended to cover multiple copies of a particular gene, e.g., all of the DNA sequences in a cell encoding a particular gene product.

The term "expression" is intended to include the expression of a gene at least at the level of mRNA production, generally subsequently translated into a protein product.

As used herein, an "expression vector" is a vector capable of directing the expression of genes to which it is operably linked.

In some embodiments, the microorganisms contain enzymes involved in cellulose digestion, metabolism and/or hydrolysis. A "cellulolytic enzyme" can be any enzyme involved in cellulose digestion, metabolism, and/or hydrolysis. The term "cellulase" refers to a class of enzymes produced chiefly by fungi, bacteria, and protozoans that catalyze cellulolysis (i.e. the hydrolysis) of cellulose. However, there are also cellulases produced by other types of organisms such as plants and animals. Several different kinds of cellulases are known, which differ structurally and mechanistically. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviate CBH)— one type working processively from the reducing end, and one type working processively from the non-reducing end of cellulose; cellobiase or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulose digestion, metabolism and/or hydrolysis, including, for example, an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase protein.

A "plasmid" or "vector" refers to an extrachromosomal element often carrying one or more genes, and is usually in the form of a circular double-stranded DNA molecule. Plasmids and vectors may also contain additional genetic elements such as autonomously replicating sequences, genome integrating sequences, phage or nucleotide sequences. They may also be linear, circular, or supercoiled, of a single- or double-stranded DNA or RNA, derived from any source. Plasmids and vectors may be constructed by known techniques in which a number of nucleotide sequences have been joined or recombined into a unique construction. Plasmids and vectors generally also include a promoter fragment and DNA sequence for a selected gene product along with appropriate 3' untranslated sequence. Generally, the plasmids of the present invention are stable and self-replicating.

As used herein, the term "anaerobic" refers to an organism, biochemical reaction or process that is active or occurs under conditions of an absence of gaseous $O_2$.

"Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of fermentation until oxygen is unavailable to the microorganism as a terminal electron acceptor.

"Aerobic metabolism" refers to a biochemical process in which oxygen is used as a terminal electron acceptor to convert energy, typically in the form of ATP, from carbohydrates. Aerobic metabolism typically occurs, for example, via the electron transport chain in mitochondria in eukaryotes, wherein a single glucose molecule is metabolized completely into carbon dioxide in the presence of oxygen.

In contrast, "anaerobic metabolism" refers to a biochemical process in which oxygen is not the final acceptor of electrons generated. Anaerobic metabolism can be divided into anaerobic respiration, in which compounds other than oxygen serve as the terminal electron acceptor, and substrate level phosphorylation, in which no exogenous electron acceptor is used and products of an intermediate oxidation state are generated via a "fermentative pathway."

In "fermentative pathways", the amount of NAD(P)H generated by glycolysis is balanced by the consumption of the same amount of NAD(P)H in subsequent steps. For example, in one of the fermentative pathways of certain yeast strains, NAD(P)H generated through glycolysis donates its electrons to acetaldehyde, yielding ethanol. Fermentative pathways are usually active under anaerobic conditions but may also occur under aerobic conditions, under conditions where NADH is not fully oxidized via the respiratory chain.

As used herein, the term "end-product" refers to a chemical compound that is not or cannot be used by a cell, and so is excreted or allowed to diffuse into the extracellular environment. Common examples of end-products from anaerobic fermentation include, but are not limited to, ethanol, acetic acid, formic acid, lactic acid, hydrogen and carbon dioxide.

As used herein, "cofactors" are compounds involved in biochemical reactions that are recycled within the cells and remain at approximately steady state levels. Common examples of cofactors involved in anaerobic fermentation include, but are not limited to, $NAD^+$ and $NADP^+$. In metabolism, a cofactor can act in oxidation-reduction reactions to accept or donate electrons. When organic compounds are broken down by oxidation in metabolism, their energy can be transferred to $NAD^+$ by its reduction to NADH, to $NADP^+$ by its reduction to NADPH, or to another cofactor, $FAD^+$, by its reduction to $FADH_2$. The reduced cofactors can then be used as a substrate for a reductase.

As used herein, a "pathway" is a group of biochemical reactions that together can convert one compound into another compound in a step-wise process. A product of the first step in a pathway may be a substrate for the second step, and a product of the second step may be a substrate for the third, and so on. Pathways of the present invention include, but are not limited to, the pyruvate metabolism pathway the lactate production pathway, the ethanol production pathway, the formate production pathway, and the acetate production pathway.

The term "recombination" or "recombinant" refers to the physical exchange of DNA between two identical (homologous), or nearly identical. DNA molecules. Recombination can be used for targeted gene deletion or to modify the sequence of a gene. The term "recombinant microorganism" and "recombinant host cell" are used interchangeably herein and refer to microorganisms that have been genetically modified to express or over-express endogenous polynucleotides, or to express heterologous polynucleotides, such as those included in a vector, or which have a modification in expression of an endogenous gene.

By "expression modification" it is meant that the expression of the gene, or level of a RNA molecule or equivalent RNA molecules encoding one or more polypeptides or polypeptide subunits, or activity of one or more polypeptides or polypeptide subunits is up regulated or down-regulated, such that expression, level, or activity, is greater than or less than that observed in the absence of the modification.

In one aspect of the invention, genes or particular polynucleotide sequences are partially, substantially, or completely deleted, silenced, inactivated, or down-regulated in order to inactivate the enzymatic activity they encode. Complete deletions provide maximum stability because there is no opportunity for a reverse mutation to restore function. Alternatively, genes can be partially, substantially, or completely deleted, silenced, inactivated, or down-regulated by insertion, deletion, removal or substitution of nucleic acid sequences that disrupt the function and/or expression of the gene.

As used herein, the term "down-regulate" includes the deletion or mutation of a genetic sequence, or insertion of a disrupting genetic element, coding or non-coding, such that the production of a gene product is lessened by the deletion, mutation, or insertion. It includes a decrease in the expression level (i.e., molecular quantity) of an mRNA or protein. "Delete" or "deletion" as used herein refers to a removal of a genetic element such that a corresponding gene is completely prevented from being expressed. In some embodiments, deletion refers to a complete gene deletion. Down-regulation can also occur by causing the repression of genetic elements by chemical or other environmental means, for example by engineering a chemically-responsive promoter element (or other type of conditional promoter) to control the expression of a desired gene product.

As used herein, the term "up-regulate" includes the insertion, reintroduction, mutation, or increased expression of a genetic sequence, such that the production of a gene product is increased by the insertion, reintroduction, or mutation. "Insert" or "insertion" as used herein refers to an introduction of a genetic element such that a corresponding gene is expressed. Up-regulation can also occur by causing the increased expression of genetic elements through an alteration of the associated regulatory sequence.

As used herein, the term "pyruvate metabolism pathway" refers to the collection of biochemical pathways that convert pyruvate into any product, including, but not limited to, ethanol, lactic acid, acetic acid and formate. It also includes the collection of pathways that result in the production of pyruvate, such as glycolysis. Components of the pathway consist of all substrates, cofactors, byproducts, intermediates, end-products, and enzymes in the pathway.

As used herein, the term "lactic acid pathway" refers to the biochemical pathway that converts carbon-containing substrates, such as pyruvate, into the production of lactic acid. Components of the pathway consist of all substrates, cofactors, byproducts, intermediates, end-products, and enzymes in the pathway.

As used herein, the term "acetic acid pathway" refers to the biochemical pathway that converts carbon-containing substrates, such as pyruvate, into the production of acetic acid or other compounds. Components of the pathway consist of all substrates, cofactors, byproducts, intermediates, end-products, and enzymes in the pathway.

As used herein, the term "formate pathway" refers to the biochemical pathway that converts carbon-containing substrates, such as pyruvate, into the production of formate or other compounds. Components of the pathway consist of all substrates, cofactors, byproducts, intermediates, end-products, and enzymes in the pathway.

As used herein, the term "ethanol pathway" refers to the pathway of ethanol production from pyruvate. Components of the pathway consist of all substrates, cofactors, byproducts, intermediates, end-products, and enzymes in the pathway.

As used herein, the term "altered cofactor specificity" or "alteration of cofactor specificity" refers to any change in the cofactor specificity of an enzyme produced by a host cell. In some embodiments altered cofactor specificity includes mutation of a nucleic acid encoding the endogenous enzyme. In some embodiments, altered cofactor specificity includes the expression of a heterologous enzyme from another species with the ability to perform the same chemistry as the endogenous enzyme but with a different cofactor preference. In some embodiments, altered cofactor specificity includes a shift in the preference of an enzyme for one cofactor over another, for example whereas the endogenous enzyme showed preference for the cofactor $NAD^+$, as a result of an alteration of cofactor specificity, the heterologous enzyme would show preference for the cofactor $NADP^+$. Other alterations to cofactor specificity may make the enzyme less specific for a given cofactor, that is, to react with a variety of cofactors without preference. For instance, if an enzyme shows preference for NAD+, an alteration may allow it to react with $NADP^+$ or $NAD^+$ with approximately equal affinity or rate. The term "preference" when applied to an enzyme means that it reacts with a higher rate or affinity for a given substrate than other alternatives.

As used herein, the term "glycolysis" or "glycolytic pathway" refers to the canonical pathway of basic metabolism in which a sugar such as glucose is broken down into more oxidized products, converting energy and compounds required for cell growth. The pathway consists of all substrates, cofactors, byproducts, intermediates end-products, and enzymes in the pathway.

As used herein, the term "alcohol dehydrogenase" or "ADH" is intended to include the enzymes that catalyze the conversion of ethanol into acetylaldehyde. Very commonly, the same enzyme catalyzes the reverse reaction from acetaldehyde to ethanol, which is the direction most relevant to fermentation. Alcohol dehydrogenase includes those enzymes that correspond to Enzyme Commission Number (EC) 1.1.1.1 and 1.1.1.2 and exemplified by the enzymes disclosed in GenBank Accession # U49975, and SEQ ID NOs 1-3, 6-21.

As used herein, the term "acetaldehyde dehydrogenase" or "ALDH" is intended to include the enzymes that catalyze the conversion of acetaldehyde into acetyl-CoA. Very commonly, the same enzyme catalyzes the reverse reaction from acetyl-CoA to acetaldehyde, which is the direction most relevant to fermentation. Acetaldehyde dehydrogenase includes those enzymes that correspond to Enzyme Commission Number (EC) 1.2.1.4 and 1.2.1.10 and exemplified by SEQ ID NOs: 4-21.

As used herein, the term "malate dehydrogenase" or "MDH" is intended to include the enzymes that catalyze the conversion of malate into oxaloacetate. Very commonly, the same enzyme catalyzes the reverse reaction from oxaloacetate to malate. Malate dehydrogenase includes those enzymes that correspond to Enzyme Commission Number (EC) 1.1.1.37, 1.1.1.38, 1.1.5.4, 1.1.1.82, and exemplified by SEQ ID NOs: 22-25.

As used herein, the term "formate dehydrogenase" is intended to include those enzymes capable of converting formate to bicarbonate (carbon dioxide). Formate dehydrogenase includes those enzymes that correspond to EC 1.2.1.43 and EC 1.2.1.2 and exemplified by SEQ ID NOs: 26-31.

As used herein, the term "malic enzyme" is intended to include the enzymes that catalyze the conversion of malate to pyruvate. Malic enzyme includes those enzymes that correspond to Enzyme Commission Number (EC) 1.1.1.38, 1.1.1.39, and 1.1.1.40, and exemplified by GenBank Accession # M19485 and SEQ ID NOs: 32-34.

As used herein, the term "glyceraldehyde-3-phosphate dehydrogenase" is intended to include the enzymes that catalyze the conversion of glyceraldehyde-3-phosphate to D-glycerate 1,3 bisphosphate. Glyceraldehyde-3-phosphate dehydrogenase includes those enzymes that correspond to Enzyme Commission Number (EC) 1.2.1.12 and exemplified by SEQ ID NO: 35 and SEQ ID NO: 36.

As used herein, the term "pyruvate formate lyase" or "PFL" is intended to include the enzymes capable of converting pyruvate to formate and acetyl-CoA. PFL includes those enzymes that correspond to EC 2.3.1.54 and exemplified by SEQ ID NO: 37 and SEQ ID NO: 38.

As used herein, the term "PFL-activating enzymes" is intended to include those enzymes capable of aiding in the activation of PFL. PFL-activating enzymes include those enzymes that correspond to EC 1.97.1.4 and exemplified by SEQ ID NO: 39 and SEQ ID NO: 40.

As used herein, the term "pyruvate-phosphate dikinase" or "PPDK" is intended to include the enzymes capable of converting pyruvate to phosphoenolpyruvate (PEP). PPDK includes those enzymes that correspond to EC 2.7.9.1 and exemplified by SEQ ID NO: 41 and SEQ ID NO: 42.

As used herein, the term "phosphoenolpyruvate carboxykinase" or "PEPCK" is intended to include the enzymes capable of converting PEP to oxaloacetate. PEPCK includes those enzymes that correspond to EC 4.1.1.49 and exemplified by SEQ ID NO: 43 and SEQ ID NO: 44.

As used herein, the term "lactate dehydrogenase" or "LDH" is intended to include the enzymes capable of converting pyruvate to lactate. LDH includes those enzymes that correspond to EC 1.1.1.27 and EC 1.1.1.28 and exemplified by SEQ ID NO: 45 and SEQ ID NO: 46.

As used herein, the term "phosphotransacetylase" or "PTA" is intended to include the enzymes capable of converting acetyl-CoA to acetylphosphate. PTA includes those enzymes that correspond to EC 2.3.1.8 and exemplified by SEQ ID NO: 47 and SEQ ID NO: 48.

As used herein, the term "acetate kinase" or "ACK" is intended to include the enzymes capable of converting acetylphosphate to acetate. ACK includes those enzymes that correspond to EC 2.7.2.1 and exemplified by SEQ ID NO: 49 and SEQ ID NO: 50.

As used herein, the term "bifunctional" is intended to include enzymes that catalyze more than one biochemical reaction step. A specific example of a bifunctional enzyme used herein is an enzyme (AdhE) that catalyzes both the alcohol dehydrogenase and acetaldehyde dehydrogenase reactions.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product in a fermentation process. A feedstock can contain nutrients other than a carbon source.

Biomass can include any type of biomass known in the art or described herein. The terms "lignocellulosic material," "lignocellulosic substrate" and "cellulosic biomass" mean any type of carbon containing feed stock selected from the group consisting of woody biomass, such as recycled wood pulp fiber, sawdust, hardwood, softwood, grasses, sugar-processing residues, agricultural wastes, such as, but not limited to, rice straw, rice hulls, barley straw, corn cobs, cereal straw, wheat straw, canola straw, oat straw, oat hulls, corn fiber, stover, succulents, agave, or any combination thereof.

The term "yield" is defined as the amount of product obtained per unit weight of raw material and may be expressed as gram product per gram substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to ethanol is 0.51 g EtOH per 1 g glucose. As such, a yield of 4.8 g ethanol from 10 g of glucose would be expressed as 94% of theoretical or 94% theoretical yield.

The term "titer" is defined as the strength of a solution or the concentration of a substance in solution. For example, the titer of a product in a fermentation broth is described as gram of product in solution per liter of fermentation broth (g/L) or as g/kg broth.

As used herein, the term "flux" is the rate of flow of molecules through a metabolic pathway, akin to the flow of material in a process.

"Bacteria", or "eubacteria", refers to a domain of prokaryotic organisms. Bacteria include gram-positive (gram+) bacteria and gram-negative (gram−) bacteria.

In some embodiments of the invention, the host cell is a prokaryotic microorganism. In some embodiments, the host cell is a bacterium. In some embodiments, the host cell is able to digest and ferment cellulose. In some embodiments, the host cell is a thermophilic bacterium. In some embodiments, the microorganism is from the genus *Clostridium* or the genus *Caldicellulosiruptor*. In some embodiments, the bacterium is *Clostridium thermocellum, Clostridium cellulolyticum, Clostridium clariflavum, Clostridium phytofermentans, Clostridium acetobutylicum, Caldicellulosiruptor bescii*, or *Caldicellulosiruptor saccharolyticus.*

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

In some embodiments, the host cells of the invention are cultured at a temperature above about 25° C., above about 27° C., above about 30° C., above about 33° C., above about 35° C., above about 37° C., above about 40° C., above about 43° C., above about 45° C., or above about 47° C.

In some embodiments, the host cells of the invention contain genetic constructs that lead to the down-regulation to one or more genes encoding a polypeptide at least about 80%, at least about 85%, at least about 90%, at least about 95%, at least about 96%, at least about 97%, at least about 98%, at least about 99%, or about 100% identical to one or more of the polypeptides encoded by SEQ ID NOs: 38, 40, 42, 44, 46, 48 or 50.

In some embodiments, the host cells of the invention contain genetic constructs that lead to the expression or up-regulation of one or more genes encoding a polypeptide at least about 80%, at least about 85%, at least about 90%, at least about 95%, at least about 96%, at least about 97%, at least about 98%, at least about 99%, or about 100% identical to one or more of the polypeptides encoded by SEQ ID NOs: 2, 5, 7, 9, 11, 13, 15, 17, 19, 21, 23, 25, 27, 29, 31, 33, or 36, or the expression of one or more genes encoded by a polynucleotide at least about 80%, at least about 85%, at least about 90%, at least about 95%, at least about 96%, at least about 97%, at least about 98%, at least about 99%, or about 100% identical to one or more of the polynucleotides encoded by SEQ ID NO: 3 and SEQ ID NO: 34.

The terms "derivative" and "analog" refer to a polypeptide differing from the enzymes of the invention, but retaining essential properties thereof. Generally, derivatives and analogs are overall closely similar, and, in many regions, identical to the enzymes of the invention. The terms "derived-from", "derivative" and "analog" when referring to enzymes of the invention include any polypeptides which retain at least some of the activity of the corresponding native polypeptide or the activity of its catalytic domain.

Derivatives of enzymes disclosed herein are polypeptides which may have been altered so as to exhibit features not found on the native polypeptide. Derivatives can be covalently modified by substitution (e.g. amino acid substitution), chemical, enzymatic, or other appropriate means with a moiety other than a naturally occurring amino acid (e.g., a detectable moiety such as an enzyme or radioisotope). Examples of derivatives include fusion proteins, or proteins which are based on a naturally occurring protein sequence, but which have been altered. For example, proteins can be designed by knowledge of a particular amino acid sequence, and/or a particular secondary, tertiary, and/or quaternary structure. Derivatives include proteins that are modified based on the knowledge of a previous sequence, natural or synthetic, which is then optionally modified, often, but not necessarily to confer some improved function. These sequences, or proteins, are then said to be derived from a particular protein or amino acid sequence. In some embodiments of the invention, a derivative must retain at least about 50% identity, at least about 60% identity, at least about 70% identity, at least about 80% identity, at least about 90% identity, at least about 95% identity, at least about 97% identity, or at least about 99% identity to the sequence the derivative is "derived-from." In some embodiments of the invention, an enzyme is said to be derived-from an enzyme naturally found in a particular species if, using molecular genetic techniques, the DNA sequence for part or all of the enzyme is amplified and placed into a new host cell.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith. D. W., ed.) Academic Press, NY (1993); Computer Analysis of Sequence Data, Part I (Griffin. A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to 75% identical to the amino acid sequences reported herein, at least about 80%, at least about 85%, or at least about 90% identical to the amino acid sequences reported herein, or at least about 95%, at least about 96%, at least about 97%, at least about 98%, at least about 99%, or at least about 100% identical to the amino acid sequences reported herein. Suitable nucleic acid fragments are at least about 70%, at least about 75%, or at least about 80% identical to the nucleic acid sequences reported herein, at least about 80%, at least about 85%, or at least about 90% identical to the nucleic acid sequences reported herein, or at least about 95%, at least about 96%, at least about 97%, at least about 98%, at least about 99%, or at least about 100% identical to the nucleic acid sequences reported herein. Suitable nucleic acid fragments not only have the above identities/similarities but typically encode a polypeptide having at least about 50 amino acids, at least about 100 amino acids, at least about 150 amino acids, at least about 200 amino acids, or at least about 250 amino acids.

Codon Optimization

In some embodiments of the present invention, exogenous genes may be codon-optimized in order to express the polypeptide they encode most efficiently in the host cell. Methods of codon optimization are well known in the art. See, e.g. Welch et al. "Designing genes for successful protein expression." *Methods Enzymol.* 2011. 498:43-66.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp et al., "The Codon Adaptation Index: a Measure of Directional Synonymous Codon Usage Bias, and Its Potential Applications." *Nucleic Acids Research* 1987. 15: 1281-1295, which is incorporated by reference herein in its entirety.

A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can effect transcription negatively. Therefore, it can be useful to remove a run by, for example, replacing at least one nucleotide in the run with another nucleotide. Furthermore, specific restriction enzyme sites may be removed for molecular cloning purposes by replacing at least one nucleotide in the restriction site with another nucleotide. Examples of such restriction enzyme sites include PacI, AscI, BamHI, BglII, EcoRI and XhoI. Additionally, the DNA sequence can be checked for direct repeats, inverted repeats and mirror repeats with lengths of about 5, 6, 7, 8, 9 or 10 bases or longer. Runs of "As" or "Ts", restriction sites and/or repeats can be modified by replacing at least one codon within the sequence with the "second best" codons, i.e., the codon that occurs at the second highest frequency for a particular amino acid within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six triplets each, whereas tryptophan and methionine are coded for by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Scr (S) | TAT Tyr (Y) | TGT Cys(C) |
| | TTC Phe (F) | TCC Scr (S) | TAC Tyr (Y) | TGC |
| | TTA Leu (L) | TCA Scr (S) | TAA Ter | TGA Ter |
| | TTG Leu (L) | TCG Scr (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCGAla (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Alteration of Cofactor Specificity

In some embodiments, at least one enzyme with altered cofactor specificity relative to the endogenous enzyme in a pyruvate metabolism pathway is expressed in a recombinant prokaryotic host cell.

In one embodiment, an alcohol dehydrogenase (ADH) with altered cofactor specificity relative to the endogenous alcohol dehydrogenase is expressed in a host microorganism. In one embodiment, an alcohol dehydrogenase with altered cofactor specificity relative to the endogenous alcohol dehydrogenase is expressed in a host microorganism, and additional genetic modifications are introduced to increase the yield of the ethanol pathway. Such modifications include down-regulating alternative pyruvate metabolism pathways, including the formate, acetic acid, or lactic acid pathways. In some embodiments the ADH is singular. In some embodiments the ADH is part of a bifunctional enzyme. In some embodiments the microorganism is a cellulolytic organism. In some embodiments, the microorganism is thermophilic. In some embodiments, the organism is anaerobic. In some embodiments, the alteration in cofactor specificity is accomplished by introducing mutations in a native alcohol dehydrogenase gene. A systematic method for rational engineering of alterations in cofactor specificity has been described in Khoury et al. "Computational design of *Candida boidinii* xylose reductase for altered cofactor specificity." *Protein Sci.* 2009 18(10): 2125-38. Briefly, Khoury et al. describes that experimental methods for altering the cofactor specificity of enzymes include combining structural analysis with site directed mutagenesis to redesign proteins to accept alternate cofactors. In Khoury et al., a computational approach was taken and a computational workflow was introduced that is based on the iterative protein redesign and optimization algorithm (IPRO). Two implicit solvation models were added to the IPRO: Generalized Born with molecular volume integration and Generalized Born with simple switching. Using this computational method, in one instance, the experimental specificity of a predicted design showed a fivefold decrease in catalytic activity with the endogenous cofactor, and a 26% increase in catalytic activity with a cofactor for which cofactor specificity was introduced by mutations. In some embodiments an alcohol dehydrogenase gene with an alternate cofactor specificity in introduced. In some embodiments, expression of the native alcohol dehydrogenase is down-regulated and an alcohol dehydrogenase gene with an alternate cofactor specificity from a different species is introduced. In some embodiments, the alcohol dehydrogenase with alternate cofactor specificity is from a genus selected from the group including *Thermococcus, Acinetobacter, Clostridium, Kluyveromyces, Saccharomyces, Bacillus, Staphylococcus, Streptococcus, Enterococcus, Leuconostoc, Lactobacillus, Lactococcus, Corynebacterium, Moorella. Thermoanaerobacterium* or *Thermoanaerobacter*. In some embodiments, the newly introduced cofactor specificity is for an ADH that uses NADPH instead of NADH. In some embodiments, the enzyme in the formate pathway, acetic acid pathway or lactic acid pathway is encoded by pyruvate formate lyase (PFL), pyruvate formate lyase activating enzyme, pyruvate-phosphate dikinase (PPDK), phosphoenolpyruvate carboxykinase (PEPCK), lactate dchydrogenase (LDH), phosphotransacetylase (PTA), and/or acetate kinase (ACK). In some embodiments, strains with altered cofactor specificity can then be optimized by growth-coupled selection. Specifically, continuous culture or serial dilution cultures can be performed to select for cells that grow faster and by necessity, produce ethanol faster.

In one embodiment, an acetaldehyde dehydrogenase (ALDH) with altered cofactor specificity relative to the endogenous acetaldehyde is expressed in a host microorganism. In one embodiment, an acetaldehyde dehydrogenase with altered cofactor specificity relative to the endogenous acetaldehyde enzyme is expressed in a host microorganism, and additional genetic modifications are introduced to increase the yield of the ethanol pathway. Such modifications include down-regulating alternative pyruvate metabolism pathways, including the formate, acetic acid, or lactic acid pathways. In some embodiments, the ALDH is singular. In some embodiments, the ALDH is part of a bifunctional enzyme. In some embodiments, the alteration in cofactor specificity is accomplished by introducing mutations in a native acetaldehyde dehydrogenase gene. In some embodiments, an acetaldehyde dehydrogenase gene with an alternate cofactor specificity from a different species is introduced. In some embodiments, the native acetaldehyde enzyme is down-regulated and an acetaldehyde dehydrogenase gene with an alternate cofactor specificity from a different species is introduced. In some embodiments the acetaldehyde dehydrogenase with alternate cofactor specificity is from a genus selected from the group including *Entamoeba, Cryptosporidium, Escherichia, Salmonella, Yersinia, Shigella, Pectobacterium, Erwinia, Photorhabdus, Enterobacter, Cronobacter, Klebsiella, Citrobacter, Serratia, Proteus, Edwardsiella, Dickeya, Xenorhabdus, Pantoea, Rahnella, Pasteurella, Actinobacillus, Aggregatibacter, Vibrio, Aliivibrio, Pseudomonas, Cellvibrio, Shewanella, Alkalilimnicola, Aeromonas, Aeromonas, Ralstonia, Cupriavidus, Burkholderia, Pusillimonas, Polaromonas, Acidovorax, Alicycliphilus, Methylibium, Leptothrix, Pelobacter, Desulfovibrio, Rhodopseudomonas, Xanthobacter, Novosphingobium, Sphingomonas, Sphingobium, Azospirillum, Bacillus, Geobacillus, Staphylococcus, Listeria, Exiguobacterium, Brevibacillus, Geobacillus, Paenibacillus, Lactococcus, Streptococcus, Lactobacillus, Enterococcus, Oenococcus, Leuconostoc, Clostridium, Alkaliphilus, Candidatus, Desulfitobacterium, Ruminococcus, Thermaerobacter, Thermoanaerobacter, Moorella, Thermoanaerobacterium, Halothermothrix, Nocardia, Rhodococcus, Streptomyces, Jonesia, Xylanimonas, Sanguibacter, Cellulomonas, Thermomonospora, Nakamurella, Amycolatopsis, Salinispora, Salinispora, Micromonospora, Bifidobacterium, Gardnerella, Conexibacter, Atopobium, Olsenella, Treponema, Spirochaeta, Candidatus, Porphyromonas, Leptotrichia, Synechococcus, Cyanothece, Nostoc, Roseiflexus, Chloroflexus, Thermomicrobium, Thermus*. In some embodiments, the newly introduced cofactor specificity is for an ALDH that uses NADPH instead of NADH. In some embodiments, the enzyme in the formate pathway, acetic acid pathway or lactic acid pathway is encoded by pyruvate formate lyase (PFL), pyruvate formate lyase activating enzyme, pyruvate-phosphate dikinase (PPDK), phosphoenolpyruvate carboxykinase (PEPCK), lactate dehydrogenase (LDH), phosphotransacetylase (PTA), and/or acetate kinase (ACK).

In another embodiment, malate dehydrogenase (MDH) with altered cofactor specificity relative to the endogenous malate dehydrogenase is expressed in a host microorganism. In another embodiment, malate dehydrogenase with altered cofactor specificity relative to the endogenous malate dehydrogenase is expressed in a host microorganism, and additional genetic modifications are introduced to increase the yield of the ethanol pathway. Such modifications include down-regulating alternative pyruvate metabolism pathways, including the formate, acetic acid, or lactic acid pathways. In some embodiments, the alteration in cofactor specificity is accomplished by introducing mutations in a native malate dehydrogenase gene. In some embodiments, a malate dehydrogenase gene with an alternate cofactor specificity from a different species is introduced. In some embodiments, the native gene for malate dehydrogenase is down-regulated, and a malate dehydrogenase gene with an alternate cofactor specificity from a different species is introduced. In some embodiments the malate dehydrogenase with alternate cofactor specificity is from a genus selected from the group including *Clamydomonas, Aeropyrum, Bacillus, Staphylococcus, Streptococcus. Enterococcus, Leuconostoc, Lactobacillus, Lactococcus, Corynebacterium, Methanocaldoaldcoccus, Thermoanaerobacterium* or *Arabidopsis*. In some embodiments, the newly introduced cofactor specificity is for a MDH that uses NADPH instead of NADH. In some embodiments, the enzyme in the formate pathway, acetic acid pathway or lactic acid pathway is encoded by pyruvate formate lyase (PFL), pyruvate formate lyase activating enzyme, pyruvate-phosphate dikinase (PPDK), phosphoenolpyruvate carboxykinase (PEPCK), lactate dehydrogenase (LDH), phosphotransacetylase (PTA), and/or acetate kinase (ACK).

In another embodiment, formate dehydrogenase with altered cofactor specificity relative to the endogenous formate dehydrogenase is expressed in a host microorganism. In some embodiments, the alteration in cofactor specificity is accomplished by introducing mutations in a native formate dehydrogenase gene. In another embodiment, formate dehydrogenase with altered cofactor specificity relative to the endogenous formate dehydrogenase is expressed in a host microorganism, and additional genetic modifications are introduced to increase the yield of the ethanol pathway. Such modifications include down-regulating alternative pyruvate metabolism pathways, including the formate, acetic acid, or lactic acid pathways. In some embodiments, a formate dehydrogenase gene with an alternate cofactor specificity from a different species is introduced. In some embodiments, the native gene for formate dehydrogenase is down-regulated, and a formate dehydrogenase gene with an alternate cofactor specificity from a different species is introduced. In some embodiments the formate dehydrogenase with alternate cofactor specificity is from a genus selected from the group including Moorella, *Bacillus, Staphylococcus. Streptococcus, Enterococcus, Leuconostoc, Lactobacillus, Lactococcus, Corynebacterium, Thermoanaerobacterium* or *Pseudomonas*. In some embodiments, the newly introduced cofactor specificity is for a formate dehydrogenase that uses NADPH instead of NADH. In some embodiments, the enzyme in the formate pathway, acetic acid pathway or lactic acid pathway is encoded by pyruvate formate lyase (PFL), pyruvate formate lyase activating enzyme, pyruvate-phosphate dikinase (PPDK), phosphoenolpyruvate carboxykinase (PEPCK), lactate dehydrogenase (LDH), phosphotransacetylase (PTA), and/or acetate kinase (ACK).

In another embodiment, malic enzyme with altered cofactor specificity relative to the endogenous malic enzyme is expressed in a host microorganism. In another embodiment, malic enzyme with altered cofactor specificity relative to the endogenous malic enzyme is expressed in a host microorganism, and additional genetic modifications are introduced to increase the yield of the ethanol pathway. Such modifications include down-regulating alternative pyruvate metabolism pathways, including the formate, acetic acid, or lactic acid pathways. In some embodiments, the alteration in cofactor specificity is accomplished by introducing mutations in a native malic enzyme gene. In some embodiments, a malic enzyme gene with an alternate cofactor specificity from a different species is introduced. In some embodiments, the native gene for malic enzyme is down-regulated and a malic enzyme gene with an alternate cofactor specificity from a different species is introduced. In some embodiments the malic enzyme with alternate cofactor specificity is from a genus selected from the group including *Clostridium, Escherichia, Schizosaccharomyces, Sinorhizobium, Bacillus, Staphylococcus, Streptococcus, Enterococcus, Leuconostoc, Lactobacillus, Lactococcus, Corynebacterium, Thermoanaerobacterium* or *Aerobacter*. In some embodiments, the newly introduced cofactor specificity is a malic enzyme that uses $NAD^+$ instead of $NADP^+$. In some embodiments, the enzyme in the formate pathway, acetic acid pathway or lactic acid pathway is encoded by pyruvate formate lyase (PFL), pyruvate formate lyase activating enzyme, pyruvate-phosphate dikinase (PPDK), phosphoenolpyruvate carboxykinase (PEPCK), lactate dehydrogenase (LDH), phosphotransacetylase (PTA), and/or acetate kinase (ACK).

In another embodiment, glyceraldehyde-3-phosphate dehydrogenase with altered cofactor specificity relative to the endogenous glyceraldehyde-3-phosphate dehydrogenase is expressed in a host microorganism. In another embodiment, glyceraldehyde-3-phosphate dehydrogenase with altered cofactor specificity relative to the endogenous glyceraldehyde-3-phosphate dehydrogenase is expressed in a host microorganism, and additional genetic modifications are introduced to increase the yield of the ethanol pathway. Such modifications include down-regulating alternative pyruvate metabolism pathways, including the formate, acetic acid, or lactic acid pathways. In some embodiments, the alteration in cofactor specificity is accomplished by introducing mutations in a native glyceraldehyde-3-phosphate dehydrogenase gene. In some embodiments, a glyceraldehyde-3-phosphate dehydrogenase gene with an alternate cofactor specificity from a different species is introduced. In some embodiments, the native gene for glyceraldehyde-3-phosphate is down-regulated and a glyceraldehyde-3-phosphate gene with an alternate cofactor specificity from a different species is introduced. In some embodiments the glyceraldehyde-3-phosphate with alternate cofactor specificity is from a genus selected from the group including *Clostridium, Moorella, Micrococcus, Methanococcus, Methanocaldococcus, Thermococcus, Bacillus, Staphylococcus, Streptococcus, Enterococcus, Leuconostoc, Lactobacillus, Lactococcus, Corynebacterium*, or *Thermoanaerobacterium*. In some embodiments, the newly introduced cofactor specificity is a malic enzyme that uses $NAD^+$ instead of $NADP^+$. In some embodiments, the enzyme in the formate pathway, acetic acid pathway or lactic acid pathway is encoded by pyruvate formate lyase (PFL), pyruvate formate lyase activating enzyme, pyruvate-phosphate dikinase (PPDK), phosphoenolpyruvate carboxykinase (PEPCK), lactate dehydrogenase (LDH), phosphotransacetylase (PTA), and/or acetate kinase (ACK).

In some embodiments, alcohol dehydrogenase with an altered cofactor specificity relative to the endogenous alcohol dehydrogenase is expressed with at least one other enzyme with an altered cofactor specificity relative to the endogenous enzyme from the group consisting of glyceraldehyde-3-phosphate dehydrogenase, acetaldehyde dehydrogenase, malate dehydrogenase, formate dehydrogenase, and malic enzyme. In some embodiments, acetaldehyde dehydrogenase with an altered cofactor specificity relative to the endogenous acetaldehyde dehydrogenase is expressed with at least one other enzyme with an altered cofactor specificity relative to the endogenous enzyme from the group consisting of glyceraldehyde-3-phosphate dehydrogenase, alcohol dehydrogenase, malate dehydrogenase, formate dehydrogenase, and malic enzyme. In some embodiments, malate dehydrogenase with an altered cofactor specificity relative to the endogenous malate dehydrogenase is expressed with at least one other enzyme with an altered cofactor specificity relative to the endogenous enzyme from the group consisting of glyceraldehyde-3-phosphate dehydrogenase, alcohol dehydrogenase, acetaldehyde dehydrogenase, formate dehydrogenase, and malic enzyme. In some embodiments, formate dehydrogenase with an altered cofactor specificity relative to the endogenous formate dehydrogenase is expressed with at least one other enzyme with an altered cofactor specificity relative to the endogenous enzyme from the group consisting of glyceraldehyde-3-phosphate dehydrogenase, alcohol dehydrogenase, acetaldehyde dehydrogenase, malate dehydrogenase, and malic enzyme. In some embodiments, malic enzyme with an altered cofactor specificity relative to the endogenous malic enzyme is expressed with at least one other enzyme with an altered cofactor specificity relative to the endogenous enzyme from the group consisting of glyceraldehyde-3-phosphate dehydrogenase alcohol dehydrogenase, acetaldehyde dehydrogenase, malate dehydrogenase, and formate dehydrogenase.

Ethanol Production

For a microorganism to produce ethanol most economically, it is desired to produce a high yield. In one embodiment, the only product produced is ethanol. Extra products lead to a reduction in product yield and an increase in capital and operating costs, particularly if the extra products have little or no value. Extra products also require additional capital and operating costs to separate these products from ethanol.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

In some embodiments of the invention where redirected carbon flux generates increased ethanol production, the ethanol output can be improved by growth-coupled selection. For example, continuous culture or serial dilution cultures can be performed to select for cells that grow faster and/or produce ethanol (or any desired product) more efficiently on a desired feedstock.

One embodiment of the present invention relates to a method of producing ethanol using a microorganism described herein wherein said microorganism is cultured in the presence of a carbon containing feedstock for sufficient time to produce ethanol and, optionally, extracting the ethanol.

Ethanol may be extracted by methods known in the art. See, e.g., U.S. Appl. Pub. No. 2011/0171709, which is incorporated herein by reference.

Another embodiment of the present invention relates to a method of producing ethanol using a co-culture composed of at least two microorganisms in which at least one of the organisms is an organism described herein, and at least one of the organisms is a genetically distinct microorganism. In some embodiments, the genetically distinct microorganism is a yeast or bacterium. In some embodiments the genetically distinct microorganism is any organism from the genus *Issatchenkia, Pichia, Clavispora, Candida, Hansenula, Kluyveromyces, Saccharomyces, Trichoderma, Thermoascus, Escherichia, Clostridium, Caldicellulosiruptor, Thermoanaerobacter* and *Thermoanaerobacterium.*

In some embodiments, the recombinant microorganism produces about 2 to about 3 times more ethanol than a wildtype, non-recombinant organism; at least about 1.5 to at least about 2 times more ethanol than a wildtype, non-recombinant organism; at least about 1.5 to at least about 5 times more ethanol than a wildtype, non-recombinant organism; at least about 1.5 to at least about 7 times more ethanol than a wildtype, non-recombinant organism; at least about 1.5 to at least about 10 times more ethanol than a wildtype, non-recombinant organism; at least about 1.5 to at least about 15 times more ethanol than a wildtype, non-recombinant organism; at least about 1.5 to at least about 20 times more ethanol than a wildtype, non-recombinant organism; at least about 1.5 to at least about 30 times more ethanol than a wildtype, non-recombinant organism; at least about 1.5 to at least about 50 times more ethanol than a wildtype, non-recombinant organism; at least about 1.5 to at least about 75 times more ethanol than a wildtype, non-recombinant organism; at least about 1.5 to at least about 100 times more ethanol than a wildtype, non-recombinant organism.

In some embodiments, the recombinant microorganism produces at least about 0.5 g/L ethanol to at least about 2 g/L ethanol, at least about 0.5 g/L ethanol to at least about 3 g/L ethanol, at least about 0.5 g/L ethanol to at least about 5 g/L ethanol, at least about 0.5 g/L ethanol to at least about 7 g/L ethanol, at least about 0.5 g/L ethanol to at least about 10 g/L ethanol, at least about 0.5 g/L ethanol to at least about 15 g/L ethanol, at least about 0.5 g/L ethanol to at least about 20 g/L ethanol, at least about 0.5 g/L ethanol to at least about 30 g/L ethanol, at least about 0.5 g/L ethanol to at least about 40 g/L ethanol, at least about 0.5 g/L ethanol to at least about 50 g/L ethanol, at least about 0.5 g/L ethanol to at least about 75 g/L ethanol, or at least about 0.5 g/L ethanol to at least about 99 g/L ethanol per 24 hour incubation on a carbon-containing feed stock.

In some embodiments, the recombinant microorganism produces ethanol at least about 55% to at least about 75% of theoretical yield, at least about 50% to at least about 80% of theoretical yield, at least about 45% to at least about 85% of theoretical yield, at least about 40% to at least about 90% of theoretical yield, at least about 35% to at least about 95% of theoretical yield, at least about 30% to at least about 99% of theoretical yield, or at least about 25% to at least about 99% of theoretical yield.

In some embodiments, methods of producing ethanol can comprise contacting a biomass feedstock with a host cell or co-culture of the invention and additionally contacting the biomass feedstock with externally produced saccharolytic enzymes. Exemplary externally produced saccharolytic enzymes are commercially available and are known to those of skill in the art.

EXAMPLES

Example 1

Alteration of Cofactor Specificity of Alcohol Dehydrogenase

Figure 2:
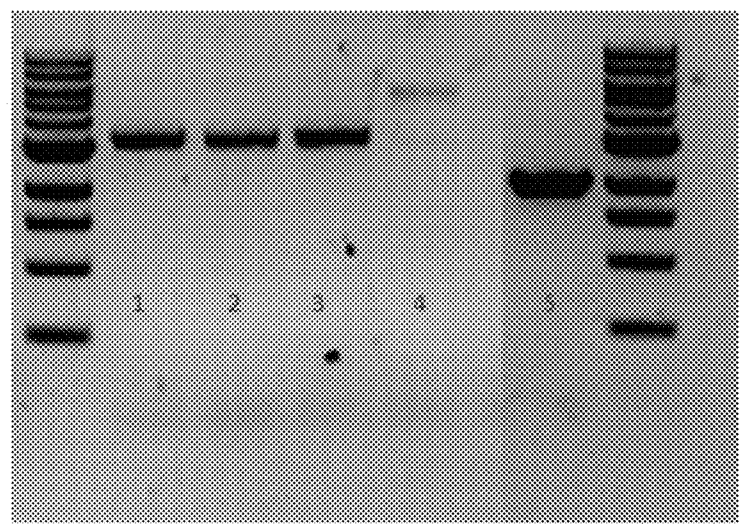
Figure 3:
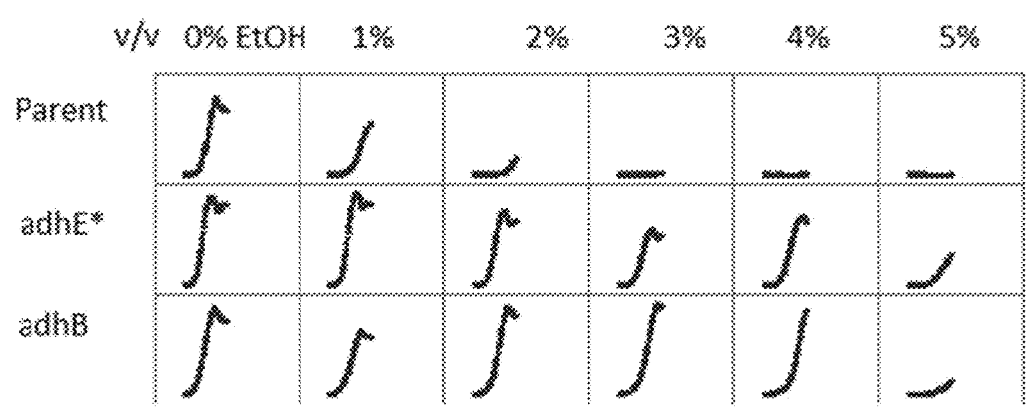
Figure 4:
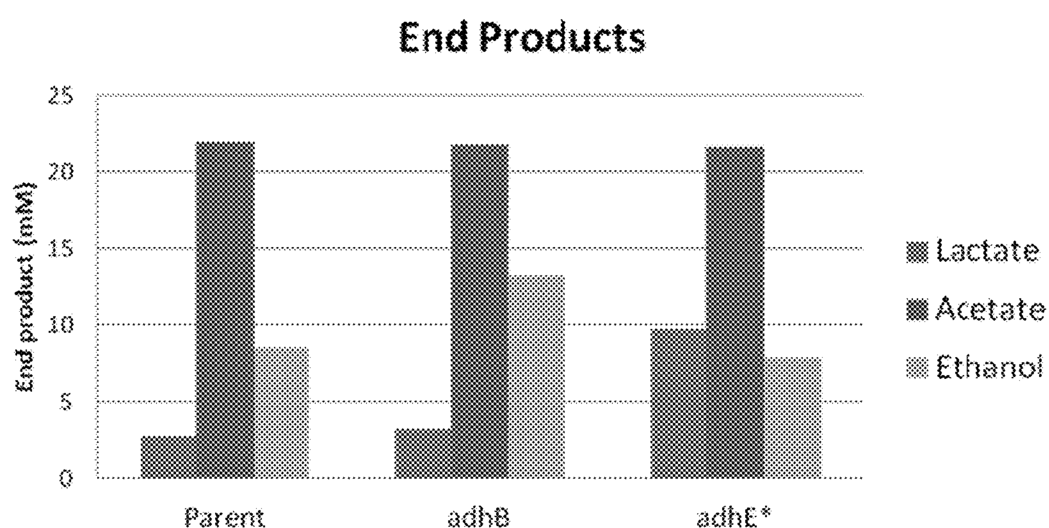
FIG. 4 depicts (A) the concentrations of end products in fermentations of rich medium (CTFUD) with 15 mM cellobiose. 15 mM cellobiose is equivalent to 29 mM glucose in the same strains as shown in FIG. 4; and, (B) the total carbon from end products in the same strains. End products were measured by HPLC.
Figure 4:
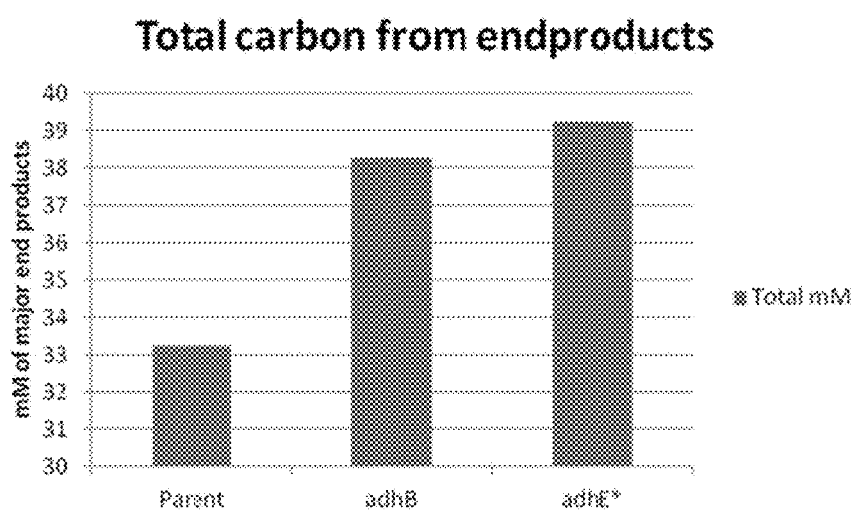

In one embodiment the gene adhB from *Thermoanaerobacter pseudethanolicus* was introduced into the chromosome of *Clostridium thermocellum* to create strain "M1726+adhB." This gene encodes a bifunctional acetaldehyde dehydrogenase-alcohol dehydrogenase (reactions 4 & 5 above and in FIG. 1), but differs from the native alcohol dehydrogenase activity of *C. thermocellum* in that it shows higher reaction rates with NADPH than NADH. This gene is the secondary ADH described in Burdette and Zeikus, "Purification of acetaldehyde dehydrogenase and alcohol dehydrogenases from *Thermoanaerobacter ethanolicus* 39E and characterization of the secondary-alcohol dehydrogenase (2 degrees Adh) as a bifunctional alcohol dehydrogenase-acetyl-CoA reductive thioesterase." *Biochem. J.* 1994. 302: 163-170 and in Burdette et al. *Biochem J.* 1996; 316:115-22 and Burdette et al., "Cloning and expression of the gene encoding the *Thermoanacrobacter ethanolicus* 39E secondary-alcohol dehydrogenase and biochemical characterization of the enzyme." *Biochem J.* 1996. 316:115-22. Introducing this gene helps to relieve the problem of overabundance of NADPH in the pathway from cellobiose to ethanol. The method for constructing this strain is based on that described in Argyros et al. "High ethanol titers from cellulose using metabolically engineered thermophilic, anaerobic microbes." *Appl. Env. Microbiol.,* 2011 doi: 10.1128/AEM.00646-11 (epub ahead of publication). The adhB gene was amplified by PCR from the *T. pseudethanolicus* strain ATCC 33223 using the following primers: ataagctatatatgaagggagaatggagatgaacaatagacaacccctttctgtg (SEQ ID NO: 51) and acaagaaacctttgtatattttttagtccatatcttctcagaattctttctcctccttcttttatcc. (SEQ ID NO: 53). The enolase promoter was amplified from *C. thermocellum* using the following two primers: aaaaaccggcatattggtgttaagtgaaagacgacggcagggaaatattaaaatggaaatgttgaaaaaatg (SEQ ID NO: 54) and caagatcacagaaaggggttgtctattgttcatctccattctccctcatatagc. (SEQ ID NO: 55) These two PCR products were fused by Overlap Extension PCR. The plasmid pDGO-50 was digested with the restriction enzyme PvuII. The digested plasmid, enolase and adhB PCR products were fused by recombination using the method of Gibson et al. to generate plasmid pJL7. "Enzymatic Assembly of Overlapping DNA Fragments." *Methods Enzymol.* 2011. 498: 349-61. The plasmid was transformed into *C. thermocellum*, followed by selection for thiamphenicol and FuDR resistance to identify cells in which recombination had taken place such that hpt was replaced by adhB from the plasmid. PCR using primers outside of the flanking regions (gagcgatgacaagggagtaattttagatc (SEQ ID NO: 56) and ttcgactatttcccttagctcctctttctc (SEQ ID NO: 57)) showed a larger band than the size observed from wild type, indicating successful integration (FIG. 2). A biochemical assay of alcohol dehydrogenase activity was performed using cell extracts, and the mutants showed 10-fold higher activity with NADPH than with NADH. The mutant also showed higher resistance to ethanol, growing at 4% ethanol (FIG. 3). The mutant made 50% more ethanol than the parent strain (8.51 mM versus 13.23 mM, FIG. 4).

Example 2

Alteration of Cofactor Specificity of Malate Dehydrogenase

Figure 5:
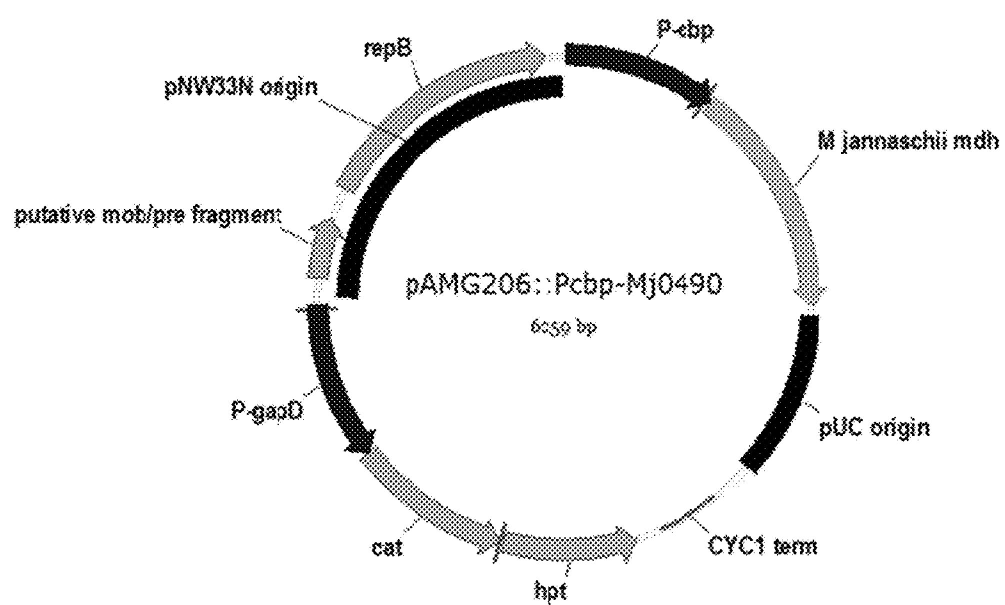
FIG. 5 depicts a diagram of the plasmid pAMG206::Pcbp-Mj_mdh used to introduce a heterologous copy of a malate dehydrogenase gene with altered cofactor specificity into *C. thermocellum.*

In another embodiment the gene for malate dehydrogenase from *Methanococcus janaschii* was cloned into a replicating plasmid in *C. thermocellum*. This gene is described in Madern D., "The putative L-lactate dehydrogenase from *Methanococcus jannaschii* is an NADH-dependent L-malate dehydrogenase." *Mol Microbiol.* 2000. 37(6): 1515-20. The gene was fused to the *C. thermocellum* cbp promoter and cloned onto the *E. coli-C. thermocellum* shuttle vector pAMG206 (FIG. 5 and SEQ ID NO: 52). The mdh gene was PCR amplified from *M. jannaschii* genomic DNA using primers TTTAAGGAGGACGAAAGATGAAAGTTACAATTATAGGAGCTTCTG (SEQ ID NO: 58) and TTAAGGGATTTTGGTTTATAAGTTTTTAACTTCTCACAGTATTT (SEQ ID NO: 59). The cbp promoter was PCR amplified with primers CTTTCGTCCTCCTTAAAATTTTCG (SEQ ID NO: 60) and AAGCCTCCTAAATTCACTAGGAGTCGTGACTAAGAACGTCAAAG (SEQ ID NO: 61). The PCR products were recombined into plasmid pAMG206 digested with restriction endonucleases SpeI and NotI. This plasmid was then transformed into *C. thermocellum* strains with mutations in hpt or hpt and hydG via electroporation using described methods (Olson et al., "Deletion of the Cel48S cellulase from *Clostridium thermocellum.*" *PNAS* 2010. 107(41): 17727-32).

Example 3

Alteration of Cofactor Specificity of Alcohol Dehydrogenase and Elimination of Alternate End-Products In another embodiment, the strain described above expressing adhB is further manipulated as described in Argyros et al. "High ethanol titers from cellulose using metabolically engineered thermophilic, anaerobic microbes." *Appl. Env. Microbiol.,* 2011 doi:10.1128/AEM.00646-11 (epub ahead of publication) to eliminate the production of lactate and acetate. It is then further optimized by growth-coupled selection using serial dilution cultures.

Example 4

Alteration of Cofactor Specificity of Malate Dehydrogenase and Elimination of Alternate End-Products In another embodiment, the strain described above expressing malate dehydrogenase from *M. jannaschii* is further manipulated as described in Argyros et al. "High ethanol titers from cellulose using metabolically engineered thermophilic, anaerobic microbes." *Appl. Env. Microbiol.,* 2011 doi:10.1128/AEM.00646-11 (epub ahead of publication) to eliminate the production of lactate and acetate. It is then further optimized by growth-coupled selection using serial dilution cultures.

Example 5

Alteration of Cofactor Specificity of Malic Enzyme

In another embodiment the gene for malic enzyme from *Geobacillus stearothermophilus* (formerly *Bacillus stearothermophilus*) is cloned into the hpt locus of *C. thermocellum*. This gene is described in Kobayashi et al., "Structure and properties of malic enzyme from *Bacillus stearothermophilus*" *J Biol Chem.* 1989. February 264(6):3200-5.

Example 6

Alteration of Cofactor Specificity of Malic Enzyme and Elimination of Alternate End-Products In another embodiment, the strain described above expressing malic enzyme from *G. stearothermophilus* is further manipulated as described in Argyros et al. "High ethanol titers from cellulose using metabolically engineered thermophilic, anaerobic microbes." *Appl. Env. Microbiol.,* 2011 doi:10.1128/AEM.00646-11 (epub ahead of publication) to eliminate the production of lactate and acetate. It is then further optimized by growth-coupled selection using serial dilution cultures.

Example 7

Further Alternation of Cofactor Specificity of Alcohol Dehydrogenase

In other embodiments, ADH genes found in Table 1 are PCR amplified from the indicated organisms and heterologously expressed in *C. thermocellum*.

TABLE 2

ADH Genes.

| Genbank ID | Organism | Cofactor Specificity | Reference |
|---|---|---|---|
| SEQ ID NO 6, 7 | *T. Saccharolyticum* wild type | NADH | Shaw et al. "Metabolic engineering of a thermophilic bacterium to produce ethanol at high yield." *PNAS* 2008. 105(37): 13769-74. |
| SEQ ID NO 8-15 | *T. Saccharolyticum* adapted strains | unmeasured | |
| SEQ ID NO 16-21 | *C. Thermocellum* ethanol adapted | NADPH | Brown et al. "Mutant alcohol dehydrogenase leads to improved ethanol tolerance in *Clostridium thermocellum*." 2011. 108(33): 13752-7. |
| AAG01186.1 | *T. ethanolicus* | NADH/NADPH | Shaw et al. "Metabolic engineering of a thermophilic bacterium to produce ethanol at high yield." *PNAS* 2008. 105(37): 13769-74. |
| CAA46053.1 | *T. brockii* | NADH/NADPH | Shaw et al. "Metabolic engineering of a thermophilic bacterium to produce ethanol at high yield." PNAS 2008. 105(37): 13769-74. |
| YOL086C | *S. cerevisiae* | NADH | Suwannarangsee et al. "Characterization of alcohol dehydrogenase 1 of the thermotolerant methylotrophic yeast *Hansenula polymorpha*" 2010. *Appl. Microbiol. Biotechnol*. 2010. 88 (2), 497-507 |
| CAG98731.1 | *K. lactis* | NADH/NADPH | Bozzi et al. "Structural and biochemical studies of alcohol dehydrogenase isozymes from *Kluyveromyces lactis. Biochem Biophys Acta*, 1997. 1339(1): 133-42. |
| ADM49192.1 | *H. polymorpha* (*Pichia angusta*) | NADH | Suwannarangsee et al. "Characterization of alcohol dehydrogenase 1 of the thermotolerant methylotrophic yeast *Hansenala polymorpha*" 2010. *Appl. Microbiol. Biotechnol*. 2010. 88 (2), 497-507 |
| P06758.3 | *Z. mobilis* | NADH | Conway et al. "Cloning and sequencing of the alcohol dehydrogenase II gene from *Zymomonas mobilis*" *J. Bacteriol*. 1987. 169 (6), 2591-2597. |
| BAA14411.1 | *G. stearothermophilus* | NADH | Sadoka and Imanaka "Cloning and sequencing of the gene coding for alcohol dehydrogenase of *Bacillus stearothermophilus* and rational shift of the optimum pH" *J. Bacteriol*. 1992. 174 (4), 1397-1402 (1992). |
| EU919177 | *Thermococcus* strain ES1 | NADPH | Ying et al. "Molecular characterization of the recombinant iron-containing alcohol dehydrogenase from the hyperthermophilic *Archaeon*, *Thermococcus* strain ES1." *Extremophiles* 2008. 13 (2), 299-311. |
| CAZ39599.1 | *T. mathranii* | NADH | Yao and Mikkelsen. "Identification and overexpression of a bifunctional aldehyde/alcohol dehydrogenase responsible for ethanol production in *Thermoanaerobacter mathranii*." *J. Mol. Microbiol Biotechnol*. 2008. 19(3): 123-33. |
| CAZ39597.1 | *T. mathranii* | NADH | Yao and Mikkelsen. "Identification and overexpression of a bifunctional aldehyde/alcohol dehydrogenase responsible for ethanol production in *Thermoanaerobacter mathranii*." *J. Mol. Microbiol Biotechnol*. 2008. 19(3): 123-33. |

INCORPORATION BY REFERENCE

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant cellulolytic *Clostridium* host cell comprising at least one heterologous nucleic acid sequence encoding a bifunctional alcohol-acetaldehyde dehydrogenase, wherein the bifunctional alcohol-acetaldehyde dehydrogenase is AdhE;

wherein the bifunctional AdhE is encoded by a heterologous nucleic acid identical to a polynucleotide that encodes the polypeptide of SEQ ID NO:21, wherein the bifunctional AdhE uses NADPH as a cofactor instead of NADH;

wherein the recombinant *Clostridium* host cell further comprises a genetic modification that leads to the down-regulation of the native enzyme lactate dehydrogenase;

and wherein the recombinant *Clostridium* host cell has an increased production of ethanol compared to a wildtype cellulolytic *Clostridium* cell without the heterologous nucleic acid and the down-regulation of the native enzyme lactate dehydrogenase.

2. The recombinant cellulolytic *Clostridium* host cell of claim 1, wherein the recombinant host cell further comprises a genetic modification that leads to the down-regulation of the native alcohol dehydrogenase and/or acetaldehyde dehydrogenase.

3. The recombinant cellulolytic *Clostridium* host cell of claim 1, wherein the host cell is selected from the group consisting of *Clostridium thermocellum, Clostridium cellulolyticum, Clostridium clariflavum*, and *Clostridium phytofermentans*.

4. The recombinant cellulolytic *Clostridium* host cell of claim 1, wherein the heterologous nucleic acid encoding the bifunctional alcohol-acetaldehyde dehydrogenase is at least about 99% identical to the polynucleotide of SEQ ID NO 20.

5. The recombinant cellulolytic *Clostridium* host cell of claim 1, wherein the heterologous nucleic acid encoding the bifunctional alcohol-acetaldehyde dehydrogenase is identical to SEQ ID NO: 20.

6. The recombinant cellulolytic *Clostridium* host cell of claim 1, wherein the host cell is *Clostridium thermocellum.*

7. A composition comprising the host cell from claim 1 and a carbon-containing feedstock, wherein the feedstock is selected from the group consisting of woody biomass, grasses, sugar-processing residues, municipal waste, agricultural wastes and any combination thereof.

8. The composition of claim 7, wherein the feedstock comprises recycled wood pulp fiber, sawdust, hardwood, softwood, rice straw, rice hulls, barley straw, corn cobs, cereal straw, wheat straw, canola straw, oat straw, oat hulls, corn fiber, stover, succulents, agave, cane bagasse, switchgrass, miscanthus, paper sludge, municipal waste or any combination thereof.

9. A method of producing ethanol comprising: (a) providing the host cell of claim 1; (b) culturing the host cell in the presence of a carbon containing feedstock for sufficient time to produce ethanol; and, optionally (c) extracting the ethanol.

* * * * *